(12) United States Patent
Aoki et al.

(10) Patent No.: US 7,815,563 B2
(45) Date of Patent: Oct. 19, 2010

(54) DETECTING SYSTEM OF POSITION AND POSTURE OF CAPSULE MEDICAL DEVICE

(75) Inventors: Isao Aoki, Sagamihara (JP); Akio Uchiyama, Yokohama (JP); Kenichi Arai, Shiogama (JP); Kazushi Ishiyama, Sendai (JP); Shin Yabukami, Sendai (JP)

(73) Assignee: Olympus Corporation, Tokyo (JP)

( * ) Notice: Subject to any disclaimer, the term of this patent is extended or adjusted under 35 U.S.C. 154(b) by 304 days.

(21) Appl. No.: 12/055,142

(22) Filed: Mar. 25, 2008

(65) Prior Publication Data

US 2008/0177177 A1 Jul. 24, 2008

Related U.S. Application Data

(63) Continuation of application No. 11/071,738, filed on Mar. 3, 2005, now Pat. No. 7,751,866.

(30) Foreign Application Priority Data

Mar. 8, 2004 (JP) ............................. 2004-064519
Apr. 19, 2004 (JP) ............................. 2004-123565

(51) Int. Cl.
*A61B 1/00* (2006.01)
(52) U.S. Cl. ..................... 600/101; 600/117; 600/118; 600/424; 607/33; 607/61
(58) Field of Classification Search ................. 600/101, 600/117, 118, 424
See application file for complete search history.

(56) References Cited

U.S. PATENT DOCUMENTS

| 5,273,025 | A | 12/1993 | Sakiyama et al. | |
|---|---|---|---|---|
| 5,727,552 | A * | 3/1998 | Ryan | .......................... 600/407 |
| 6,957,098 | B1 * | 10/2005 | Hyde et al. | .................. 600/424 |
| 7,162,293 | B2 * | 1/2007 | Weiss | .......................... 600/411 |
| 2002/0077546 | A1 | 6/2002 | Aldefeld et al. | |
| 2003/0229268 | A1 * | 12/2003 | Uchiyama et al. | ............ 600/109 |
| 2004/0143182 | A1 * | 7/2004 | Kucera et al. | ................ 600/424 |
| 2005/0154294 | A1 * | 7/2005 | Uchiyama et al. | ............ 600/420 |
| 2005/0261570 | A1 * | 11/2005 | Mate et al. | .................... 600/411 |

FOREIGN PATENT DOCUMENTS

| EP | 1 374 793 A1 | 1/2004 |
|---|---|---|
| JP | 2000-337811 | 12/2000 |
| JP | 2001-179700 | 7/2001 |

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A detecting system of the position and the posture of a capsule medical device includes a main body of the capsule medical device that is inserted in a living body, a coil in a capsule that is arranged to the main body of the capsule medical device and forms a resonant circuit, a magnetic field generating device that is arranged around the living body and generates the Alternating magnetic field for generating an induced magnetic field in the coil in the capsule, and a plurality of magnetic field detecting devices that detect the strength of the induced magnetic field generated by the coil in the capsule by the magnetic field generated by the magnetic field generating device.

12 Claims, 40 Drawing Sheets

FOREIGN PATENT DOCUMENTS

| | | |
|---|---|---|
| JP | 2003-019111 | 1/2003 |
| JP | 2003-044217 | 2/2003 |
| JP | 2003-260026 A | 9/2003 |
| JP | 2003-299612 | 10/2003 |
| JP | 2002-200058 | 2/2004 |
| WO | WO0134049 A2 | 5/2001 |
| WO | WO 2004/014225 A2 | 2/2004 |

* cited by examiner

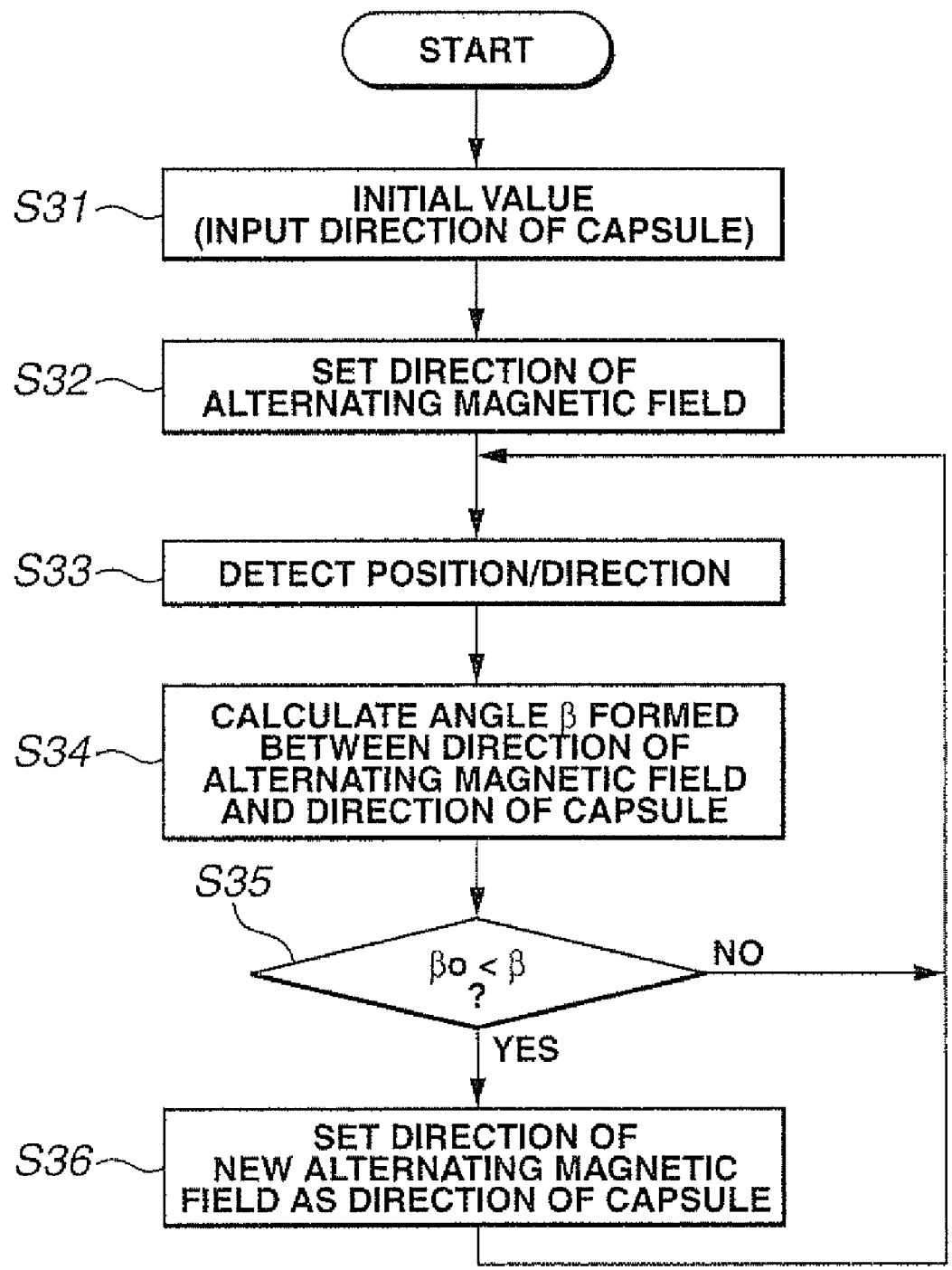

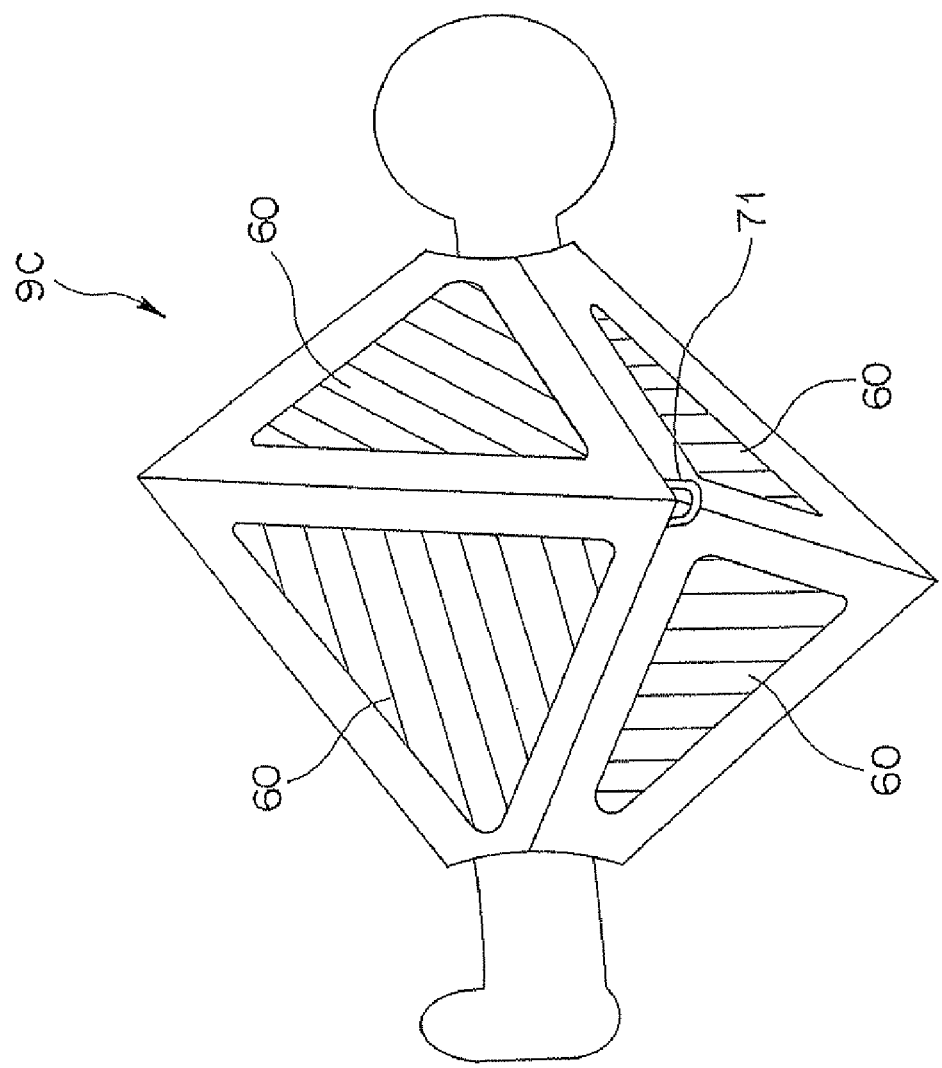

DETECTING SYSTEM OF POSITION AND POSTURE OF CAPSULE MEDICAL DEVICE

This application is a continuation application of U.S. application Ser. No. 11/071,738 filed on Mar. 3, 2005, which claims benefit of Japanese Application Nos. 2004-64519 filed on Mar. 8, 2004, and 2004-123565 filed on Apr. 19, 2004, the entire contents of each of which are incorporated herein by reference.

BACKGROUND OF THE INVENTION

1. Field of the Invention

The present invention relates to a detecting system of the position and the posture of a capsule medical device which detects the direction and the position of a capsule medical device main body inserted in the body cavity.

2. Description of the Related Art

Japanese Unexamined Patent Application Publication No. 2001-179700 discloses a conventional art for advancing operation in an examinee by a rotating magnetic field. As disclosed in Japanese Unexamined Patent Application Publication No. 2001-179700, a movement control system of a movable micro-machine comprises a magnetic field generating unit for generating a rotating magnetic field, a robot main body for obtaining thrust by the rotation generated by the applied rotating magnetic field, a position detecting unit for detecting the position of the robot main body, and magnetic field changing means for changing the direction of the rotating magnetic field generated by the magnetic field generating unit based on the position of the robot main body detected by the position detecting unit so that the robot main body reaches the target position.

In the position detecting unit used for the movement control system of the micro-machine, a magnetic sensor detects the magnetic field generated by a magnet incorporated in the micro-machine to detect the position of the micro-machine.

Further, in the movement control system of the micro-machine disclosed in Japanese Unexamined Patent Application Publication No. 2001-179700, the micro-machine relatively freely changes the direction in solution serving as a gel material by indicating the next moving direction based on position information in the movement in the solution.

SUMMARY OF THE INVENTION

A detecting system of the position and the posture of a capsule medical device comprises a main body of the capsule medical device that is inserted in the living body, a coil in a capsule that is arranged to the main body of the capsule medical device and forms a resonant circuit, magnetic field generating means that is arranged around the living body and generates the Alternating magnetic field for generating the induced magnetic field in the coil in the capsule, and a plurality of magnetic field detecting means that detects the strength of an induced magnetic field generated by the coil in the capsule by the magnetic field generated by the magnetic field generating means.

BRIEF DESCRIPTION OF THE DRAWINGS

FIG. 15A is a perspective view showing the example of the arrangement pattern of the detecting coil and the exciting coil arranged to the position and posture detecting substrate.

FIG. 15B is a top view showing the position and posture detecting device and the rotating magnetic field generating device shown in FIG. 15A.

FIG. 16A is a perspective view showing a first one of other examples of the arrangement pattern of the detecting coil and the exciting coil arranged to the position and posture detecting substrate.

FIG. 16B is a perspective view showing a second one of other examples of the arrangement pattern of the detecting coil and the exciting coil arranged to the position and posture detecting substrate.

FIG. 16C is a perspective view showing a third one of other examples of the arrangement pattern of the detecting coil and the exciting coil arranged to the position and posture detecting substrate.

FIG. 17A is a perspective view schematically showing the appearance of the rotating magnetic field generating device and the position and posture detecting device shown in FIG. 10.

FIG. 17B is a sectional view schematically showing the inner structure of the rotating magnetic field generating device and the position and posture detecting device shown in FIG. 17A.

FIG. 23 is a flowchart showing the control operation sequential to the flowchart shown in FIG. 20 or 22.

FIG. 24A is an explanatory diagram of the side of the capsule main body in which the coil is wound to a covering member for covering components.

FIG. 24B is an explanatory diagram of the cross-sectional shape of the covering member shown in FIG. 24A.

FIG. 24C is an explanatory diagram of the side of the capsule main body in which the coil is wound to a stick member.

FIG. 25A is a circuit block diagram showing a first power-supply circuit.

FIG. 25B is a circuit block diagram showing a second power-supply circuit.

FIG. 25C is a circuit block diagram showing a third power-supply circuit.

FIG. 26A is a perspective view schematically showing the rotating magnetic field generating device and the position and posture detecting device shown in FIG. 8 according to a third modification.

FIG. 26B is a sectional view schematically showing the inner structure of the rotating magnetic field generating device and the position and posture detecting device shown in FIG. 26A in the direction of an arrow A according to the third modification.

FIG. 27 is a perspective view schematically showing the rotating magnetic field generating device and the position and posture detecting device shown in FIG. 8 according to a fourth modification.

FIG. 28A is a perspective view schematically showing the position and posture detecting device shown in FIG. 8 according to a fifth modification.

FIG. 28B is a sectional view schematically showing the inner structure of the position and posture detecting device shown in FIG. 28A.

FIG. 29A is a perspective view schematically showing the rotating magnetic field generating device and the position and posture detecting device forming the detecting system of the position and the posture of the capsule medical device according to the second embodiment.

FIG. 29B is a sectional view schematically showing the inner structure of the rotating magnetic field generating device and the position and posture detecting device shown in FIG. 29A.

FIG. 40A is an explanatory diagram schematically showing the position relationship when the axis connecting the exciting coil and the detecting coil is coaxial to the coil in the capsule.

FIG. 40B is an explanatory diagram schematically showing the position relationship when the axis connecting the exciting coil and the detecting coil is perpendicular to the central axis of the coil in the capsule in the longitudinal direction.

FIG. 40C is an explanatory diagram schematically showing the position relationship when the coil in the capsule is out of the axis connecting the exciting coil and the detecting coil.

DETAILED DESCRIPTION OF THE PREFERRED EMBODIMENTS

Hereinbelow, a description is given of embodiments of the present invention.

First Embodiment

Figure 1:
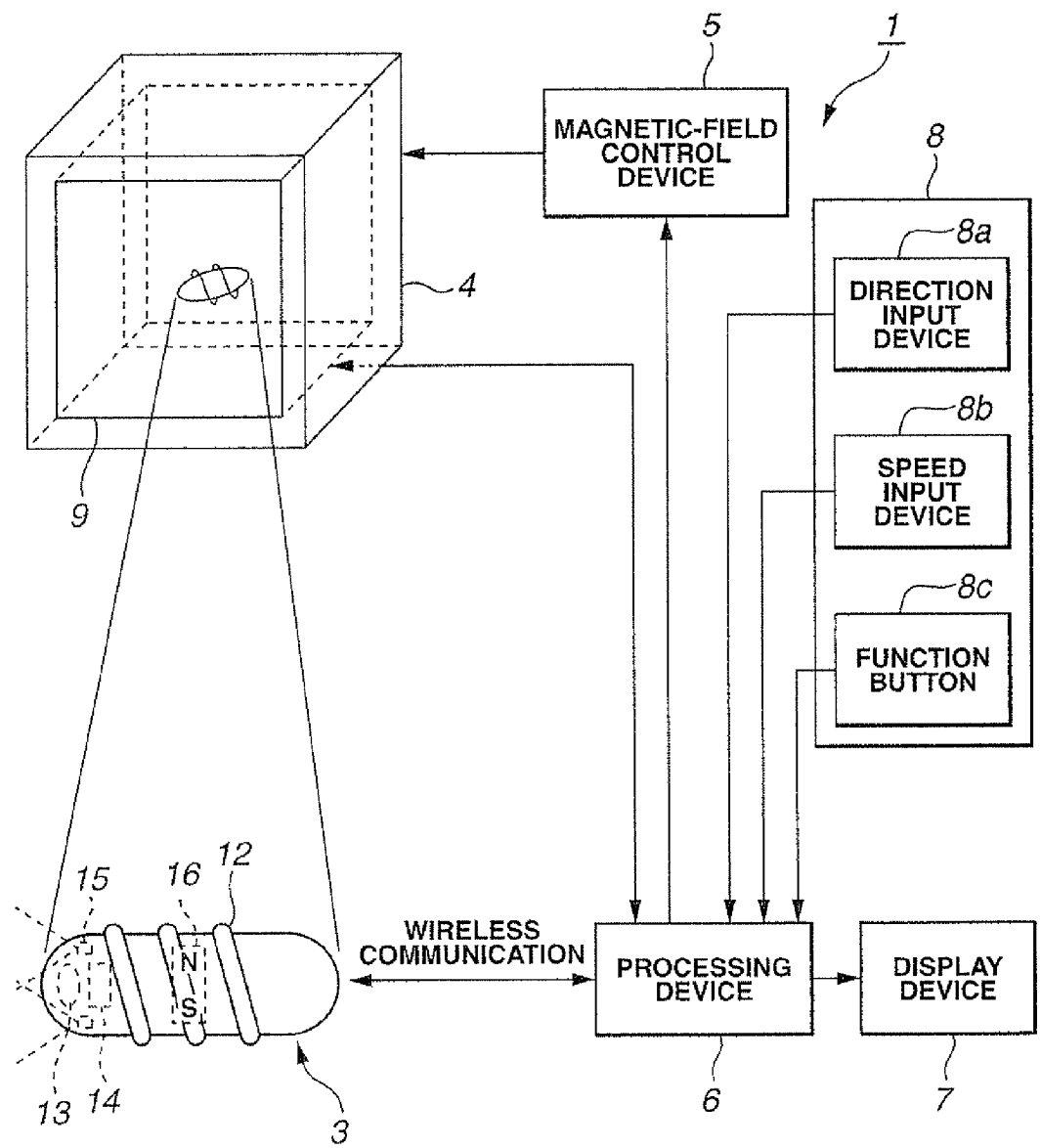
FIG. 1 is a diagram showing the entire structure of a detecting system of the position and the posture of a capsule medical device according to a first embodiment.
Figure 3:
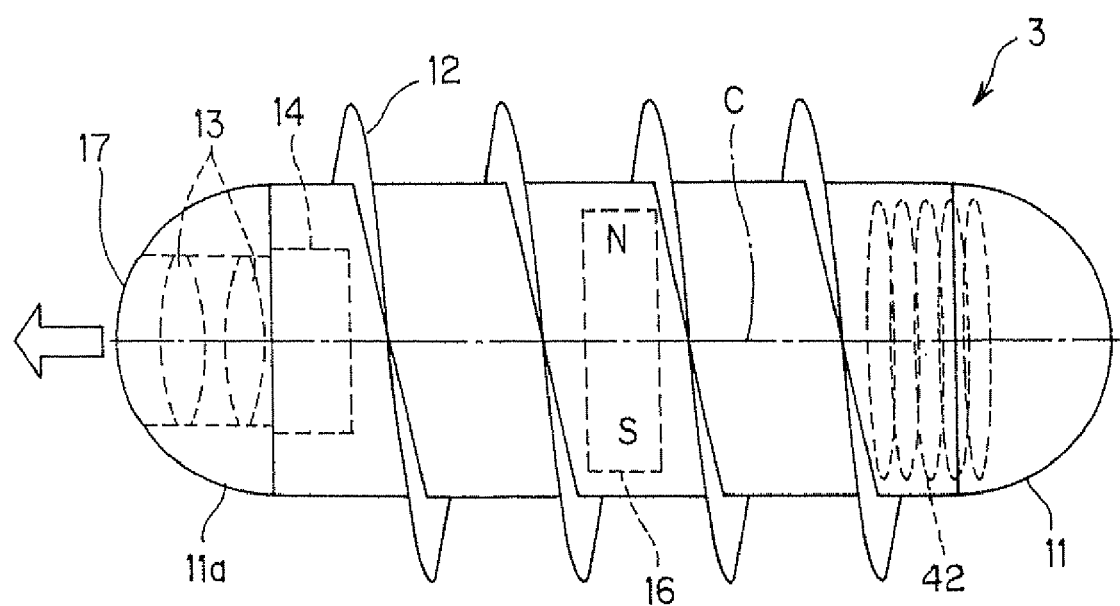
FIG. 3 is an explanatory diagram of the side of a capsule main body.
Figure 4:
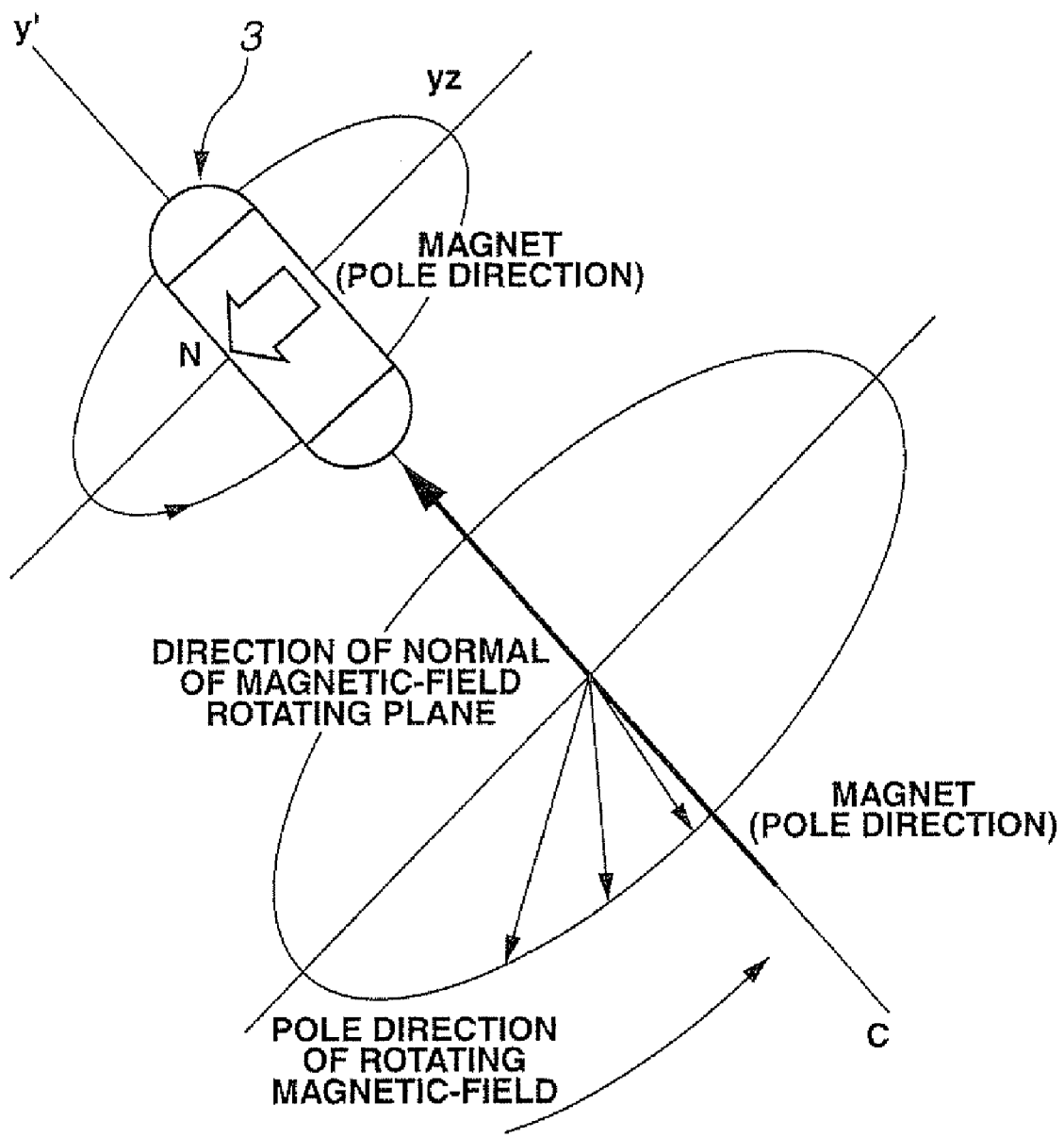
FIG. 4 is a conceptual diagram showing an applied rotating magnetic field and the operation of the capsule main body that is caused by the rotating magnetic field.
Figure 5:
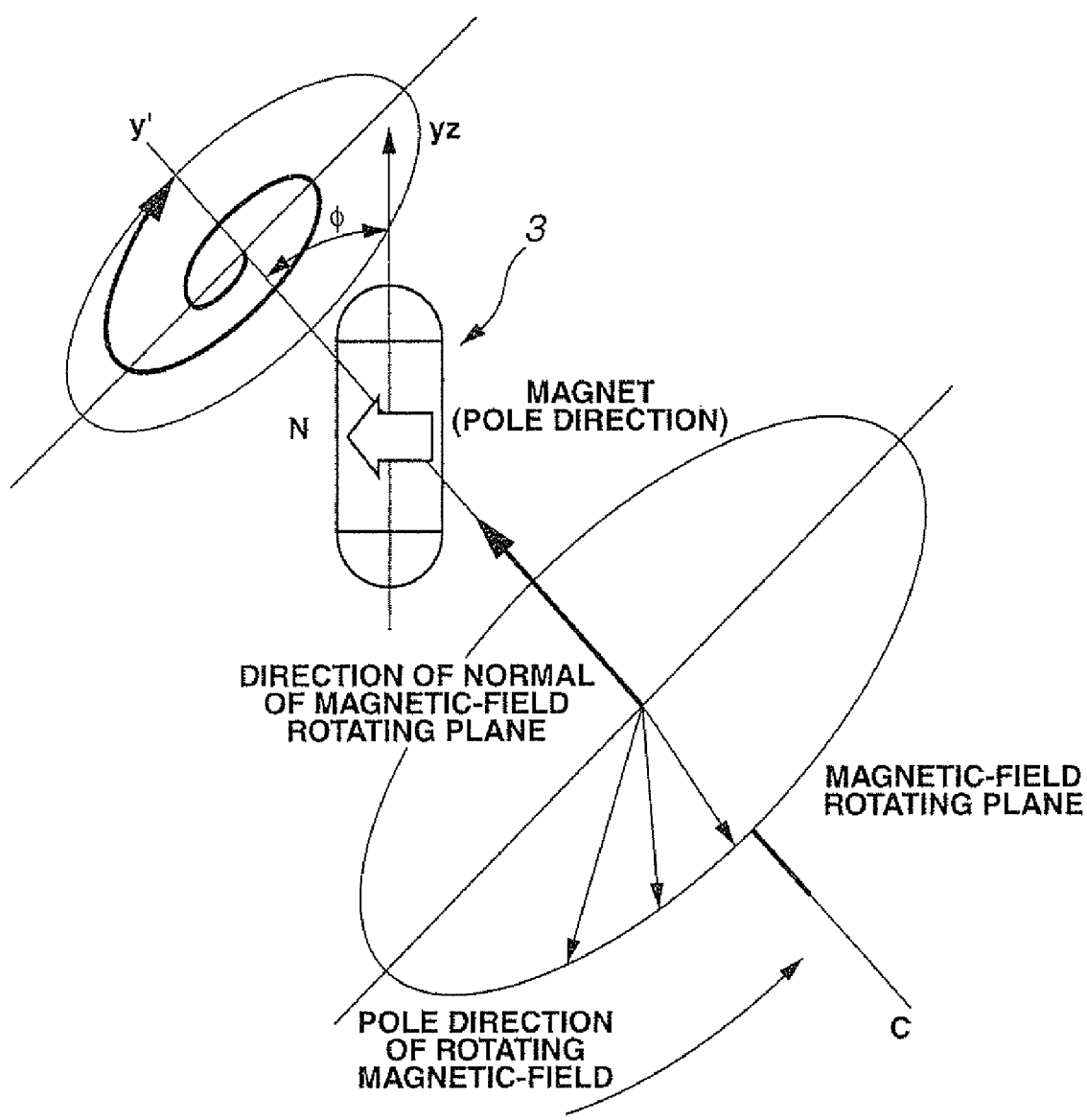
FIG. 5 is a conceptual diagram showing a vibrating magnetic field (magnetic field for generating a couple) applied to the rotating magnetic field shown in FIG. 4 and the operation of the capsule main body that is caused by the vibrating magnetic field (magnetic field for generating the couple).
Figure 6:
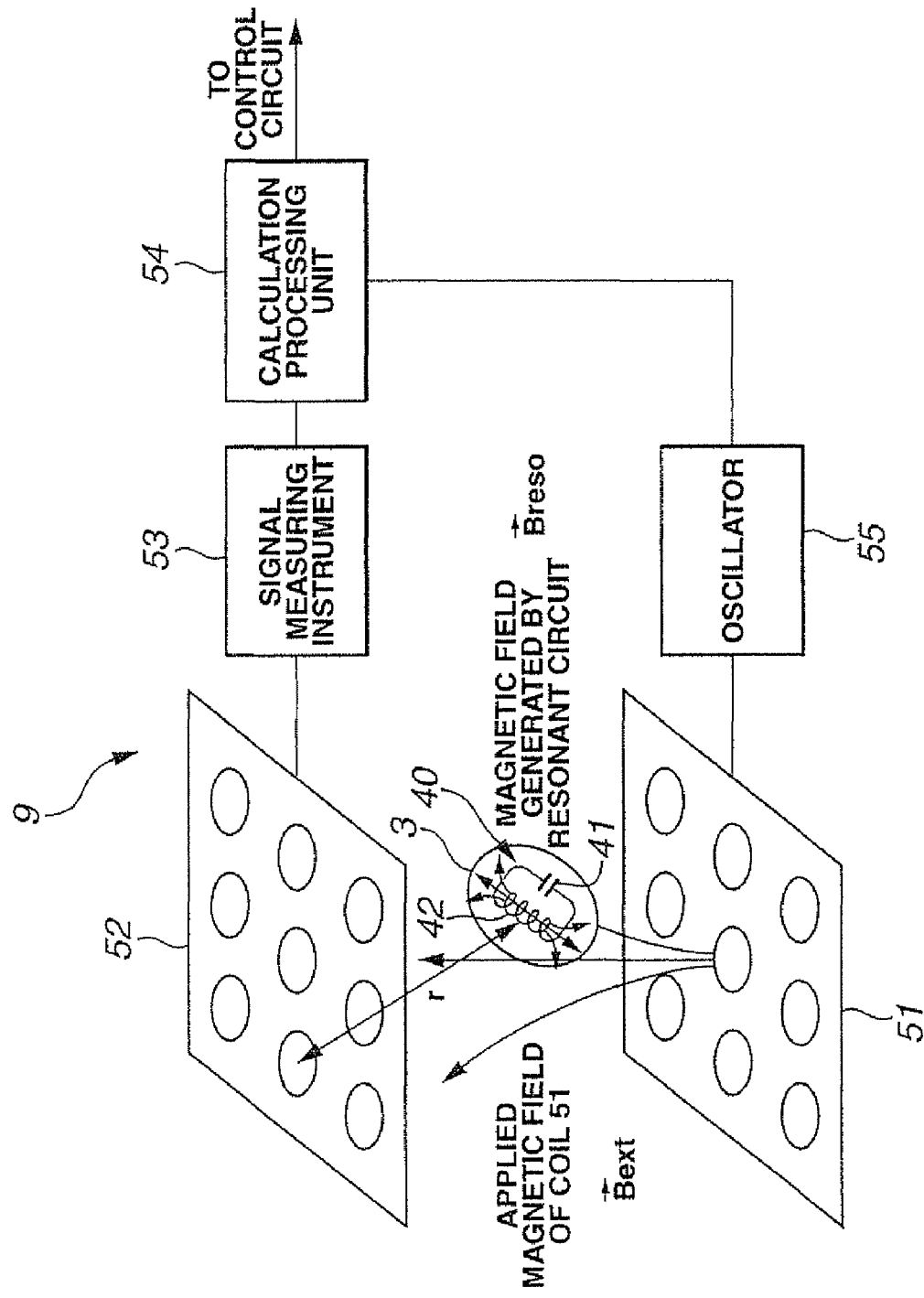
FIG. 6 is an explanatory diagram of the detection of position and posture of a position and posture detecting device to the capsule main body.
Figure 7:
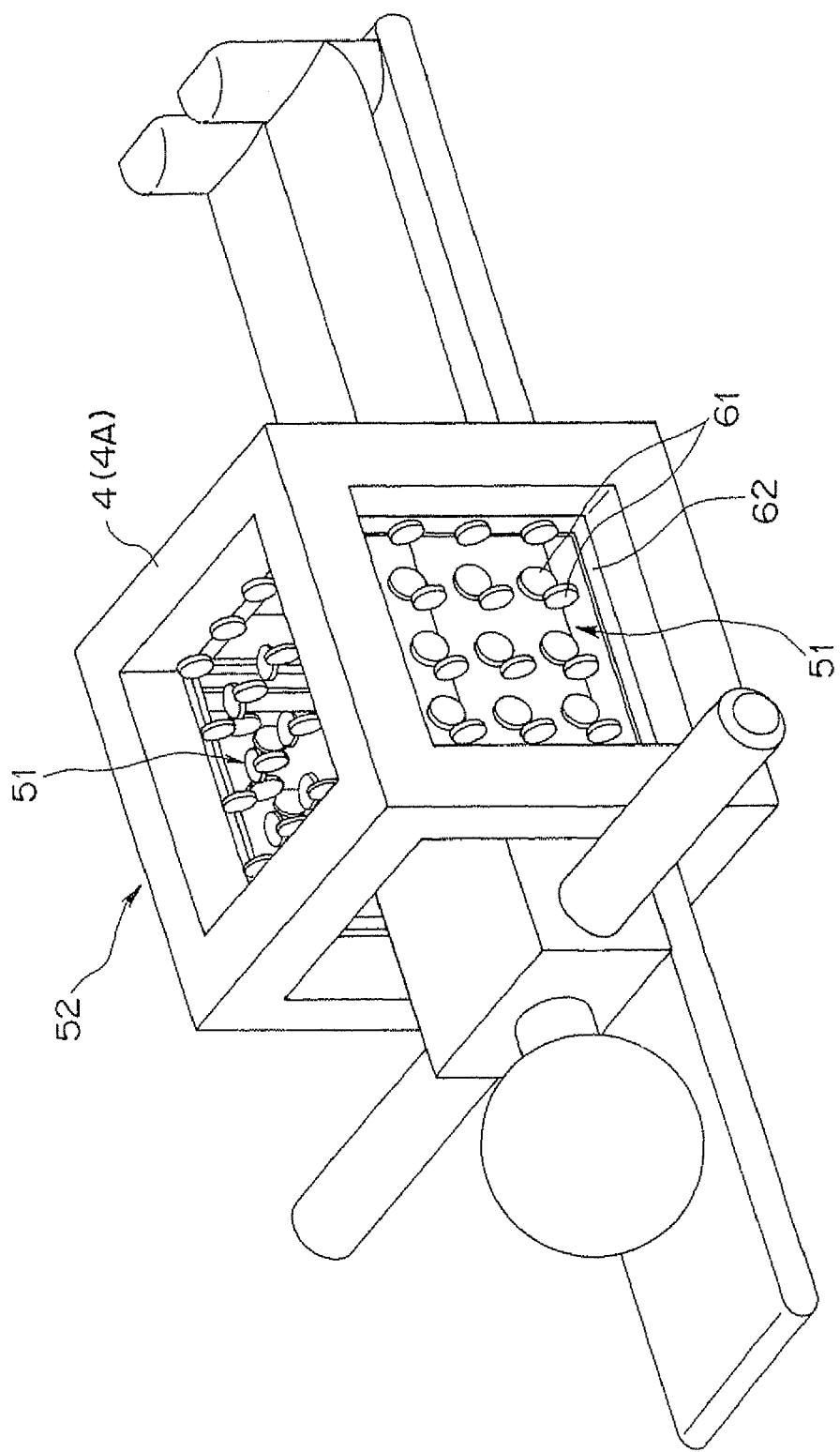
FIG. 7 is an explanatory diagram showing the position and posture detecting device and a rotating magnetic field generating device.
Figure 8:
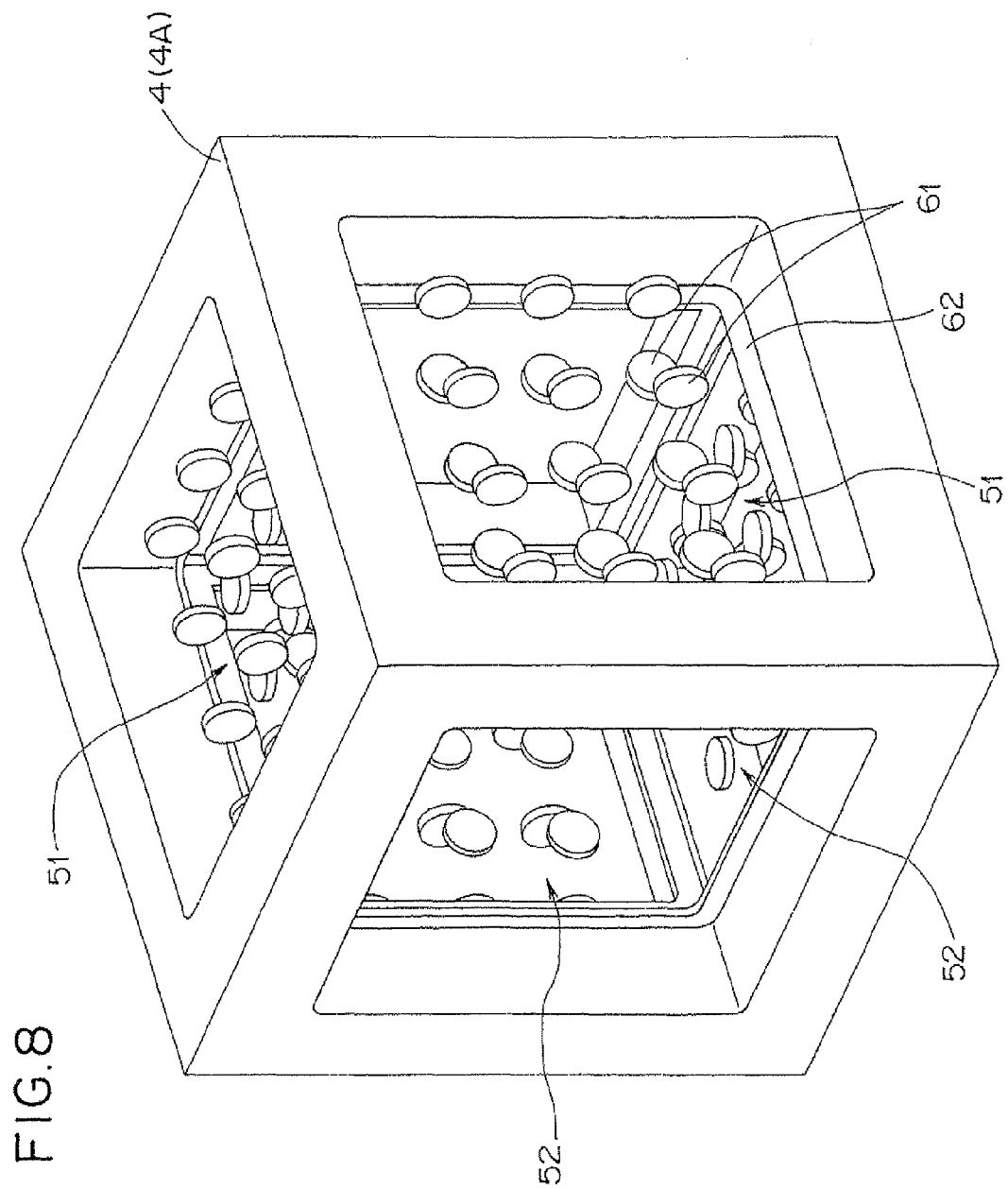
FIG. 8 is an enlarged perspective view showing the rotating magnetic field generating device and the position and posture detecting device shown in FIG. 7.
Figure 9:
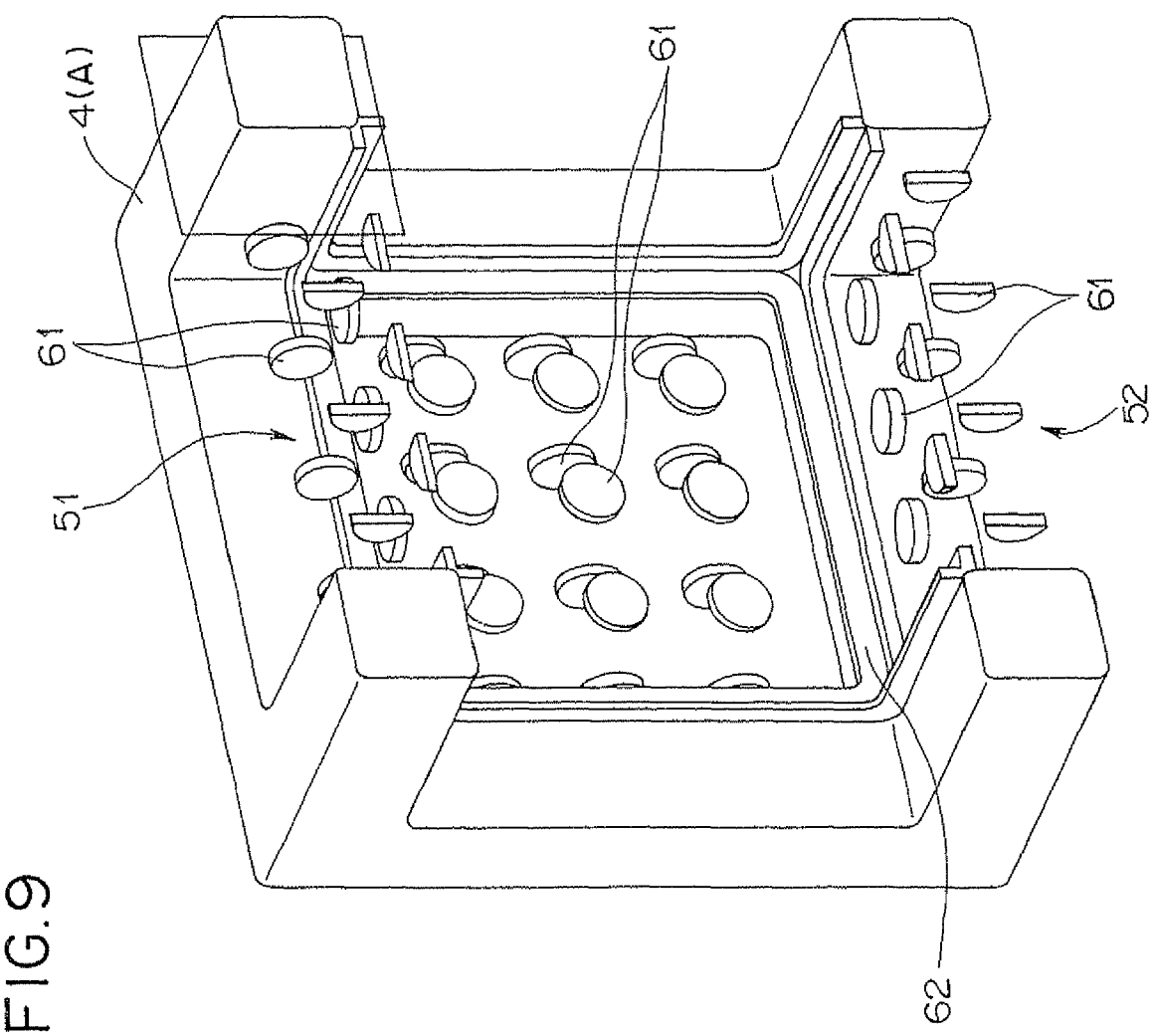
FIG. 9 is a cutaway view showing the rotating magnetic field generating device and the position and posture detecting device shown in FIG. 8.
Figure 10:
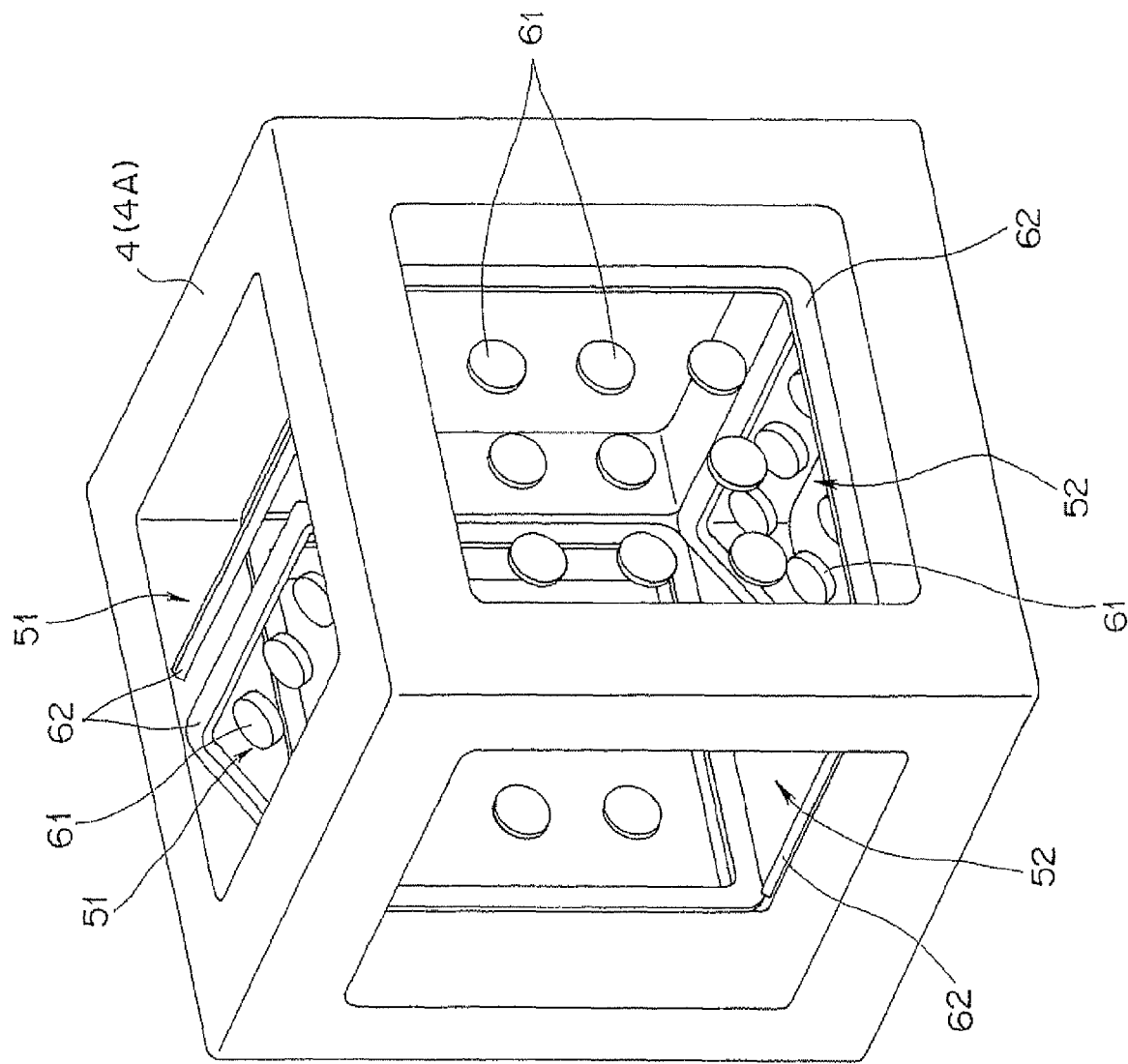
FIG. 10 is a perspective view showing a position and posture detecting device shown in FIG. 8 according to a modification.
Figure 11:
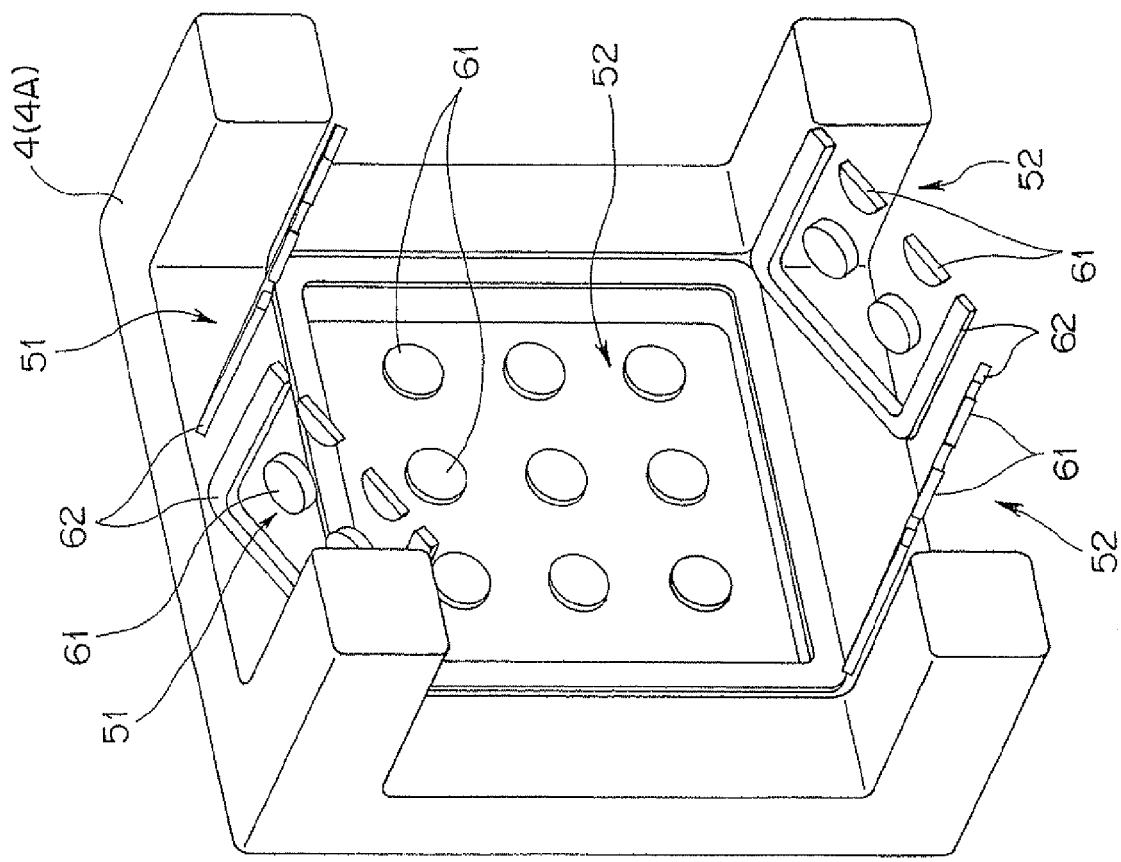
FIG. 11 is a cutaway view showing the rotating magnetic field generating device and the position and posture detecting device shown in FIG. 10.
Figure 12:
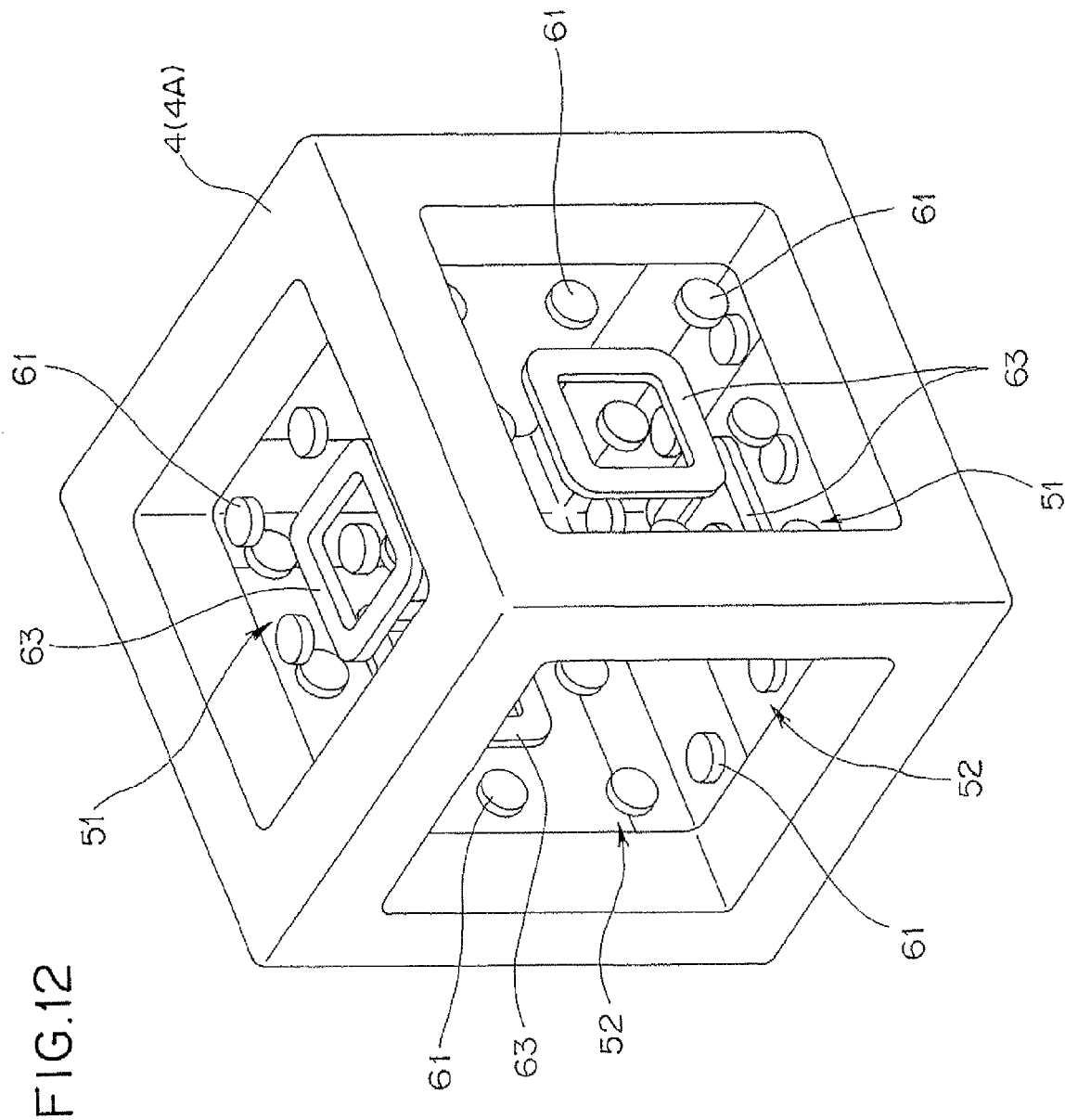
FIG. 12 is a perspective view showing the rotating magnetic field generating device and the position and posture detecting device shown in FIG. 8 according to a second modification.
Figure 13:
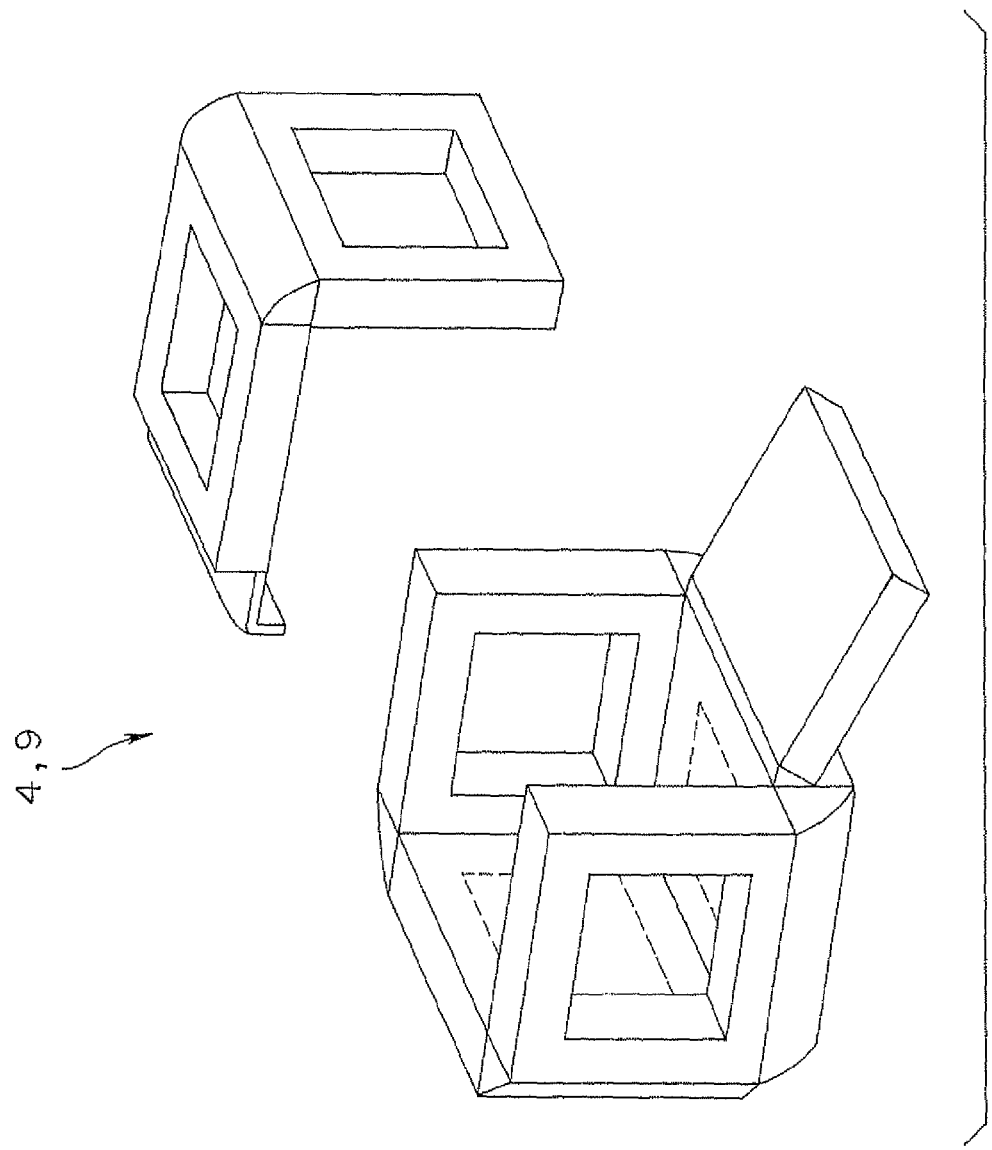
FIG. 13 is a schematic diagram showing the rotating magnetic field generating device which can be divided into two and the position and posture detecting device.
Figure 14:
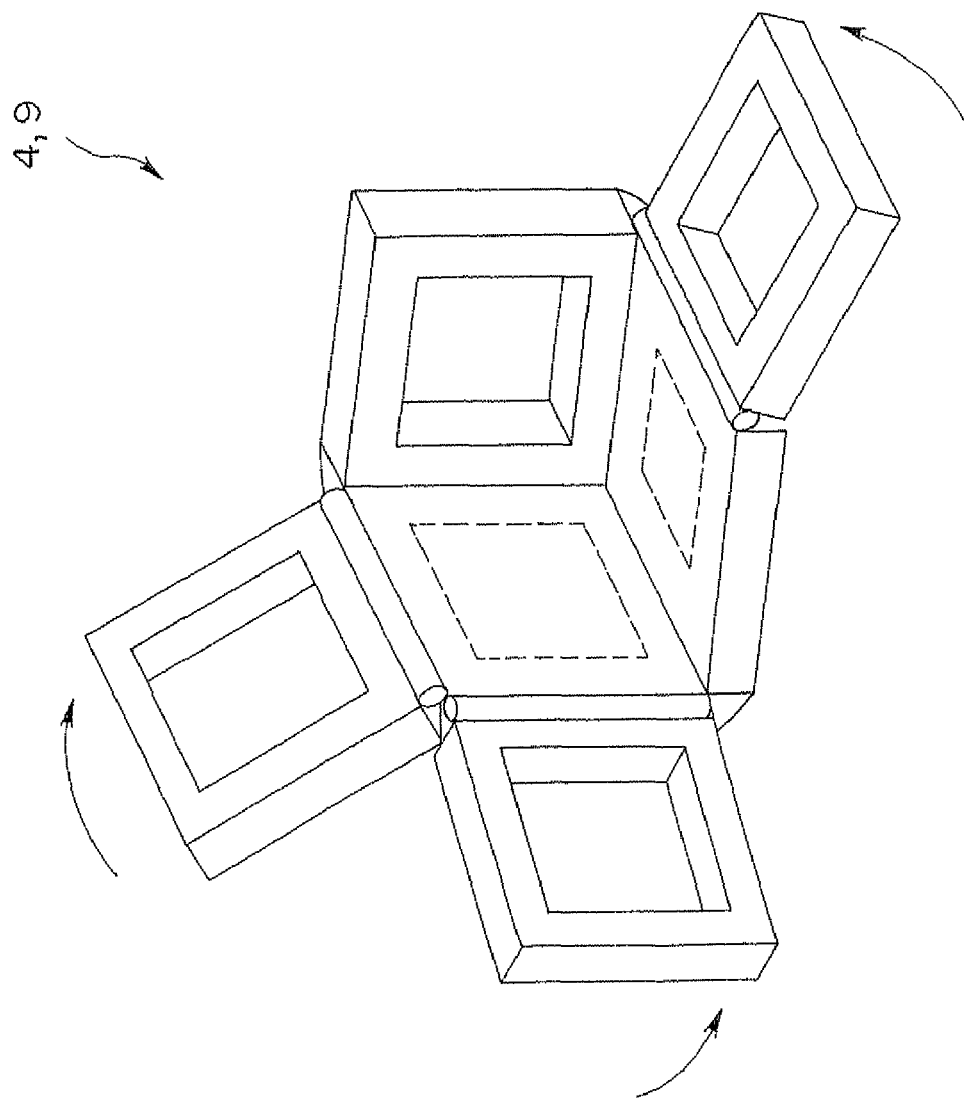
FIG. 14 is a schematic diagram showing the rotating magnetic field generating device which can be opened/closed and the position and posture detecting device.
Figure 15A:
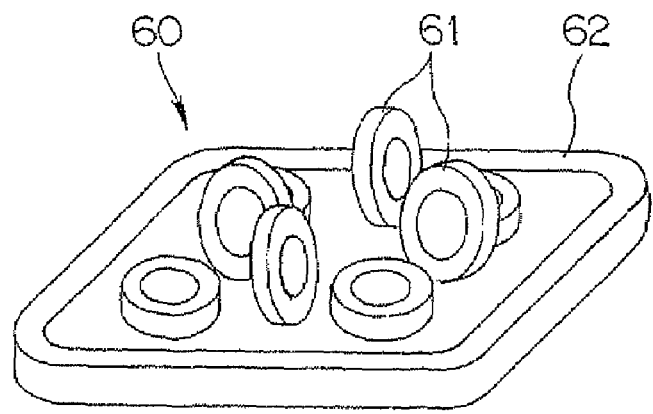
FIGS. 15A and 15B are explanatory diagrams of examples of arrangement patterns of a detecting coil and an exciting coil arranged on a position and posture detecting substrate.
Figure 15B:
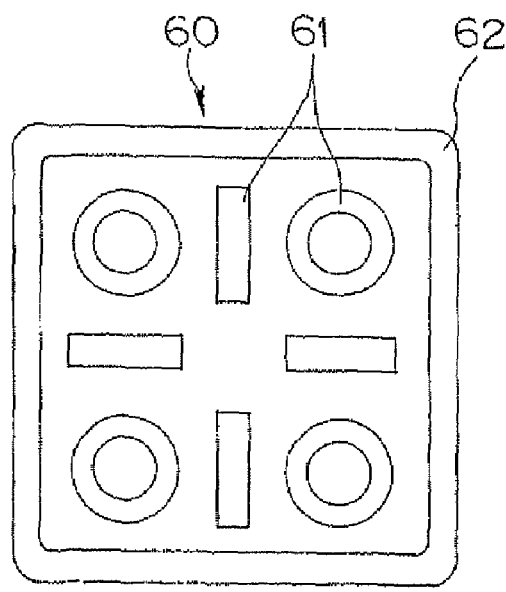
Figure 16A:
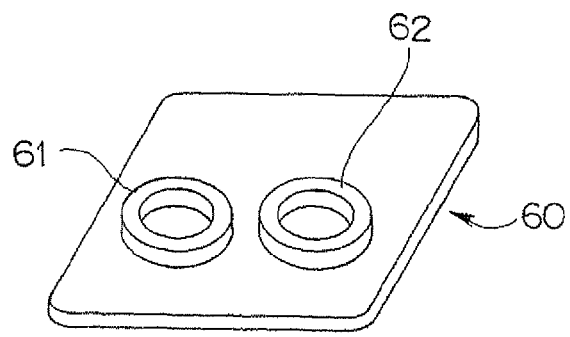
FIGS. 16A to 16C are explanatory diagrams of other examples of the arrangement patterns of the detecting coil and the exciting coil arranged to the position and posture detecting substrate.
Figure 16B:
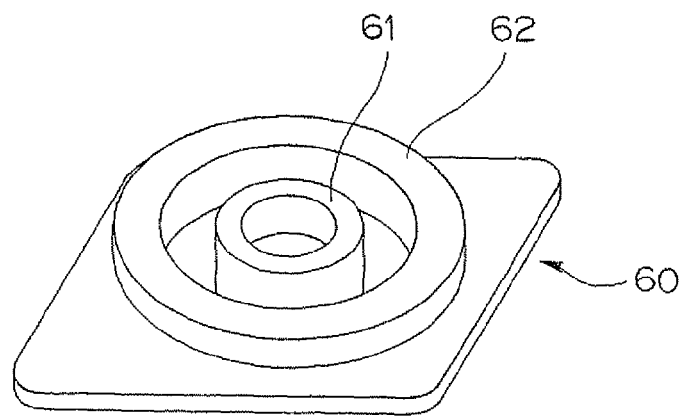
Figure 16C:
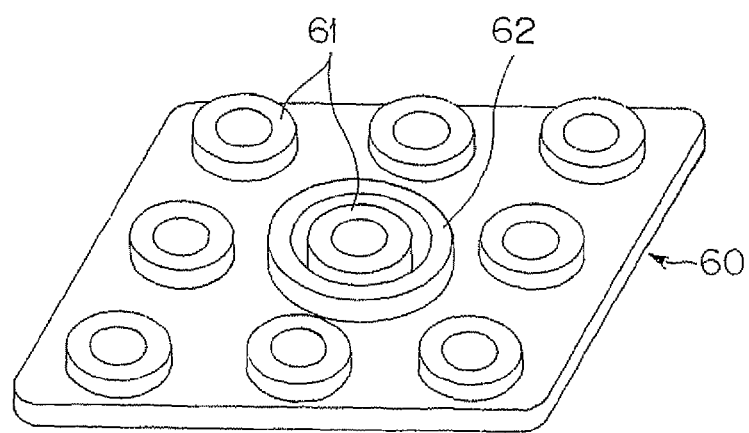
Figure 17A:
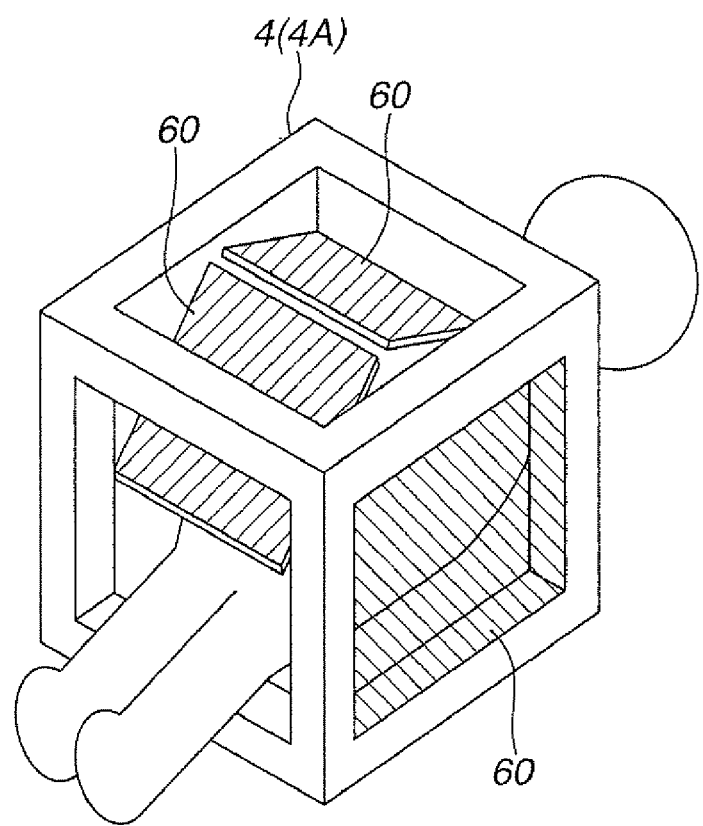
FIGS. 17A and 17B are explanatory diagrams schematically showing the rotating magnetic field generating device and the position and posture detecting device shown in FIG. 10.
Figure 17B:
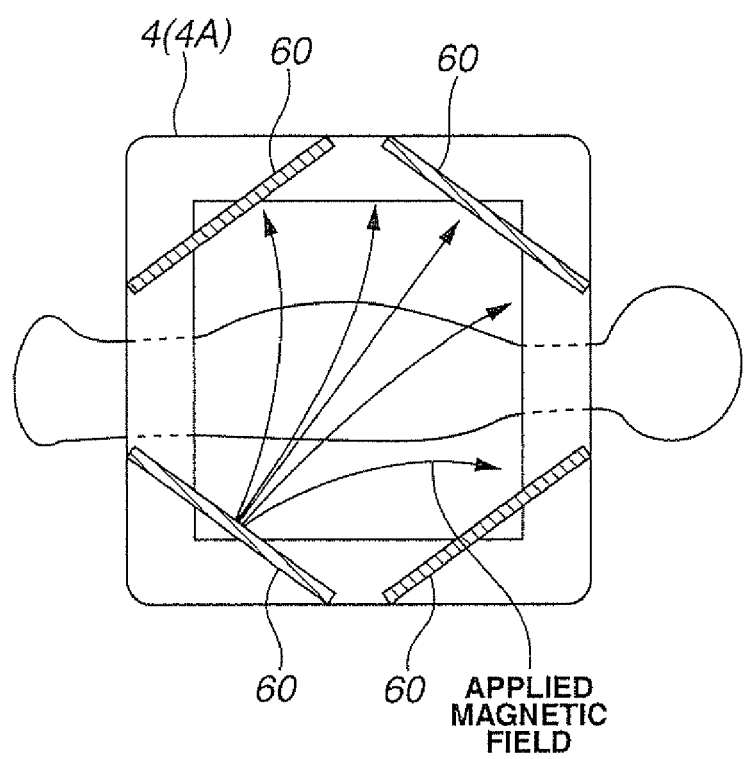
Figure 18:
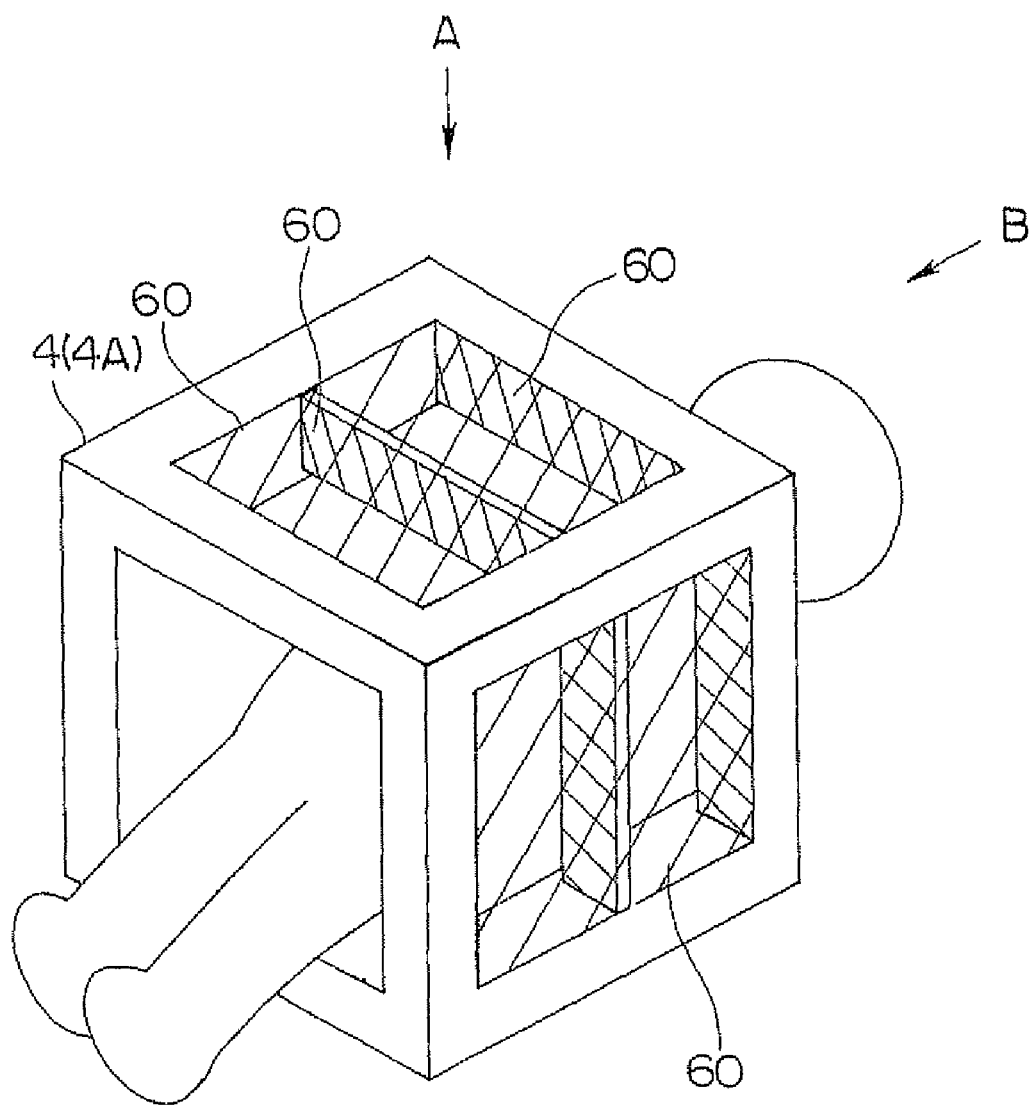
FIG. 18 is a perspective view schematically showing the appearance of the rotating magnetic field generating device and the position and posture detecting device shown in FIG. 12.
Figure 19A:
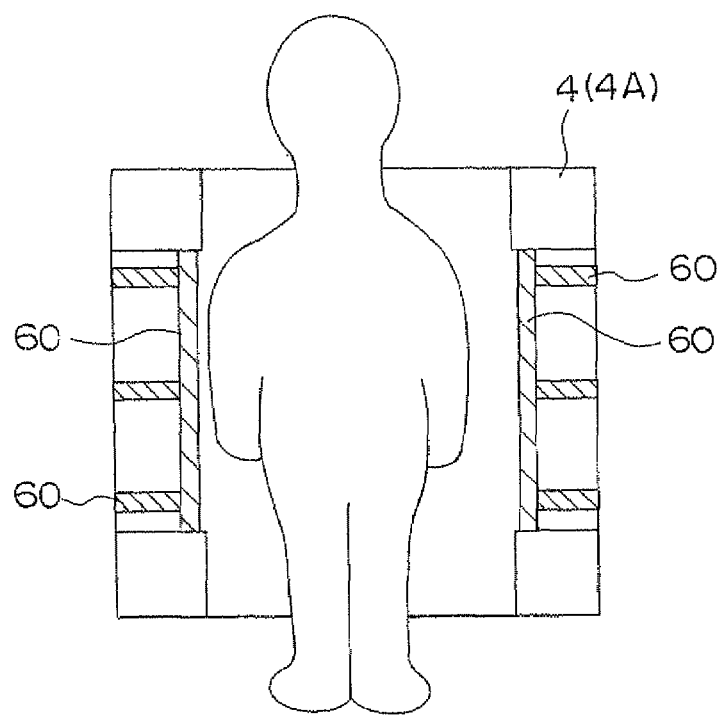
FIG. 19A is a sectional view schematically showing the inner structure of the rotating magnetic field generating device and the position and posture detecting device shown in FIG. 18 in the direction of an arrow A.
Figure 19B:
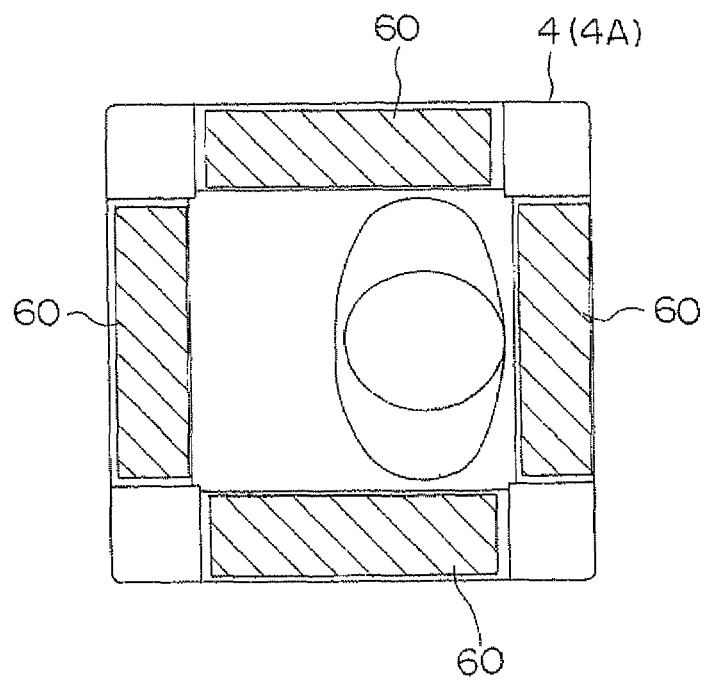
FIG. 19B is a sectional view schematically showing the inner structure of the rotating magnetic field generating device and the position and posture detecting device shown in FIG. 18 in the direction of an arrow B.
Figure 20:
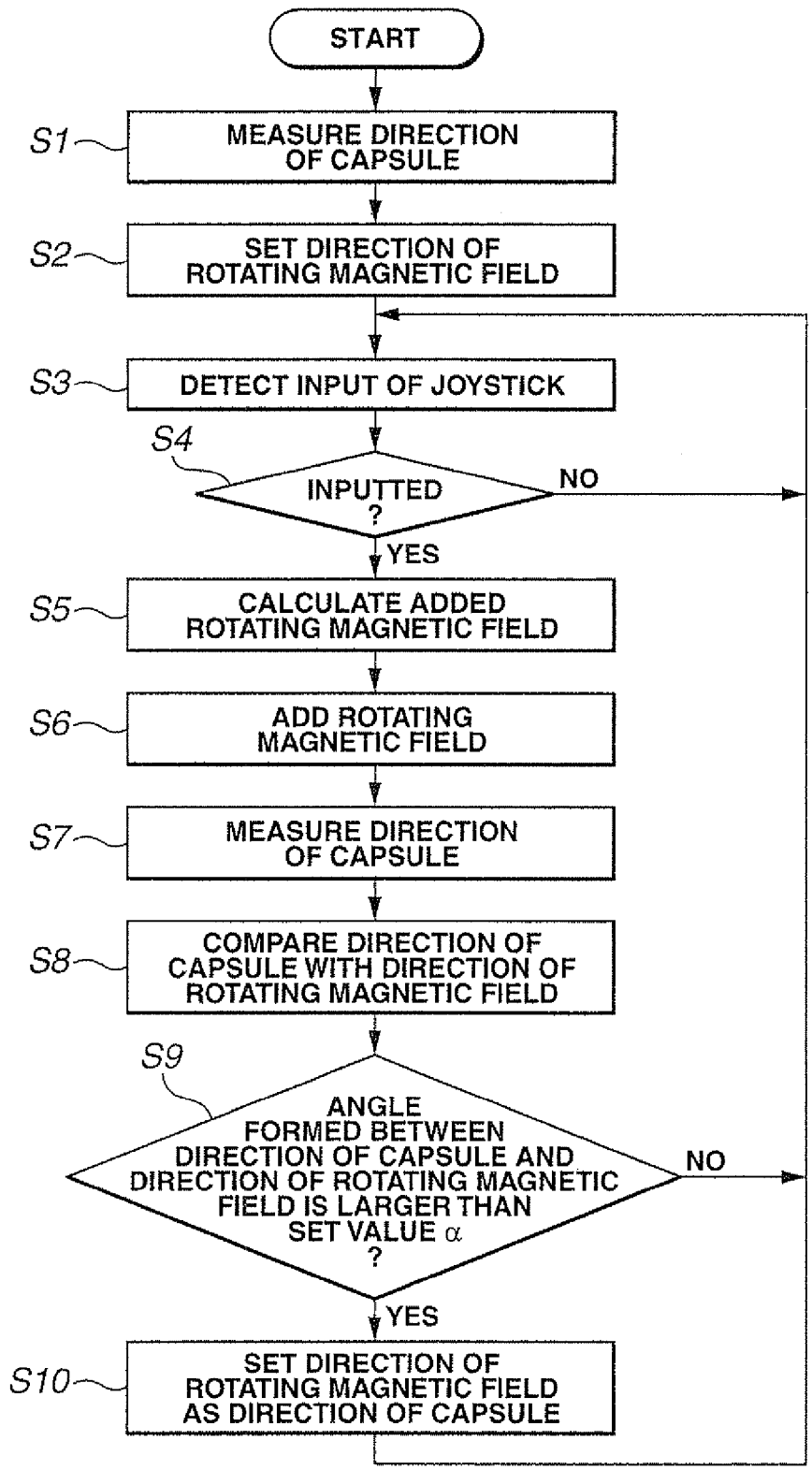
FIG. 20 is a flowchart showing the operation for controlling the direction of the rotating magnetic field based on information on the direction and the position of the capsule main body detected by a direction/position detecting device.
Figure 21:
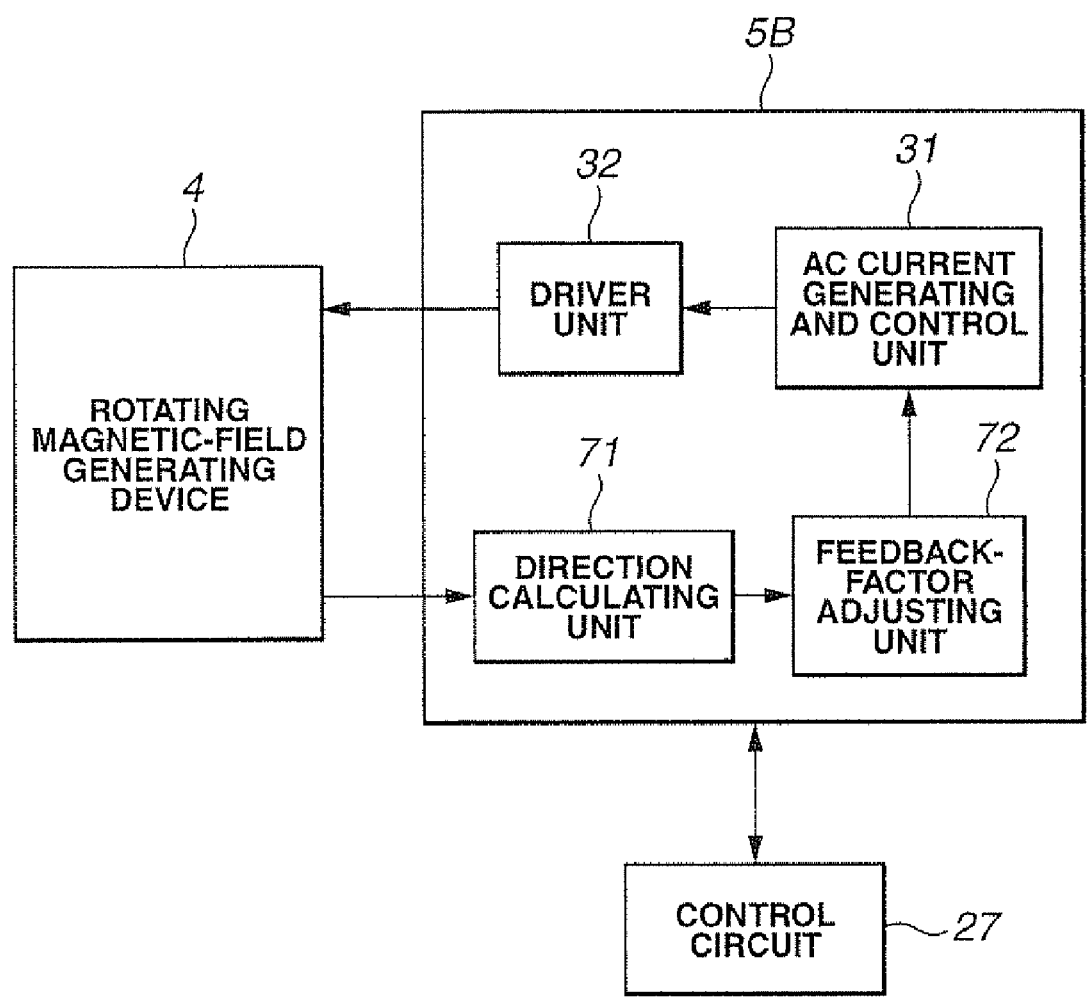
FIG. 21 is a circuit block diagram showing the direction/position detecting device shown in FIG. 2 according to the modification.
Figure 22:
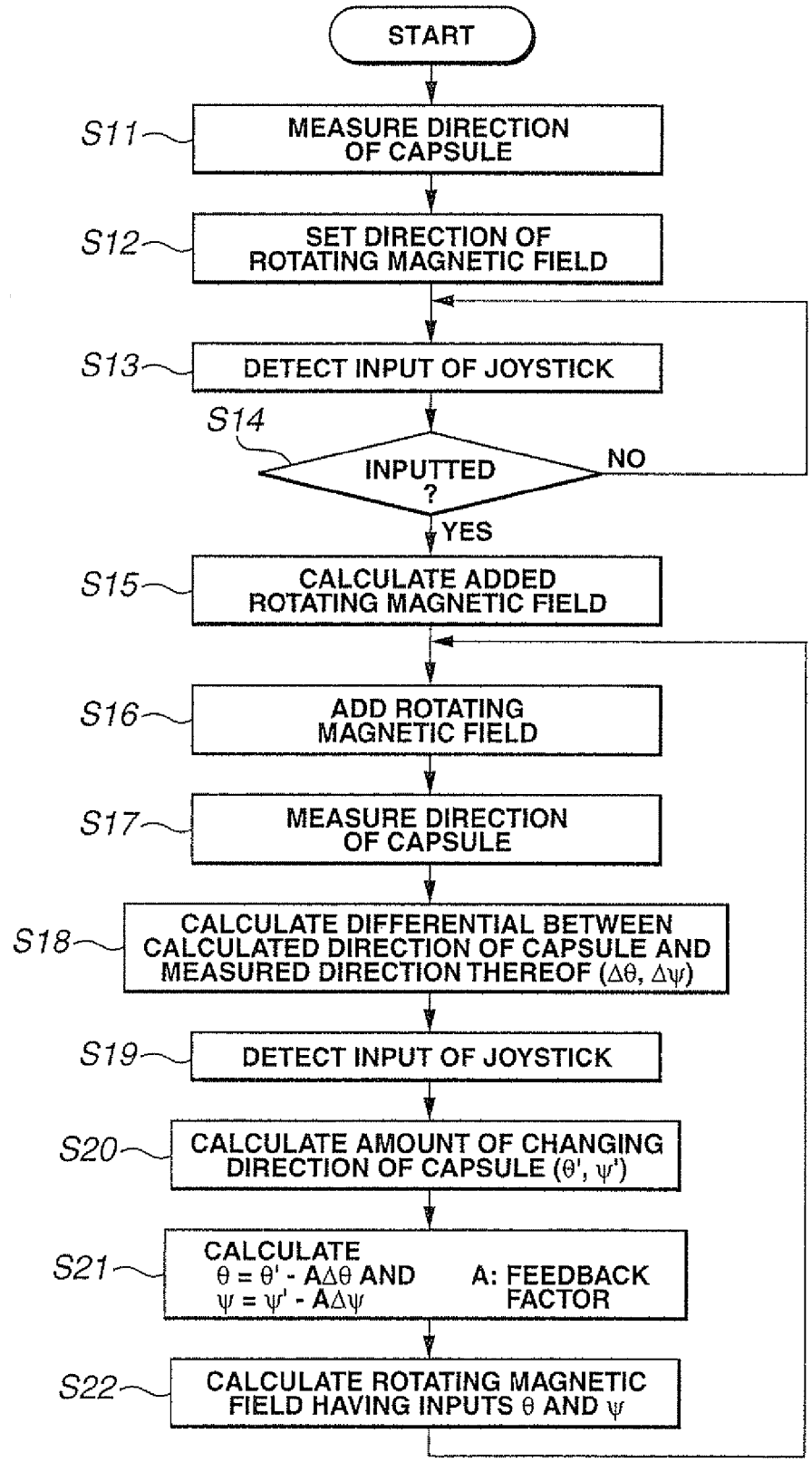
FIG. 22 is a flowchart showing the operation for controlling the direction of the rotating magnetic field based on information on the direction and the position of the capsule main body detected by the direction/position detecting device shown in FIG. 21.
Figure 24B:
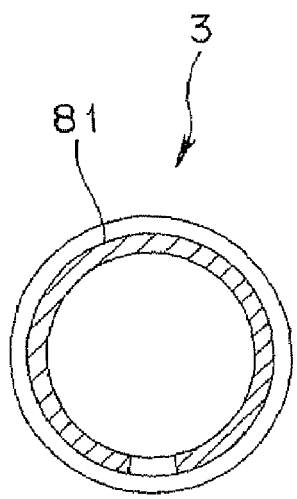
FIGS. 24A to 24C are explanatory diagrams of a coil forming a resonant circuit of a capsule main body according to a modification.
Figure 24A:
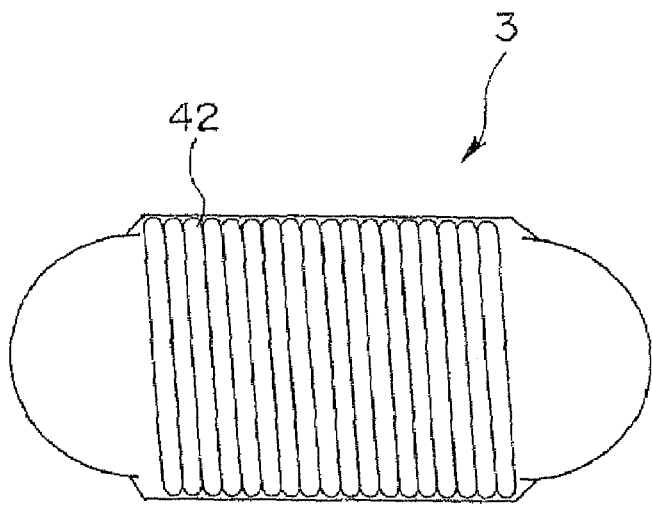
Figure 24C:
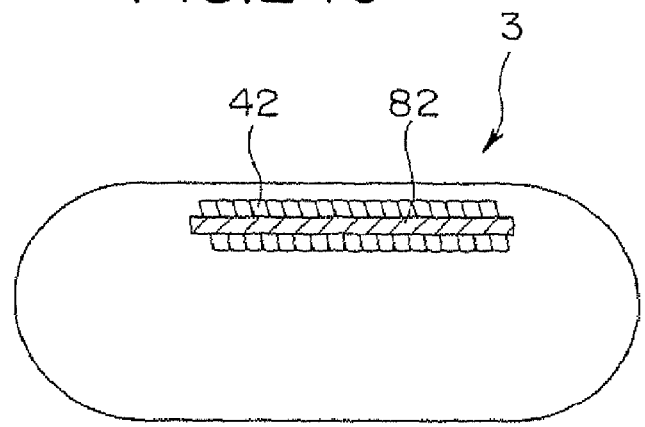
Figure 25A:
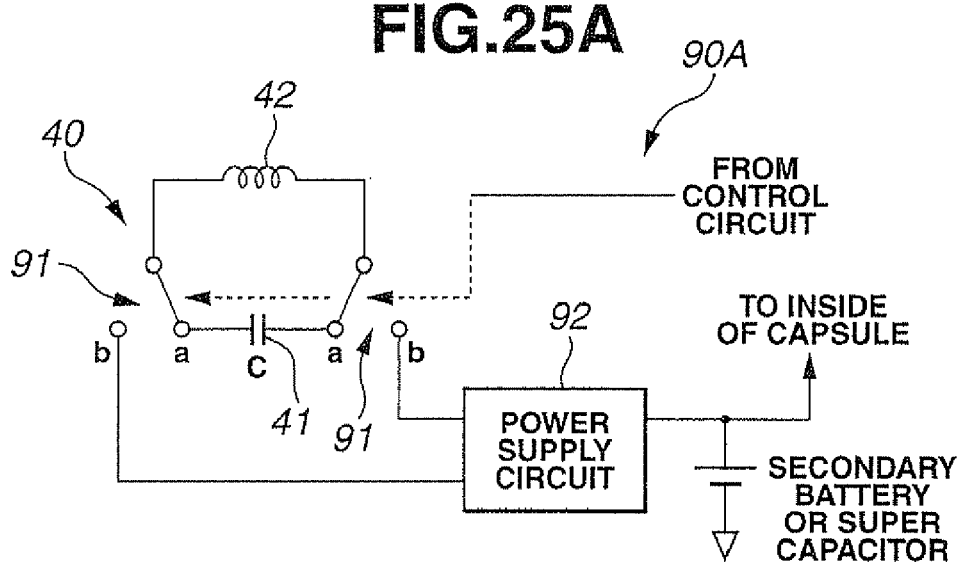
FIGS. 25A to 25C are circuit block diagrams showing power supply circuits comprising the resonant circuit comprising the coils shown in FIGS. 24A to 24C.
Figure 25B:
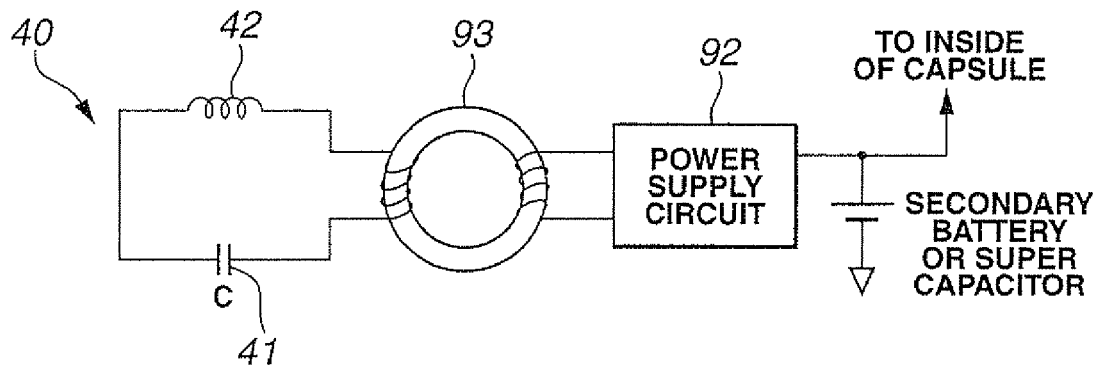
Figure 25C:
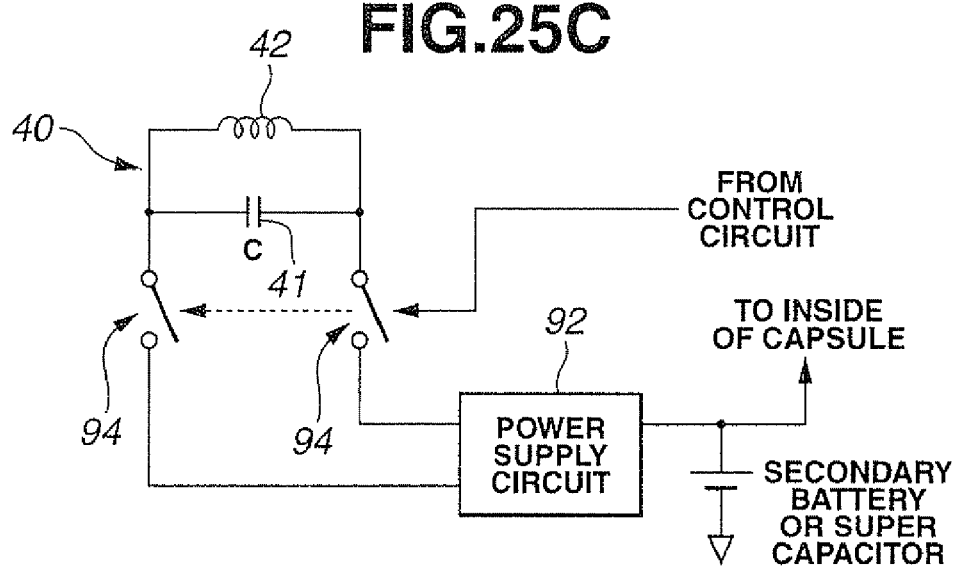
Figure 26A:
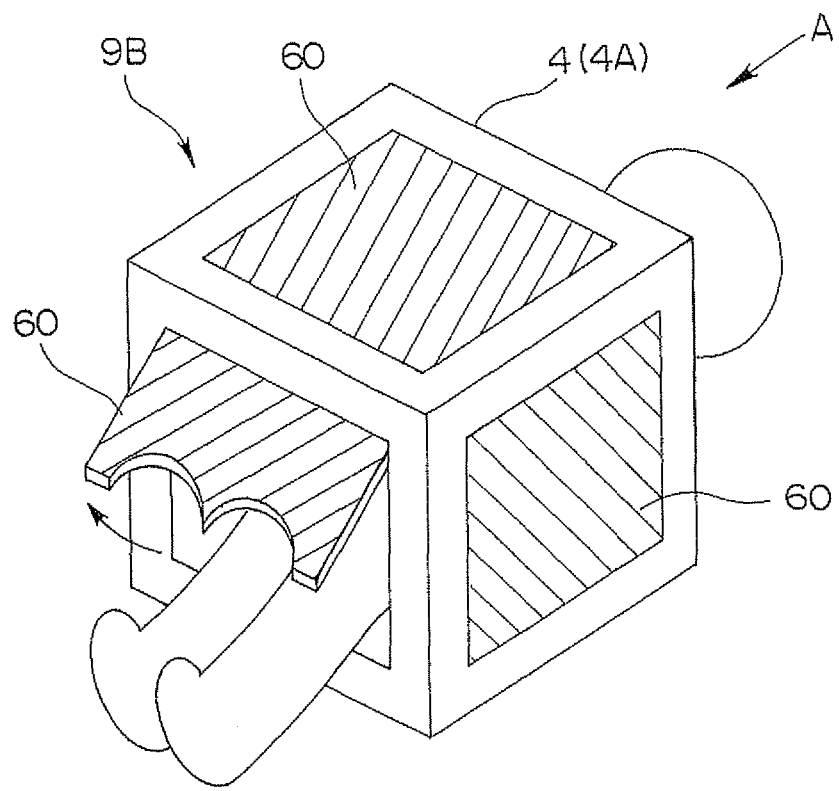
FIGS. 26A and 26B are explanatory diagrams schematically showing the rotating magnetic field generating device and the position and posture detecting device shown in FIG. 8 according to the third modification.
Figure 26B:
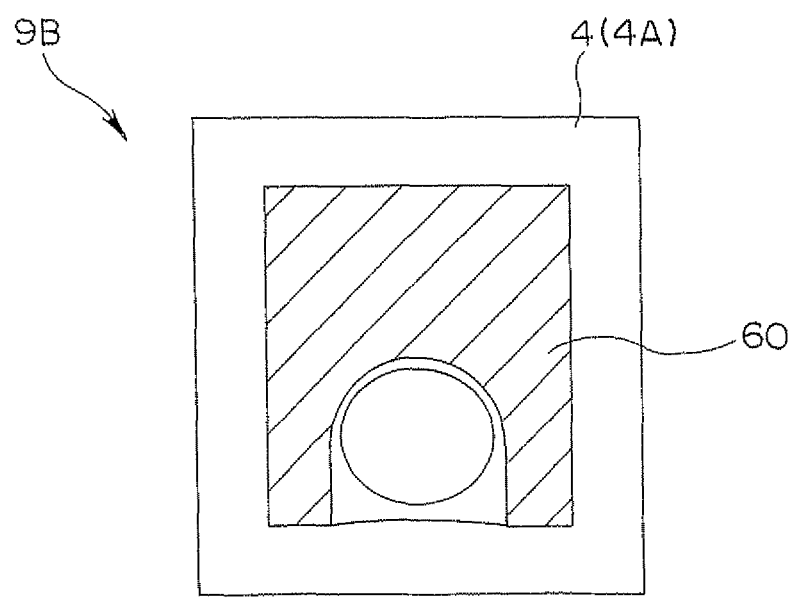
Figure 28A:
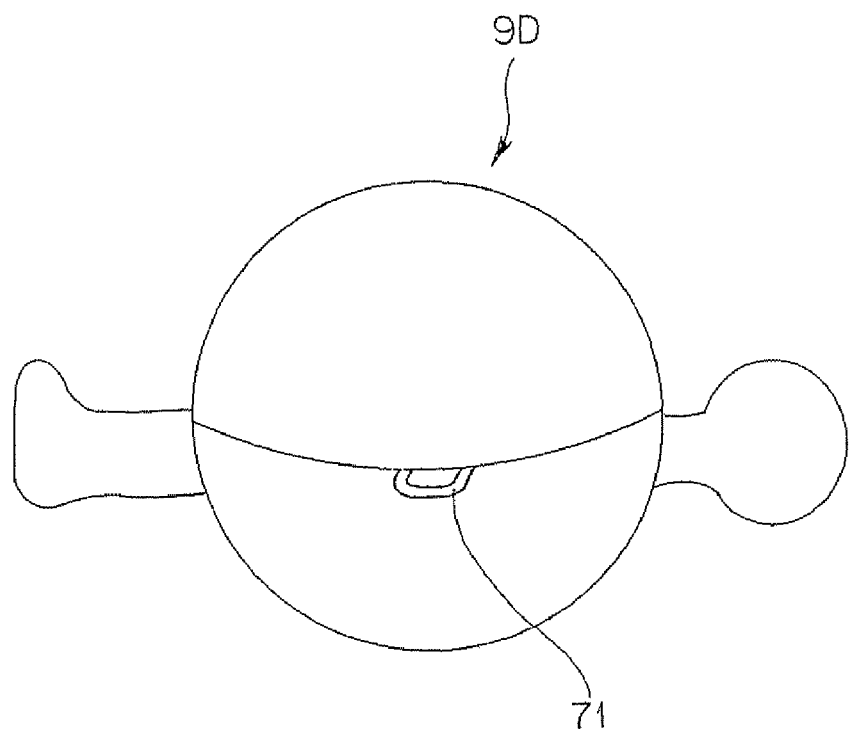
FIGS. 28A and 28B are explanatory diagrams schematically showing the position and posture detecting device shown in FIG. 8 according to the fifth modification.
Figure 28B:
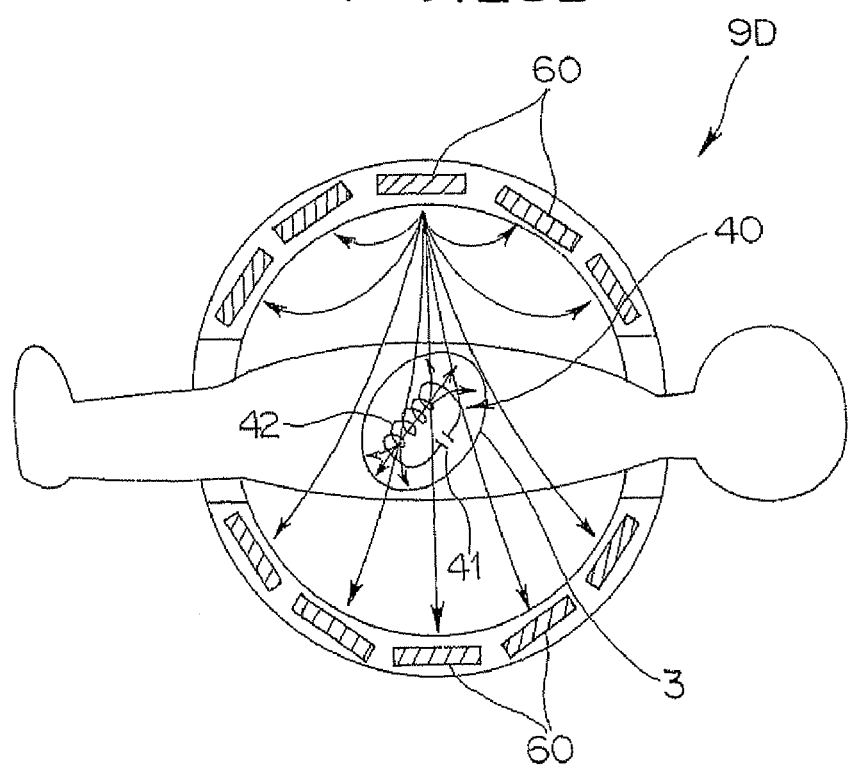

FIGS. 1 to 28B relate to a first embodiment of the present invention. FIG. 1 is a diagram showing the entire structure of a detecting system of the position and the posture of a capsule medical device according to the first embodiment, FIG. 2 is a circuit block diagram showing the detecting system of the position and the posture of the capsule medical device shown in FIG. 1, FIG. 3 is an explanatory diagram of the side of a capsule main body, FIG. 4 is a conceptual diagram showing an applied rotating magnetic field and the operation of the capsule main body that is caused by the rotating magnetic field, FIG. 5 is a conceptual diagram showing a vibrating magnetic field (magnetic field for generating a couple) applied to the rotating magnetic field shown in FIG. 4 and the operation of the capsule main body that is caused by the vibrating magnetic field (magnetic field for generating the couple), FIG. 6 is an explanatory diagram of the detection of position and posture of a position and posture detecting device to the capsule main body, FIG. 7 is an explanatory diagram showing the position and posture detecting device and a rotating magnetic field generating device, FIG. 8 is an enlarged perspective view showing the rotating magnetic field generating device and the position and posture detecting device shown in FIG. 7, FIG. 9 is a cutaway view showing the rotating magnetic field generating device and the position and posture detecting device shown in FIG. 8, FIG. 10 is a perspective view showing a position and posture detecting device shown in FIG. 8 according to a first modification, FIG. 11 is a cutaway view showing the rotating magnetic field generating device and the position and posture detecting device shown in FIG. 10, FIG. 12 is a perspective view showing the rotating magnetic field generating device and the position and posture detecting device shown in FIG. 8 according to a second modification, FIG. 13 is a schematic diagram showing the rotating magnetic field generating device which can be divided into two and the position and posture detecting device, FIG. 14 is a schematic diagram showing the rotating magnetic field generating device which can be opened/closed and the position and posture detecting device, FIGS. 15A and 15B are explanatory diagrams of examples of arrangement patterns of a detecting coil and an exciting coil arranged on a position and posture detecting substrate, FIG. 15A is a perspective view showing the example of the arrangement pattern of the detecting coil and the exciting coil arranged to the position and posture detecting substrate, FIG. 15B is a top view showing the position and posture detecting device and the rotating magnetic field generating device shown in FIG. 15A, FIGS. 16A to 16C are explanatory diagrams of other examples of the arrangement patterns of the detecting coil and the exciting coil arranged to the position and posture detecting substrate, FIG. 16A is a perspective view showing a first one of other examples of the arrangement pattern of the detecting coil and the exciting coil arranged to the position and posture detecting substrate, FIG. 16B is a perspective view showing a second one of other examples of the arrangement pattern of the detecting coil and the exciting coil arranged to the position and posture detecting substrate, FIG. 16C is a perspective view showing a third one of other examples of the arrangement pattern of the detecting coil and the exciting coil arranged to the position and posture detecting substrate, FIGS. 17A and 17B are explanatory diagrams schematically showing the rotating magnetic field generating device and the position and posture detecting device shown in FIG. 10, FIG. 17A is a perspective view schematically showing the appearance of the rotating magnetic field generating device and the position and posture detecting device shown in FIG. 10, FIG. 17B is a sectional view schematically showing the inner structure of the rotating magnetic field generating device and the position and posture detecting device shown in FIG. 17A, FIG. 18 is a perspective view schematically showing the appearance of the rotating magnetic field generating device and the position and posture detecting device shown in FIG. 12, FIGS. 19A and 19B are sectional views schematically showing the inner structure of the rotating magnetic field generating device and the position and posture detecting device shown in FIG. 18, FIG. 19A is a sectional view schematically showing the inner structure of the rotating magnetic field generating device and the position and posture detecting device shown in FIG. 18 in the direction of an arrow A, FIG. 19B is a sectional view schematically showing the inner structure of the rotating magnetic field generating device and the position and posture detecting device shown in FIG. 18 in the direction of an arrow B, FIG. 20 is a flowchart showing the operation for controlling the direction of the rotating magnetic field based on information on the direction and the position of the capsule main body detected by a direction/position detecting device, FIG. 21 is a circuit block diagram showing the direction/position detecting device shown in FIG. 2 according to the modification, FIG. 22 is a flowchart showing the operation for controlling the direction of the rotating magnetic field based on information on the direction and the position of the capsule main body detected by the direction/position detecting device shown in FIG. 21, FIG. 23 is a flowchart showing the control operation sequential to the flowchart shown in FIG. 20 or 21, FIGS. 24A to 24C are explanatory diagrams showing a coil forming a resonant circuit of a capsule main body according to a modification, FIG. 24A is an explanatory diagram of the side of the capsule main body in which the coil is wound to a covering member for covering components, FIG. 24B is an explanatory diagram of the cross-sectional shape of the covering member shown in FIG. 24A, FIG. 24C is an explanatory diagram of the side of the capsule main body in which the coil is wound to a stick member, FIGS. 25A to 25C are circuit block diagrams showing power supply circuits comprising the resonant circuit comprising the coils shown in FIGS. 24A to 24C, FIG. 25A is a circuit block diagram showing a first power-supply circuit, FIG. 25B is a circuit block diagram showing a second power-supply circuit, FIG. 25C is a circuit block diagram showing a third power-supply circuit, FIGS. 26A and 26B are explanatory diagrams schematically showing the rotating magnetic field generating device and the position and posture detecting device shown in FIG. 8 according to the third modification, FIG. 26A is a perspective view schematically showing the rotating magnetic field generating device and the position and posture detecting device shown in FIG. 8 according to the third modification, FIG. 26B is a sectional view schematically showing the inner structure of the rotating magnetic field generating device and the position and posture detecting device shown in FIG. 26A in the direction of an arrow A, FIG. 27 is a perspective view schematically showing the rotating magnetic field generating device and the position and posture detecting device shown in FIG. 8 according to a fourth modification, FIGS. 28A and 28B are explanatory diagrams schematically showing the position and posture detecting device shown in FIG. 8 according to a fifth modification, FIG. 28A is a perspective view schematically showing the position and posture detecting device shown in FIG. 8 according to the fifth modification, and FIG. 28B is a sectional view schematically showing the inner structure of the position and posture detecting device shown in FIG. 28A.

Figure 2:
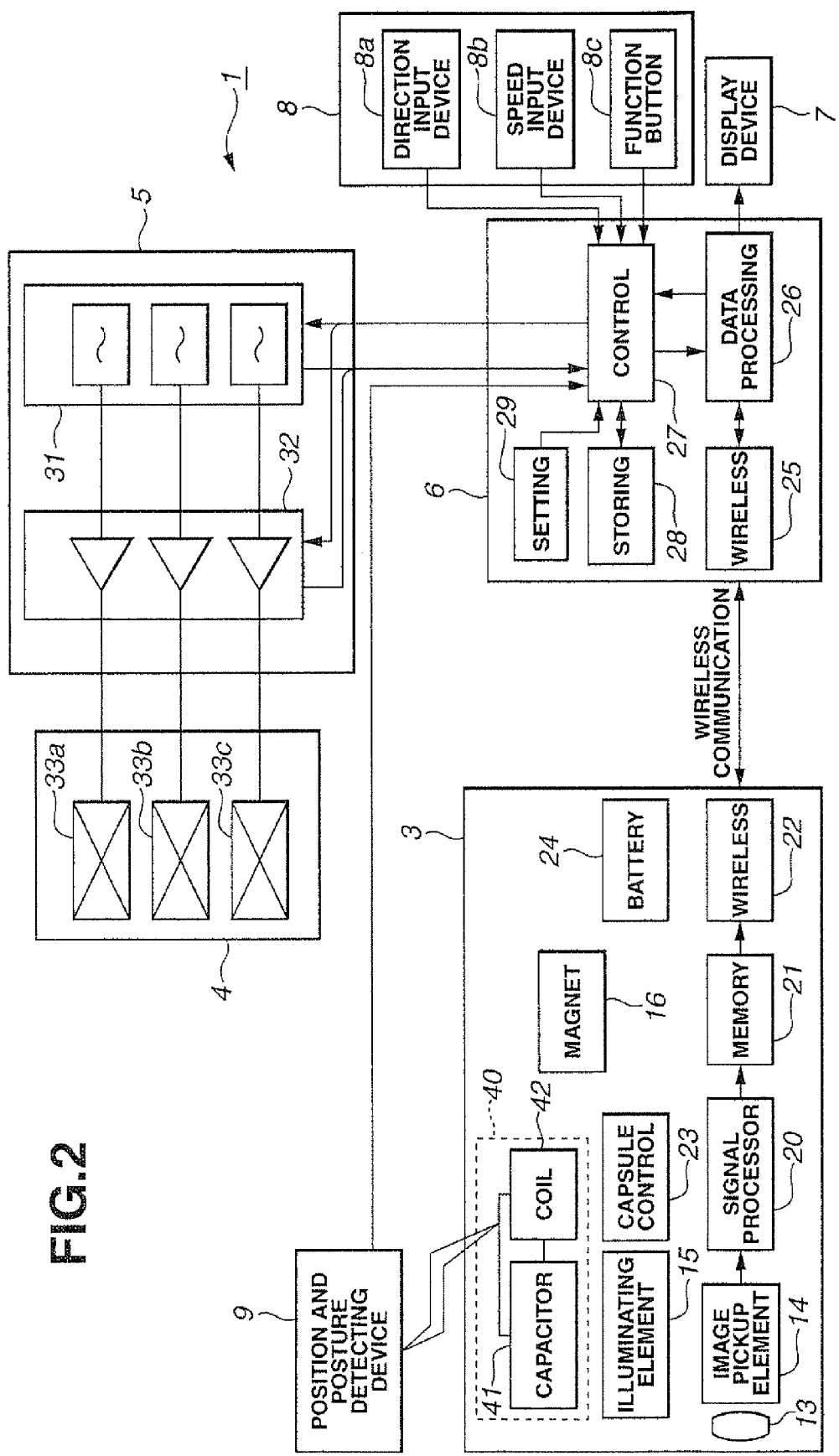
FIG. 2 is a circuit block diagram showing the detecting system of the position and the posture of the capsule medical device shown in FIG. 1.

Referring to FIGS. 1 and 2, a detecting system 1 of the position and the posture of a capsule medical device according to the first embodiment of the present invention comprises: a capsule medical device main body 3 (hereinafter, abbreviated to a capsule main body) which is inserted in the body cavity of a patient (not shown) and functions as a capsule endoscope for picking-up an image of the body cavity; a rotating magnetic field generating device 4, serving as a first magnetic-field generating device, which is arranged around the patient, namely, outside of the body and is a guiding device for extracorporeally guiding the direction and the position of the capsule main body 3 by applying a rotating magnetic field to the capsule main body 3; a magnetic field control device (or power control device) 5 which controls the supply of driving current for generating the rotating magnetic field in the rotating magnetic field generating device 4; a processing device 6 which is extracorporeally arranged to the patient, performs the wireless communication with the capsule main body 3, and controls the magnetic field control device 5 to control the direction and the level of the rotating magnetic field applied to the capsule main body 3; a display device 7 which is connected to the processing device 6 and displays the image picked-up by the capsule main body 3; and an operation input device 8 which is connected to the processing device 6 and inputs and instructs an instructing signal corresponding to the operation by the operation of an operator. The operation input device 8 comprises: a direction input device 8a which generates an instructing signal of the magnetic field direction; a speed input device 8b which generates an instructing signal of the rotating magnetic field of a rotating frequency corresponding to the operation; and a function button 8c which generates the instructing signal corresponding to a set function such as the generation of the rotating magnetic field deviated in accordance with the operation.

Further, the detecting system 1 of the position and the posture of the capsule medical device comprises a position and posture detecting device 9, serving as a magnetic field detecting unit, e.g., a magnetic sensor, that generates an Alternating magnetic field for generating induced electromotive force to a resonant circuit 40, which will be described later, included in the capsule main body 3, that detects the magnetic field generated by the resonant circuit 40 for generating the induced electromotive force by the Alternating magnetic field, and that detects the position and the direction of the capsule main body 3 in the longitudinal direction. The detailed structure of the position and posture detecting device 9 will be described later.

First, a description is given of the capsule main body 3.

Referring to FIG. 3, the capsule main body 3 comprises a spiral projection (or screw portion) 12, serving as a thrust generating structure portion which generates the thrust by the rotation of a capsule exterior container 11 onto the outer circumference. The inside of the capsule main body 3 sealed by the exterior container 11 accommodates an objective optical system 13, an image pickup element 14 arranged at the image forming position of the objective optical system 13, an illuminating element 15 for illuminating the light for image pickup operation, and a magnet 16.

The objective optical system 13 is arranged in a distal cover 11a which is semi-spherical and is transparent in the exterior container 11 so that the optical axis of the objective optical system 13 matches a central axis C of the cylindrical capsule main body 3, and the center portion of the distal cover 11a becomes an observing window 17. Although not shown in FIG. 3, the illuminating element 15 is arranged around the objective optical system 13.

In this case, the direction of the field of view of the objective optical system 13 is along the optical axis of the objective optical system 13, in other words, the central axis C of the cylindrical capsule main body 3.

The capsule main body 3 is accommodated in the exterior container 11 near the rear end thereof so that a coil 42 in the capsule forming the resonant circuit 40 is in a predetermined direction, specifically, the coil 42 in the capsule is solenoid-wound to and is set in the longitudinal direction of the capsule main body 3.

Further, the magnet 16 arranged in the center of the capsule main body 3 in the longitudinal direction has the N and S poles in the direction perpendicular to the central axis C. In this case, the center of the magnet 16 is arranged to match the gravity point of the capsule main body 3. In the case of externally applying the magnetic field, the center of magnetic force acting to the magnet 16 is at the gravity point of the capsule main body 3 so that the capsule main body 3 smoothly advances by the magnetic force. The magnet 16 is arranged to match a predetermined arranging direction of the image pickup element 14. That is, the up direction in the case of displaying the image picked-up by the image pickup element 14 is toward the N pole from the S pole of the magnet 16.

The rotating magnetic field generating device 4 applies the rotating magnetic field to the capsule main body 3, thereby magnetically rotating the magnet 16. The capsule main body 3 fixedly having the magnet 16 is rotated together with the capsule main body 3. The spiral projection 12 arranged onto the outer circumference of the capsule main body 3 comes into contact with the inner wall of the body cavity and is then rotated to thrust the capsule main body 3.

In the case of controlling the capsule main body 3 having the magnet 16 by the external magnetic field as mentioned above, it is known based on the direction of the external magnetic field which direction the up direction of the image picked-up by the capsule main body 3 is.

In addition to the objective optical system 13, the image pickup element 14, and the magnet 16, referring to FIG. 2, the capsule main body 3 accommodates therein: a signal processing circuit 20 which performs signal processing of the signal picked-up by the image pickup element 14; a memory 21 which temporarily stores a digital video signal created by the signal processing circuit 20; a wireless circuit 22 which modulates the video signal read from the memory 21 by a high-frequency signal, converts the modulated signal into a signal for radio transmission, and demodulates a control signal sent from the processing device 6; a capsule control circuit 23 which controls the signal processing circuit 20 in the capsule main body 3; and a battery 24 which supplies power for operation to an electronic system including the signal processing circuit 20 in the capsule main body 3.

Further, the capsule main body 3 comprises a capacitor 41 which is electronically connected to the coil 42 in the capsule. The capacitor 41 and the coil 42 in the capsule form the resonant circuit 40. When the position and posture detecting device 9 generates the Alternating magnetic field, the induced electromotive force is generated by the Alternating magnetic field to flow the current in the resonant circuit 40.

The coil 42 in the capsule has a specific self-resonant frequency. When the position and posture detecting device 9 generates the Alternating magnetic field approximate to the self-resonant frequency, the effective induced electromotive force is generated even without the capacitor 41 and the capacitor 41 is not necessary. Thus, the capacitor 41 is omitted and the structure is small and simple.

The processing device 6 for wireless communication with the capsule main body 3 comprises: a wireless circuit 25 which communicates data with the wireless circuit 22 by radio; a data processing circuit 26 which is connected to the wireless circuit 25 and performs data processing of the image display of image data sent from the capsule main body 3; a control circuit 27 which controls the data processing circuit 26 and the magnetic field control device 5; and a storing circuit 28 which stores information on the status of the rotating magnetic field generated by the rotating magnetic field generating device 4 via the magnetic field control device 5 and information on the setting of the direction input device 8a or the like.

The display device 7 is connected to the data processing circuit 26, thereby displaying the image which is picked-up by the image pickup element 14 and is processed by the data processing circuit 26 via the wireless circuits 22 and 25. The data processing circuit 26 corrects the direction of the image in a constant direction upon displaying the image on the display device 7 because the image is picked-up while rotating the capsule main body 3, and the data processing circuit 26 further performs the image processing so as to display the image which is easily viewed by the operator (for example, refer to the technology disclosed in Japanese Unexamined Patent Application Publication No. 2003-299612).

The control circuit 27 receives the instructing signal corresponding to the operation from the direction input device 8a and the speed input device 8b forming the operation input device 8, thereby controlling the operation in accordance with the instructing signal.

Further, the control circuit 27 is connected to the storing circuit 28, thereby continuously storing information on the direction (direction of the normal of the magnetic field rotating plane of the rotating magnetic field) of the rotating magnetic field generated by the rotating magnetic field generating device 4 via the magnetic field control device 5 and the direction of the magnetic field into the storing circuit 28. After that, even in the operation for changing the direction of the rotating magnetic field and the direction of the magnetic field, the direction of the rotating magnetic field and the direction of the magnetic field are continuously and smoothly changed. The storing circuit 28 may be arranged in the control circuit 27.

The magnetic field control device 5 connected to the control circuit 27 generates the AC current and comprises: an AC current generating and control unit 31 comprising three AC current generating and control circuits for controlling the frequency and the phase of the AC current; and a driver unit 32 comprising three drivers for amplifying the AC current. The output current from the three drivers are supplied to three electromagnets 33a to 33c forming the rotating magnetic field generating device 4.

In this case, the electromagnets 33a to 33c are arranged to generate the magnetic fields in the three perpendicular axial directions. For example, the electromagnets 33a to 33c are one set of facing coils, each having two coils, namely, three axial facing coils in the perpendicular magnetic field generating directions. Two Helmholtz coils serving as an example of the facing coils may be arranged to sandwich the patient.

According to the first embodiment, the rotating magnetic field generating device 4 has a Helmholtz coil 4A for generating the rotating magnetic field, serving as a coil for generating the rotating magnetic field that induces the capsule main body 3, which will be described later (refer to FIG. 7).

In the detecting system 1 of the position and the posture of the capsule medical device, the instructing signal of the magnetic field direction is generated by operating the direction input device 8a forming the operation input device 8, the instructing signal of the rotating magnetic field is generated with the rotating frequency corresponding to the operation of the speed input device 8b, and an (AC or periodic) vibrating magnetic field set by operating the function button 8c is generated. Thus, a couple is generated to the magnet 16 of the capsule main body 3 to rotate the central axis C around the central point of the central axis C of the capsule main body 3 in the longitudinal direction. In this case, since the vibrating magnetic field is applied in the AC manner or periodically so that the direction of the vibrating magnetic field (operated as the couple) is changed to the inverse direction before completely rotating the central axis C, the capsule main body 3 is inclined or is oscillated. The direction input device 8a inclines a joystick (not shown) in the desired advancing direction, thereby generating the rotating magnetic field to move the capsule main body 3 in the direction.

FIG. 4 shows the state of applying the rotating magnetic field. The magnet 16 included in the capsule main body 3 is rotated by applying the rotating magnetic field and the rotation advances or returns the capsule main body 3.

Referring to FIG. 4, the rotating magnetic field for changing the direction of the pole of the rotating magnetic field is applied on the rotating magnetic field plane vertical to the direction (y' in FIG. 4) or the central axis C of the capsule main body 3 in the longitudinal direction. Further, the capsule main body 3 and the magnet 16 fixed in the direction vertical to the longitudinal direction in the capsule main body 3 are rotated around the longitudinal direction. The capsule main body 3 is engaged with the inner wall of the body cavity in accordance with the rotating direction by the spiral projection 12 shown in FIG. 3, thereby advancing or returning.

FIG. 5 shows the state of applying the vibrating magnetic field (magnetic field for generating the couple) to the rotating magnetic field. The vibrating magnetic field (magnetic field for generating the couple) acting the magnet 16 to be oscillated (vibrated) around the direction (yz in FIG. 5) of the central axis C in the longitudinal direction is applied to the capsule main body 3.

Thus, when the capsule main body 3 is rotated around the central axis C thereof in the longitudinal direction and the direction of the central axis C of the rotation is deviated to be inclined. That is, the rotating torque of a rotating spinning top is reduced and the operation for vibrating the core by the operation of gravity (hereinafter, referred to as jiggling operation) is performed.

When the capsule main body 3 advances or returns in the longitudinal direction of the lumen therein with the same diameter as that of the capsule main body 3, the rotating magnetic field for rotating the capsule main body 3 around the longitudinal direction is applied to smoothly move the capsule main body 3.

On the contrary, when the lumen is bent and the capsule main body 3 comes into contact with the bending portion, and the capsule main body 3 is rotated around the longitudinal direction thereof, the capsule main body 3 is not smoothly moved in the bending direction.

In this case, the vibrating magnetic field is applied so that the force for rotating the central axis C is operated around the center of the capsule main body 3 along the central axis C of the longitudinal direction thereof and thus the capsule main body 3 is smoothly moved in the direction when the capsule main body 3 jiggles and the longitudinal direction in the jiggling operation is in the bending direction of the lumen.

By inclining the joystick, the status of the capsule main body 3 or the status of the rotating magnetic field is continuously grasped so that the direction of the rotating magnetic field is controlled in any desired arbitrary direction from the current advancing direction. According to the first embodiment, the status of the rotating magnetic field (specifically, the direction of the rotating magnetic field and the direction of the magnetic field) are continuously stored in the storing circuit 28.

Specifically, the instructing signal of the operation in the operation input device 8 shown in FIG. 2 is inputted to the control circuit 27. The control circuit 27 outputs, to the magnetic field control device 5, the control signal for generating the rotating magnetic field corresponding to the instructing signal, and stores the information on the direction of the rotating magnetic field and the direction of the magnetic field in the storing circuit 28.

The storing circuit 28 continuously stores information on the rotating magnetic field generated by the rotating magnetic field generating device 4 and on the direction of the magnetic field forming the rotating magnetic field, which periodically changes.

The storage of the storing circuit 28 is not limited to the storage of the information corresponding to the control signal of the direction of the rotating magnetic field and the direction of the magnetic field from the control circuit 27. The control signal outputted to the magnetic field control device 5 from the control circuit 27 may send, from the magnetic field control device 5 to the control circuit 27, information which determines the direction of the rotating magnetic field and the direction of the magnetic field that is actually outputted to the rotating magnetic field generating device 4 via the AC current generating and control unit 31 and the driver unit 32 in the magnetic field control device 5, and the sent information may be stored in the storing circuit 28.

According to the first embodiment, in the case of starting and stopping the operation for applying the rotating magnetic field and changing the direction of the rotating magnetic field (in other words, the direction of the capsule advancing direction, the rotating magnetic field is controlled to be continuously changed so that the force in this case smoothly operates the capsule main body 3 without any operation of sharp force.

According to the first embodiment, the rotation of the capsule main body 3 rotates the image picked-up by the image pickup element 14. Thus, when the image is displayed on the display device 7 as it is, the display image is rotated. Then, the operability of the instructing operation in the desired direction of the speed input device 8b is deteriorated and therefore, preferably, the rotation of display image stops.

According to the first embodiment, as disclosed in Japanese Unexamined Patent Application Publication No. 2003-299612, the data processing circuit 26 and the control circuit 27 correct the image obtained by stopping the rotation of the rotated image.

The image may be rotated based on the information on the direction of the magnetic field, the rotation of the capsule main body 3 may be canceled, and the image may be displayed (or, a still image in the predetermined direction may be displayed by correlation processing of image).

Referring to FIG. 6, the position and posture detecting device 9 comprises: an exciting coil array 51, serving as second magnetic-field generating means, which generates the Alternating magnetic field for generating the induced electromotive force to the resonant circuit 40 of the capsule main body 3; and a detecting coil array 52, serving as magnetic field detecting means, which detects the magnetic field generated by the resonant circuit 40 in the capsule main body 3, the direction of the capsule main body 3 in the longitudinal direction, and the position of the capsule main body 3.

The exciting coil array 51 and the detecting coil array 52 are one set. According to the first embodiment, three sets of the exciting coil array 51 and the detecting coil array 52 are arranged to generate the magnetic fields in the three perpendicular axial directions. That is, the exciting coil array 51 and the detecting coil array 52 are one set and the three sets thereof are in the perpendicular generating directions and detecting directions.

The position and posture detecting device 9 comprises: a signal measuring instrument 53 which measures the signal detected by the detecting coil array 52; a calculation processing unit 54 which calculates the direction of the capsule main body 3 in the longitudinal direction and the position thereof based on the data measured by the signal measuring instrument 53; and an oscillator 55 which oscillates the exciting coil array 51 with a predetermined oscillating frequency of, e.g., 1 kHz to 1 MHz so as to generate the Alternating magnetic field for mutually inducing the resonant circuit 40.

A measurement magnetic field $B_{total}$ (vector) detected by the detecting coil array 52 is obtained by using an applying magnetic field $B_{ext}$ (vector) generated by the exciting coil array 51 and a magnetic field $B_{reso}$ (vector) generated by the resonant circuit 40. That is, $$\vec{B}_{total} = \vec{B}_{ext} + \vec{B}_{reso} \quad \text{(Formula 1)}$$

The magnetic field $B_{reso}$ generated by the resonant circuit 40 is described on the three-dimensional coordinate (not shown) as a function of the position and direction of the resonant circuit 40 as follows.

$$\vec{B}_{reso}(x_0, y_0, z_0, \theta, \phi, M) = \frac{1}{4\pi\mu}\left(-\frac{\vec{M}}{r^3} + \frac{3(\vec{M}\cdot\vec{r})\cdot\vec{r}}{r^5}\right). \quad \text{(Formula 2)}$$

where $x_0$: x coordinate of capsule main body 3,
$y_0$: y coordinate of capsule main body 3,
$z_0$: z coordinate of capsule main body 3,
$\theta$: angle of capsule main body 3 to the z axis,
$\phi$: angle of capsule main body 3 to the y axis,
r: distance from resonant circuit 40 to detecting coil array 52, and
M: strength of equivalent magnetic moment generated by resonant circuit 40.

That is, the calculation processing unit 54 subtracts the exciting magnetic field $B_{ext}$ generated by the exciting coil array 51 from the measurement magnetic field $B_{total}$ detected by the detecting coil array 52 to obtain the magnetic field $B_{reso}$ generated by the resonant circuit 40, and calculates, from the resultant value, the position (x, y, z) of the capsule main body 3, the direction (θ, φ) of the capsule main body 3, and an equivalent magnetic moment M.

The frequency of the magnetic induction by the rotating magnetic field generated by the Helmholtz coil 4A for generating the rotating magnetic field is up to 10 Hz so as to physically move the capsule main body 3. Meanwhile, the frequency of the mutual induction by the resonance of the resonant circuit 40 is up to 1 kHz to 1 MHz in consideration of the absorption in the living body as mentioned above. Therefore, the magnetic induction of the rotating magnetic field does not mutually influence on the mutual induction of the resonance by the resonant circuit 40.

The detecting coil array 52 and the exciting coil array 51 are incorporated in the rotating magnetic field generating device 4 as shown in FIGS. 7 to 9.

Referring to FIGS. 7 to 9, in the exciting coil array 51 and the detecting coil array 52, an exciting coil 62 and a plurality of detecting coils 61 are uniformly arranged, facing four surfaces excluding the opening corresponding to the head and the foot so as to insert the patient body. Specifically, the direction of the normal of the surface serving as the opening of a cubical frame is the same as a part of the detecting direction of the detecting coils 61, and the plurality of detecting coils 61 are arranged onto the surfaces other than the surface serving as the opening and the surface opposite to the opening.

By setting surfaces in front of the exciting coil array 51 and the detecting coil array 52 to the exciting surfaces, the surfaces opposite to the set surfaces of the exciting coil array 51 and the detecting coil array 52 are shared as the detecting ones. As mentioned above, one set of the exciting coil array 51 and the detecting coil array 52 is set and the three sets are arranged to generate the magnetic field in the three-axial perpendicular directions. Since one set of the exciting coil array 51 and the detecting coil array 52 is not arranged to the head and the foot, the exciting coil 62 and the detecting coils 61 in the different directions by an angle of 90° are distributed to other four surfaces.

The exciting coil is cubically shaped similarly to the rotating magnetic field generating device 4, and the three sets of exciting coils 62 (preferably, Helmholtz) are arranged so as to uniformly generate the Alternating magnetic field in the perpendicular magnetic-field generating directions.

Thus, the position and posture detecting device 9 uniformly generates the Alternating magnetic field and therefore the induced electromotive force is finely generated in the resonant circuit 40 and the detecting coil array 52 detects the magnetic field of the resonant circuit 40 with high precision.

The detecting coils 61 and the exciting coil 62 are arranged on the position and posture detecting substrate (refer to FIGS. 15A, 15B, 16A, 16B, and 16C), and however the position and posture detecting substrate is omitted for the purpose of easy understanding.

Two sets of exciting coil array 51 and the detecting coil array 52 may be arranged like a peak at a predetermined angle to generate the magnetic fields in the three-axial perpendicular directions as shown in FIGS. 10 and 11. Referring to FIGS. 10 and 11, the detecting coils 61 and the exciting coil 62 are arranged on the position and posture detecting substrate (refer to FIGS. 15A, 15B, 16A, 16B, and 16C). However, the position and posture detecting substrate is omitted for the purpose of easy understanding. Referring to FIGS. 17A and 17B, the position and posture detecting substrate 60 having the detecting coils 61 and the exciting coil 62 is attached to the rotating magnetic field generating device 4 serving as a frame casing, having an opening for insertion of the living body. The casing is a polygonal member, here, substantially a cubical member.

Referring to FIG. 12, the exciting coil 62 may be arranged to the four surfaces excluding the patient's head and foot. As shown in FIG. 12, the direction of magnetic field of at least one of exciting coils 63 is different from the magnetic fields of other exciting coils 63. Similarly, the detecting direction of at least one of detecting coils 61 is different from the detecting direction of other detecting coils 61. Preferably, the exciting coil 62 is the Helmholtz one. As shown in FIG. 12, the detecting coils 61 and the exciting coils 63 are arranged onto the position and posture detecting substrate (refer to FIGS. 15A, 15B, 16A, 16B, and 16C). However, the position and posture detecting substrate is omitted for the purpose of easy understanding.

As compared with the arrangement of the position and posture detecting substrate to the three axes including the patient's head and foot, the position and posture detecting substrate shown in FIG. 12 is arranged to the two axes excluding the patient's head and foot. Therefore, the detecting sensitivity is deteriorated, but the simple structure is easily realized.

The position and posture detecting substrate 60 having the exciting coil 62, the detecting coils 61, and the exciting coils 63 is attached to the rotating magnetic field generating device 4 serving as a frame as shown in FIGS. 18, 19A, and 19B.

The above-structured position and posture detecting device 9 inputs the direction and the position information of the capsule main body 3 calculated by the calculation processing unit 54 to the control circuit 27 in the processing device 6.

The control circuit 27 controls the operation for generating the rotating magnetic field and the direction of the generated rotating magnetic field based on the information stored in the storing circuit 28 and the information detected by the position and posture detecting device 9 upon operating the operation input device 8.

Referring to FIG. 13, the rotating magnetic field generating device 4 and the position and posture detecting device 9 incorporated in the rotating magnetic field generating device 4 may be divided into two to easily insert the patient body. Alternatively, referring to FIG. 14, the rotating magnetic field generating device 4 and the position and posture detecting device 9 incorporated in the rotating magnetic field generating device 4 may be opened/closed. Or, the rotating magnetic field generating device 4 and the position and posture detecting device 9 may individually be structured.

In the position and posture detecting device 9, the exciting coil 62 and the detecting coils 61 are arranged on the same plane of the position and posture detecting substrate 60 as shown in FIGS. 15A, 15B, 16A, 16B, and 16C. Referring to FIGS. 15A and 15B, on the position and posture detecting substrate 60, the detecting coils 61 are uniformly and horizontally arranged to the exciting coil 62 at the same interval on the same plane on the sheet-shaped base containing a non-magnetic member, and the detecting coils 61 corresponding to the head and foot are uniformly and vertically arranged a the same interval to structure a unit. The detecting coils 61 partly have the different detecting directions. Specifically, at least three detecting coils 61 have the perpendicular detecting directions to one another. Referring to FIG. 15A, the exciting coil 62 and at least one detecting coil 61 are arranged substantially on the same place, and the direction of magnetic field of the exciting coil 62 is substantially the same as the detecting direction of at least one detecting coil 61.

On the other hand, referring to FIG. 16A, on the position and posture detecting substrate 60, the exciting coil 62 and the detecting coils 61 are arranged in parallel on the same plane. As shown in FIG. 16B, on the position and posture detecting substrate 60, the detecting coils 61 are arranged in the exciting coil 62 on the same plane. Referring to FIG. 16B, the symmetric central axis of the exciting coil 62 with the symmetric shape arranged on the position and posture detecting substrate 60 serving as the base and the symmetric central axis of the detecting coils 61 with the symmetric shape are coaxially arranged. The position and posture detecting substrate 60 has one detecting coil 61. Referring to FIG. 16C, the position and posture detecting substrate 60 uniformly has the detecting coils 61 around the exciting coil 62, in addition to the structure shown in FIG. 16B. The plurality of detecting coils 61 have substantially the same detecting direction.

As described with reference to FIGS. 15A and 15B and FIGS. 16A to 16C, the position and posture detecting substrate 60 is varied on the same plane. Thus, the position and posture detecting device 9 effectively generates the Alternating magnetic field for generating the induced electromagnetic force to the resonant circuit 40 of the capsule main body 3 and further effectively detects the magnetic field generated by the resonant circuit 40 of the capsule main body 3.

Preferably, the position and posture detecting device 9 has the exciting coil 62 with the Helmholtz structure when two position and posture detecting substrates 60 face each other.

The operation with the above-mentioned structure will be described according to the first embodiment.

In the examination of the body cavity by using the capsule main body 3, the patient swallows the capsule main body 3. When the capsule main body 3 inserted in the body cavity passes through the esophagus, the illuminating element 15 illuminates the esophagus and the image picked-up by the image pickup element 14 is sent by radio to the extracorporeal processing device 6 via the wireless circuit 22.

The processing device 6 stores the image data, which is received by the wireless circuit 25 and is demodulated, in an image storing device (such as a hard disk) arranged in the data processing circuit 26 or the like, performs the display processing, outputs the image to the display device 7, and displays the images that are sequentially picked-up by the capsule main body 3.

The control circuit 27 in the processing device 6 controls the operation for generating the rotating magnetic field and the direction of the generated rotating magnetic field based on the direction and the position information of the capsule main body 3 detected by the position and posture detecting device 9. FIG. 20 is a flowchart showing the operation for controlling the direction of the rotating magnetic field based on the direction and the position information of the capsule main body detected by the position and posture detecting device. The operation will be described with reference to FIG. 20.

First, the control circuit 27 measures the direction and the position of the capsule main body 3 by controlling and driving the position and posture detecting device 9 (in steps S1 and S2). According to the first embodiment, the exciting coil 62 is used as the exciting coil array 51 and the detecting coils 61 are used as the detecting coil array 52.

The position and posture detecting device 9 allows the oscillator 55 to oscillate the exciting coil array 51 (exciting coil 62) by a predetermined oscillating frequency of, e.g., 1 kHz to 1 MHz to generate the Alternating magnetic field.

The resonant circuit 40 of the capsule main body 3 generates the induced electromotive force by the mutual induction of the Alternating magnetic field, flows the current to the coil 42 in the capsule, and generates the magnetic field. The magnetic field from the resonant circuit 40 is detected by the detecting coil array 52 (detecting coils 61). The measured value detected by the detecting coil array 52 (detecting coils 61) is captured by the signal measuring instrument 53 and is inputted to the calculation processing unit 54.

The calculation processing unit 54 calculates the position and the direction of the resonant circuit 40 from the above-mentioned formulae 1 and 2 based on the input measured value, and outputs, to the control circuit 27, the calculating result as data on the position and direction of the capsule main body 3.

The control circuit 27 sets the direction of the rotating magnetic field based on the data on the direction and the position of the capsule main body 3 inputted from the 9, and controls and drives the rotating magnetic field generating device 4 to generate the rotating magnetic field in the set direction.

Further, the control circuit 27 controls and drives the rotating magnetic field generating device 4 to controls the capsule main body 3 to be in the desired direction and at the desired position in accordance with the input of the operation input device 8 operated by the operator, e.g., the joystick of the direction input device 8a.

That is, the control circuit 27 detects the input of the operation input device 8 (joystick) (in step S3). When the control circuit 27 determines that the operation is inputted (YES in step S4), the control circuit 27 calculates a generating condition of the next rotating magnetic field generated by the rotating magnetic field generating device 4 so as to control the capsule main body 3 to be in the desired direction and at the desired position in accordance with the operation of the operation input device 8 (in step S5), and generates (adds) the rotating magnetic field (in step S6). When the control circuit 27 determines that the operation is not inputted by the operation input device 8 (joystick), the control circuit 27 maintains the status of the set rotating magnetic field until the operation is inputted.

The capsule main body 3 changes the direction and the position thereof in accordance with the generated rotating magnetic field. In the capsule main body 3, the degree of change of the direction varies, e.g., the capsule main body 3 excessively moves or hardly moves in accordance with the operation of the operation input device 8 depending on the status of the lumen, e.g., the existence of the body fluid or wall or the area of the organ, and such an error that the capsule main body 3 is not in the calculated direction thereof is caused.

The mutual induction of the resonant circuit 40 of the capsule main body 3 becomes maximum when the central axis of the position and posture detecting substrate 60 having the exciting coil array 51 (exciting coil 62) and the central axis of the position and posture detecting substrate 60 having the detecting coil array 52 (detecting coils 61) match the axis of the coil 42 in the capsule. As the amount of changing position and the amount of changing angle are increased, the magnetic field generated by the coil 42 in the capsule is reduced and thus the position is not detected with precision.

Further, the strength of the magnetic field generated by the coil 42 in the capsule is reduced in proportion to the third power of distance. Therefore, in order to increase the detecting precision, the space needs to be reduced at the necessary and minimum level. In the detection of the human body, the capsule main body 3 needs to be arranged to surround only the target portion.

In the cubical coil, at least two-surface exciting coil array 51 (exciting coil 62) from among the six surfaces and the detecting coil array 52 (detecting coils 61) need the arrangement of coil to prevent the increase in cubical size while maintaining the three-axial arrangement for interference with the human body.

According to the first embodiment, the exciting coil array 51 (exciting coil 62) and the detecting coil array 52 (detecting coils 61) are arranged to the rotating magnetic field generating device 4 (Helmholtz coil 4A for generating the rotating magnetic field) so that the plurality of exciting coils 62 and the detecting coils 61 are uniformly arranged to the four surface excluding the head and foot, facing each other, so that the patient body enters.

Further, according to the first embodiment, the resonant frequency of the Alternating magnetic field generated by the exciting coil 62 or the exciting coils 62 and 63 is oscillated by 1 kHz to 1 MHz. Therefore, the frequency is different from the driving frequency of the rotating magnetic field generated by the rotating magnetic field generating device 4 (Helmholtz coil 4A for generating the rotating magnetic field), therefore no mutual interference (mutual influence) is caused.

According to the first embodiment, the direction and the position of the capsule main body 3 are precisely detected without the influence on the rotating magnetic field for magnetically inducing the capsule main body 3.

Then, the control circuit 27 measures again the direction and the position of the capsule main body 3, and controls the following operation to correct the error.

That is, the control circuit 27 controls and drives the position and posture detecting device 9 again to measure the data on the direction and the position of the capsule main body 3 (in step S7).

The control circuit 27 compares the data on the direction of the capsule main body 3 obtained from the position and posture detecting device 9 with the data on the direction of the rotating magnetic field (direction of the normal of the magnetic-field rotating plane of the rotating magnetic field) generated by the rotating magnetic field generating device 4 (in step S8). Then, the control circuit 27 determines whether or not the comparing result is larger than a preset value α (in step S9).

When the comparing result between the data on the direction of the capsule main body 3 obtained by the position and posture detecting device 9 and the data on the direction of the rotating magnetic field generated by the rotating magnetic field generating device 4 is larger than the set value α, the control circuit 27 sets the direction of the rotating magnetic field as the data on the measured direction of the capsule main body 3 (in step S10), then detects the input of the operation input device 8 (joystick), and repeats the above operation.

As a consequence, the detecting system 1 of the position and the posture of the capsule medical device precisely detects the direction and the position of the capsule main body 3 without any influence to the rotating magnetic field for magnetically inducing the capsule main body 3.

That is, the detecting system 1 of the position and the posture of the capsule medical device updates the data on the direction of the capsule main body 3 upon every operation of the operation input device 8 and therefore the error due to the state of the lumen by the operation of the operation input device 8 is not caused. Thus, the detecting system 1 of the position and the posture of the capsule medical device according to the first embodiment smoothly operates the capsule main body 3 by the magnetic induction.

The detecting system 1 of the position and the posture of the capsule medical device may be structured as shown in FIGS. 21 and 22. FIG. 21 is a circuit block diagram showing the position and posture detecting device shown in FIG. 2 according to the modification. FIG. 22 is a flowchart showing the operation for controlling the direction of the rotating magnetic field based on the information on the direction and position of the capsule main body detected by the position and posture detecting device shown in FIG. 21.

As shown in FIG. 21, a magnetic field control device 5B comprises: a direction calculating unit 71 which calculates the direction of the capsule main body 3 based on the data on the direction of the rotating magnetic field generated by the rotating magnetic field generating device 4; and a feedback factor adjusting unit 72 which adjusts the AC current generated by the AC current generating and control unit 31 based on the feedback factor calculated by the control circuit 27.

The control circuit 27 generates the rotating magnetic field based on the information on the direction and position of the capsule main body 3 detected by the position and posture detecting device 9 in accordance with the flowchart shown in FIG. 22, and controls the direction of the generated rotating magnetic field. In the flowchart shown in FIG. 22, the processing routine to step S14 whereupon the input of the operation input device 8 is detected is the same as the operation from steps S1 to S4 in the flowchart according to the first embodiment, and a description thereof is omitted.

According to a modification, three sets of facing coils (Helmholtz coils) 33a to 33c of the rotating magnetic field generating device 4 generate the rotating magnetic field, and exciting facing coils (Helmholtz coils) 62a to 62c apply the Alternating magnetic field for generating the induced electromotive force to the coil 42 in the capsule. Detecting coil arrays 52a to 52c detect the magnetic field generated by the current flowed by the induced electromagnetic force of the coil 42 in the capsule.

When it is determined that the operation input device 8 (joystick) inputs the operation (in step S14), the control circuit 27 calculates a generating condition of the next rotating magnetic field generated by the rotating magnetic field generating device 4 in accordance with the operation of the operation input device 8 so as to control the capsule main body 3 to be in the desired direction and at the desired position (in step S15). Further, the control circuit 27 generates (adds) the rotating magnetic field (in step S16).

The capsule main body 3 changes the direction and the position in accordance with the generated rotating magnetic field. In the capsule main body 3, the degree of change of the direction varies, e.g., the capsule main body 3 excessively moves or hardly moves in accordance with the operation of the operation input device 8 depending on the status of the lumen, e.g., the existence of the body fluid or wall or the area of the organ, and such an error that the capsule main body 3 is not in the calculated direction thereof is caused.

Then, the control circuit 27 measures again the direction and the position of the capsule main body 3 and controls the following operation for correcting the error.

First, the control circuit 27 controls and drives again the position and posture detecting device 9 to measure the data on the direction and the position of the capsule main body 3 and detect the direction of the capsule main body 3 (in step S17).

Next, the control circuit 27 controls the direction calculating unit 71 to compare the data on the direction of the rotating magnetic field generated by the rotating magnetic field generating device 4 with the data on the direction and position of the capsule main body 3. The control circuit 27 calculates the differential ($\Delta\theta$, $\Delta\phi$) between the data on the direction of the rotating magnetic field obtained by the direction calculating unit 71 and the data on the direction of the capsule main body 3 obtained by the position and posture detecting device 9 (in step S18).

Next, the control circuit 27 detects the input of the operation input device 8 (joystick) (in step S19), and calculates the amount (θ', φ') of changing direction of the capsule main body 3 in accordance with the operation of the operation input device 8 (in step S20).

Then, the control circuit 27 subtracts the differential (Δθ, Δφ) to which the feedback factor A is multiplied from the calculated amount (θ', φ') of changing direction of the capsule main body 3, and calculates the amount of changing direction (amount of instructions on the change) of the capsule main body 3 in accordance with the operation input device 8 (in step S21).

The amount (θ, φ) of instructions on the change of the capsule main body 3 in accordance with the operation of the operation input device 8 is calculated as follows.

$$(\theta, \phi) = (\theta' - A\Delta\theta, \phi' - A\Delta\phi)$$

where A=feedback factor.

Next, the control circuit 27 calculates a generating condition of the next rotating magnetic field generated by the rotating magnetic field generating device 4 in the direction corresponding to the operation of the operation input device 8 based on the calculated amount (θ, φ) of instructions on the change of the capsule main body 3 (in step S22).

The control circuit 27 generates (adds) the rotating magnetic field based on the calculated generating condition of rotating magnetic field (in step S16), and repeats the same operation.

As a result, the detecting system 1 of the position and the posture of the capsule medical device according to the modification more stably controls the operation of the capsule main body 3, as compared with the first embodiment.

In the flowchart shown in FIG. 22, the feedback factor A is preset to a predetermined value. However, the control operation may be performed to vary the feedback factor A.

Under the control operation described with reference to the flowchart shown in FIG. 20 or 22, three directions, namely, the direction of the coil 42 in the capsule of the capsule main body 3, the directions of the exciting facing coils (Helmholtz coils) 62a to 62c of the position and posture detecting device 9, and the directions of the detecting coil arrays 52a to 52c match each other and then the direction/position is detected with high precision. However, the effect of angle of the capsule main body 3 becomes large, the precision of the direction/position detection deteriorates.

Therefore, the control in the flowchart shown in FIG. 23 is added to the control operation described in the flowchart shown in FIG. 22 so as to keep the high precision of the direction/position detection. FIG. 23 is a flowchart showing the control operation added to the flowchart shown in FIG. 20 or 22. That is, as shown in FIG. 23, the control circuit 27 first inputs and sets the direction of the Alternating magnetic field generated by the exciting facing coils (Helmholtz coils) 62a to 62c of the position and posture detecting device 9 as the predetermined direction of the capsule main body 3 serving as the initial value (in steps S31 and S32), and controls and drives the position and posture detecting device 9 to detect the position/direction (in step S33).

Next, the control circuit 27 calculates an angle β formed by the direction of the Alternating magnetic field generated by the exciting facing coils (Helmholtz coils) 62a to 62c and the calculated direction of the capsule main body 3 (in step S34).

The control circuit 27 compares the calculated angle β with a threshold angle $\beta_0$ (e.g., 30° or 45°) (in step S35). When the calculated angle β is over the threshold angle $\beta_0$, the control circuit 27 sets the direction of the Alternating magnetic fields generated by the exciting facing coils (Helmholtz coils) 62a to 62c as the direction of the capsule main body 3 based on the calculated angle β (in step S36). After that, the processing from steps S33 to S36 is repeated.

The control operation is added and, consequently, in the detecting system 1 of the position and the posture of the capsule medical device, the direction of the coil 42 in the capsule of the 3 and the directions of the Alternating magnetic fields generated by the exciting facing coils (Helmholtz coils) 62a to 62c of the position and posture detecting device 9 substantially match each other. Thus, the three directions, that is, the direction of direction of the coil 42 in the capsule of the capsule main body 3, the directions of the exciting facing coils (Helmholtz coils) 62a to 62c of the position and posture detecting device 9, and the directions of the detecting coil arrays 52a to 52c substantially match each other, so the direction and the posture are detected with high precision.

Further, the Helmholtz coil 62 comprises the three Helmholtz coils 62a to 62c so as to generate the magnetic fields in the three axial directions. Therefore, the direction of the Alternating magnetic field can arbitrarily be set.

The coil 42 in the capsule forming the resonant circuit 40 of the capsule main body 3 may be structured as shown in FIGS. 24A to 24C. FIGS. 24A to 24C are explanatory diagrams of a capsule main body having a coil forming the resonant circuit according to the modification. FIG. 24A is a side explanatory diagram of the capsule main body in which the coil is wound to a covering member for covering the included component. FIG. 24B is an explanatory diagram of the cross-sectional shape of the covering member shown in FIG. 24A. FIG. 24C is a side explanatory diagram of the capsule main body in which the coil is wound to a stick member.

As shown in FIGS. 24A and 24B, a covering member 81 for covering the included component of the capsule main body 3 winds the coil 42 in the capsule, and the outer circumference of the coil 42 in the capsule is coated with a resin material. The covering member 81 contains a foil with high magnetic-permeability serving as a member with high magnetic-permeability, e.g., permalloy, nickel, or iron, and is arcuately shaped to prevent the eddy current.

As shown in FIG. 24C, the coil 42 in the capsule may be wound to a stick member 82 containing a member with high magnetic-permeability, e.g., permalloy, nickel, or iron. The spiral projection (or screw portion) 12 is omitted in FIGS. 24A to 24C.

In the capsule main body 3, the magnetic field generated by the resonant circuit 40 comprising the coil 42 in the capsule is strengthened, and the precision of the detection of direction and position of the position and posture detecting device 9 is increased.

Further, the resonant circuit 40 comprising the coil 42 in the capsule may form a power supply circuit to supply the power as shown in FIGS. 25A to 25C. FIGS. 25A to 25C are circuit block diagrams showing the power supply circuit comprising the resonant circuit comprising the coils shown in FIGS. 24A to 24C. FIG. 25A is a circuit block diagram showing a first power-supply circuit. FIG. 25B is a circuit block diagram showing a second power-supply circuit. FIG. 25C is a circuit block diagram showing a third power-supply circuit.

A power supply circuit 90A shown in FIG. 25A comprises two change-over switches 91 at both ends of the coil 42 in the capsule. Further, in the power supply circuit 90A, the capacitor 41 is connected to a terminal a, and a power supply circuit 92 is connected to a terminal b. One end of the output of the power supply circuit 92 is connected to the circuits in the capsule, and the other end thereof is connected to a secondary battery or a super-capacitor.

The control circuit 27 controls the switching operation of the change-over switches. In the detection of direction and position of the position and posture detecting device 9, the terminal is switched to the terminal a to form the resonant circuit 40. In the case of supplying the power, the terminal is switched to the terminal b to connect the power supply circuit 92.

In a power supply circuit 90B shown in FIG. 25B, the resonant circuit 40 and the power supply circuit 92 are connected to the power supply circuit 90A by a transfer 93. Thus, as compared with the power supply circuit 90A, the influence from the power supply is suppressed for the detection of direction and position of the position and posture detecting device 9 in the power supply circuit 90B.

In a power supply circuit 90C shown in FIG. 25C, the resonant circuit 40 and the power supply circuit 92 are connected to the power supply circuit 903 via two change-over switches 94. With the above-mentioned power supply circuits, the power is supplied to the capsule main body 3.

The position and posture detecting device may be structured as shown in FIGS. 26A and 26B.

As shown in FIGS. 26A and 26B, a position and posture detecting device 9B has the position and posture detecting substrate 60 corresponding to the foot, which is movable and diagonally opened. Further, the position and posture detecting substrate 60 corresponding to the head has a hole portion in which the head is inserted. The position and posture detecting substrate 60 may be attached/detached to/from a frame.

Thus, the position and posture detecting device 9B effectively detects the direction and position of the capsule main body 3 even at the periphery portion of the head and foot.

As shown in FIG. 27, the position and posture detecting device may be regularly octahedral. Referring to FIG. 27, in a position and posture detecting device 9C, the position and posture detecting substrate 60 is attached to a regularly octahedral frame, serving as a casing, having an opening into which the living body is inserted. Thus, the position and posture detecting device 9C effectively detects the direction and position of the capsule main body 3 even at the periphery portion of the head and foot.

As shown in FIGS. 28A and 28B, the position and posture detecting device may be spherical.

Referring to FIGS. 28A and 28B, in a position and posture detecting device 9D, the position and posture detecting substrate 60 is attached to a regularly octahedral frame, serving as a casing, having an opening into which the living body is inserted. Thus, in the position and posture detecting device 9D, the position and posture detecting substrate 60 is spherically arranged, and so the axis matching that of the coil 42 in the capsule is provided, irrespective of the direction and position of the capsule main body 3. Thus, the detecting precision is improved.

In the case of combining, to the position and posture detecting devices 9C and 9D, the rotating magnetic field generating device 4 for magnetically inducing the capsule main body 3, the rotating magnetic field generating device 4 is arranged to the outside. In this case, as the combined rotating magnetic field generating device 4, a cubical Helmholtz coil 4A for generating the rotating magnetic field is arranged to the outside (not shown).

The position and posture detecting devices 9C and 9D can be opened so that the body of the patient is easily inserted, and a handle 71 is arranged to the position and posture detecting devices 9C and 9D. As compared with the spherical position and posture detecting device 9D, the position and posture detecting device 9C does not have the spherical position and posture detecting substrate 60. Thus, the productivity is improved.

Second Embodiment

Figure 29A:
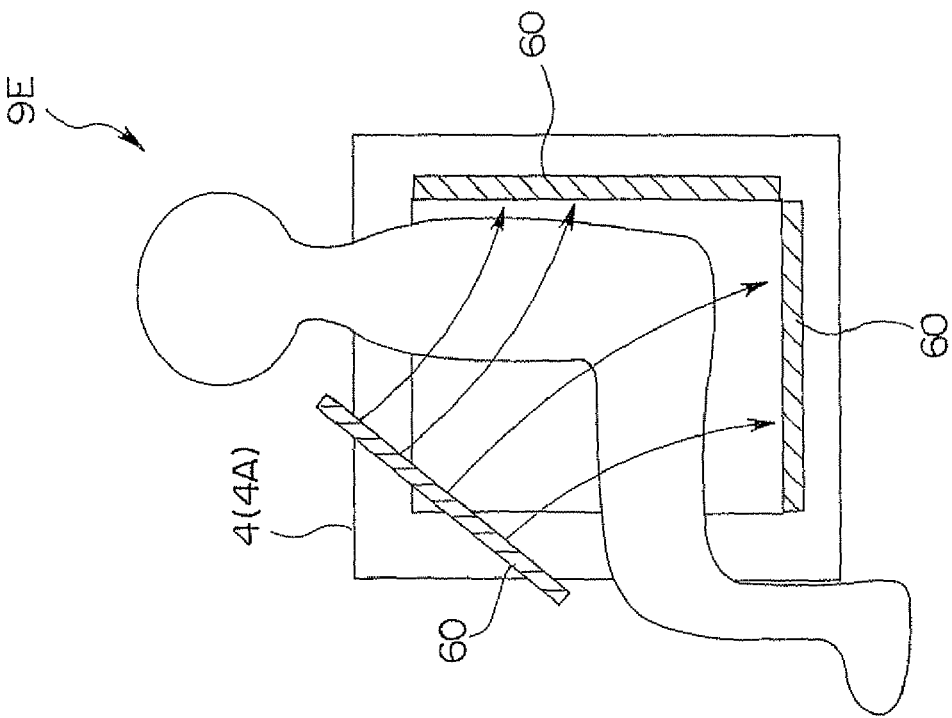
FIGS. 29A and 29B are explanatory diagrams showing a rotating magnetic field generating device and a position and posture detecting device forming a detecting system of the position and the posture of a capsule medical device according to a second embodiment.
Figure 29B:
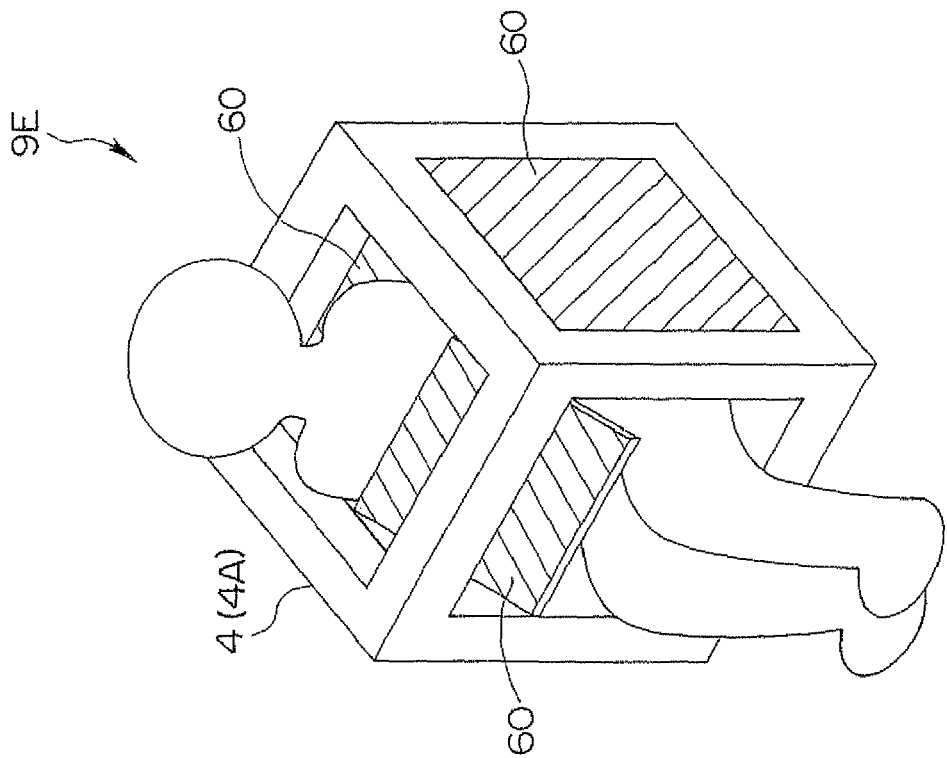
Figure 30:
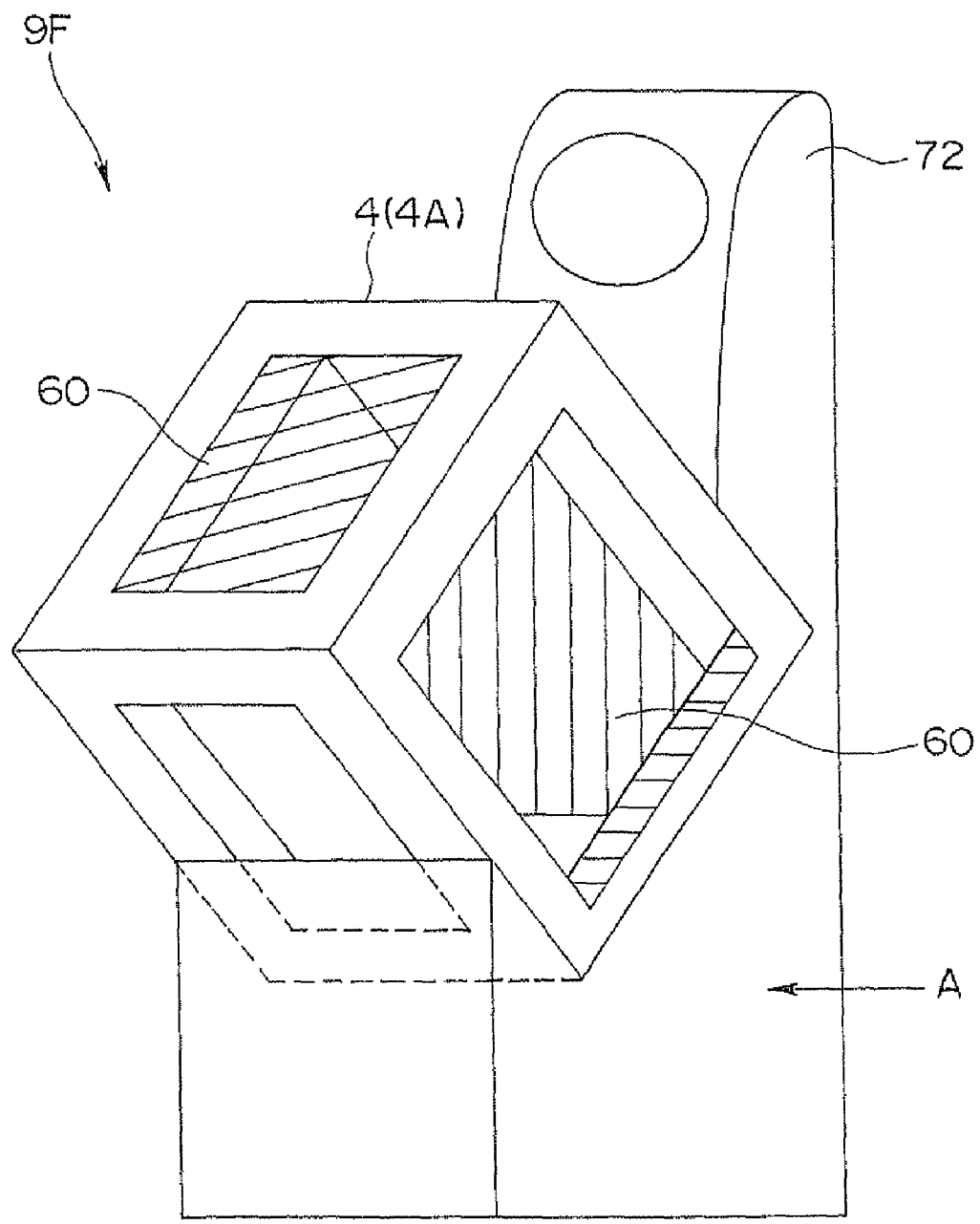
FIG. 30 is a perspective view schematically showing the rotating magnetic field generating device and the position and posture detecting device shown in FIGS. 29A and 29B according to a modification.
Figure 31:
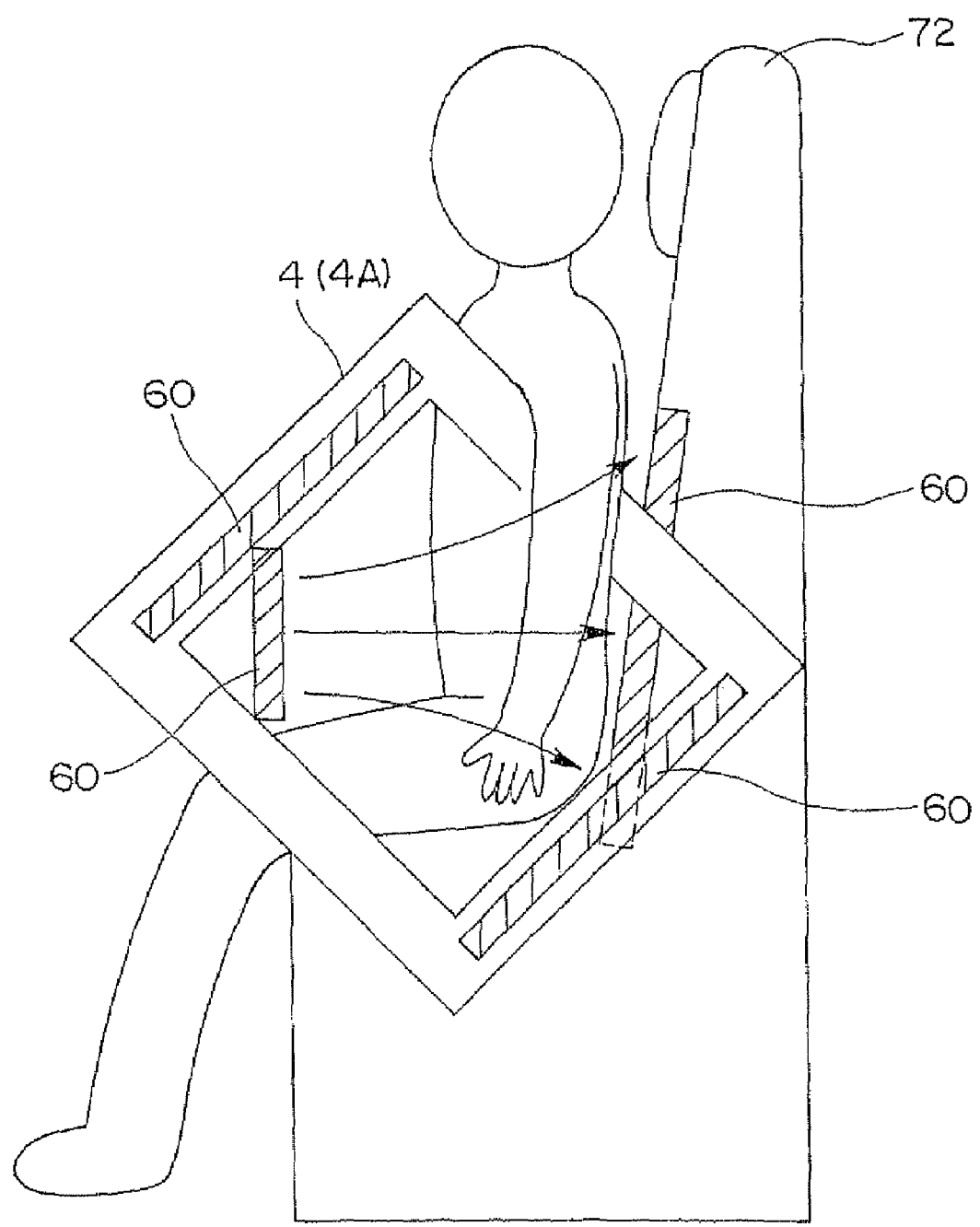
FIG. 31 is a sectional view schematically showing the inner structure of the rotating magnetic field generating device and the position and posture detecting device shown in FIG. 30 in the direction of an arrow A.

FIGS. 29A to 31 relate to a second embodiment of the present invention. FIGS. 29A and 29B are explanatory diagrams of a rotating magnetic field generating device and a position and posture detecting device forming a detecting system of the position and the posture of a capsule medical device according to the second embodiment, FIG. 29A is a perspective view schematically showing the rotating magnetic field generating device and the position and posture detecting device forming the detecting system of the position and the posture of the capsule medical device according to the second embodiment. FIG. 29B is a sectional view schematically showing the inner structure of the rotating magnetic field generating device and the position and posture detecting device shown in FIG. 29A. FIG. 30 is a perspective view schematically showing the rotating magnetic field generating device and the position and posture detecting device shown in FIGS. 29A and 29B according to the modification. FIG. 31 is a sectional view schematically showing the inner structure of the rotating magnetic field generating device and the position and posture detecting device shown in FIG. 30 in the direction of an arrow A.

According to the first embodiment, the system operates while the patient lays himself. However, according to the second embodiment, the system operates while the patient sits down. Other structures are the same as those according to the first embodiment, a description thereof is omitted, and the same reference numerals denote the same components.

Referring to FIGS. 29A and 29B, the detecting system of the position and the posture of the capsule medical device according to the second embodiment has a chair-type position and posture detecting device 9E in which the patient sits down.

Specifically, in the position and posture detecting device 9E, the position and posture detecting substrate 60 is attached to the rotating magnetic field generating device 4 serving as a cubical frame casing, having an opening for insertion of the living body so that the patient sits down. The position and posture detecting substrate 60 is arranged to the buttock and backrest of the patient, and further is arranged to the front portion of the patient, facing the buttock and backrest. Further, the position and posture detecting substrate 60 is arranged, facing both sides of the patient.

Thus, when the patient does not need to lay down himself, the position and posture detecting device 9E operates the system while the patient sits down.

Referring to FIGS. 30 and 31, a position and posture detecting device 9F may be arranged to a chair 72. Specifically, in the position and posture detecting device 9F, the rotating magnetic field generating device 4, serving as a cubical frame casing, having an opening for insertion of the living body is attached to the chair 72. The position and posture detecting substrate 60 is arranged to the buttock and backrest of the patient, and further is arranged to the front portion of the patient, facing the buttock and backrest.

Thus, the position and posture detecting device 9F enables the patient to easily sit down, as compared with the second embodiment. In this status, the system operated.

Other structures and operations are similar to those according to the first embodiment and thus a description thereof is omitted.

Third Embodiment

Figure 32:
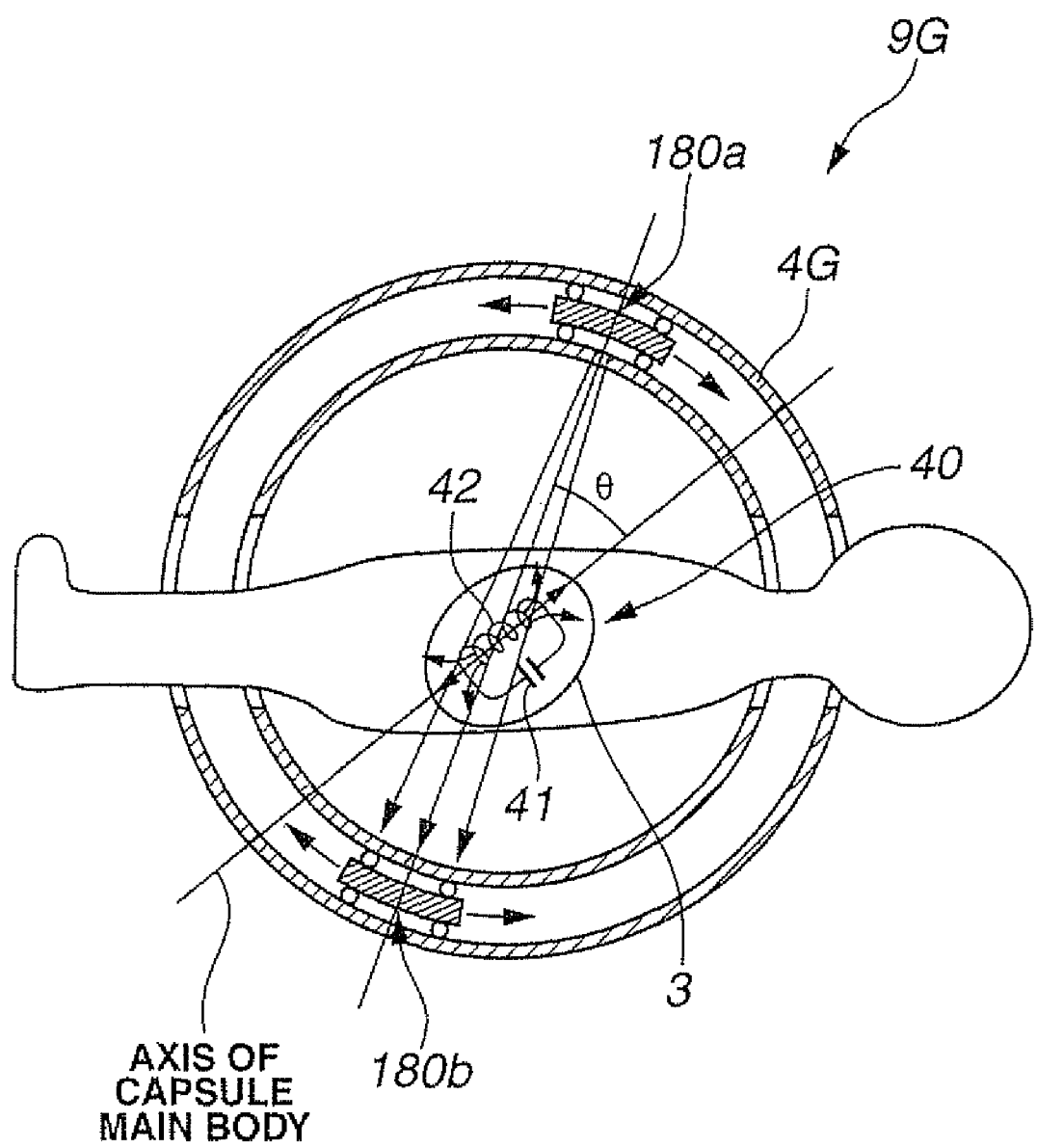
FIG. 32 is an explanatory diagram of a rotating magnetic field generating device and a position and posture detecting device forming a detecting system of the position and the posture of a capsule medical device according to a third embodiment.
Figure 33:
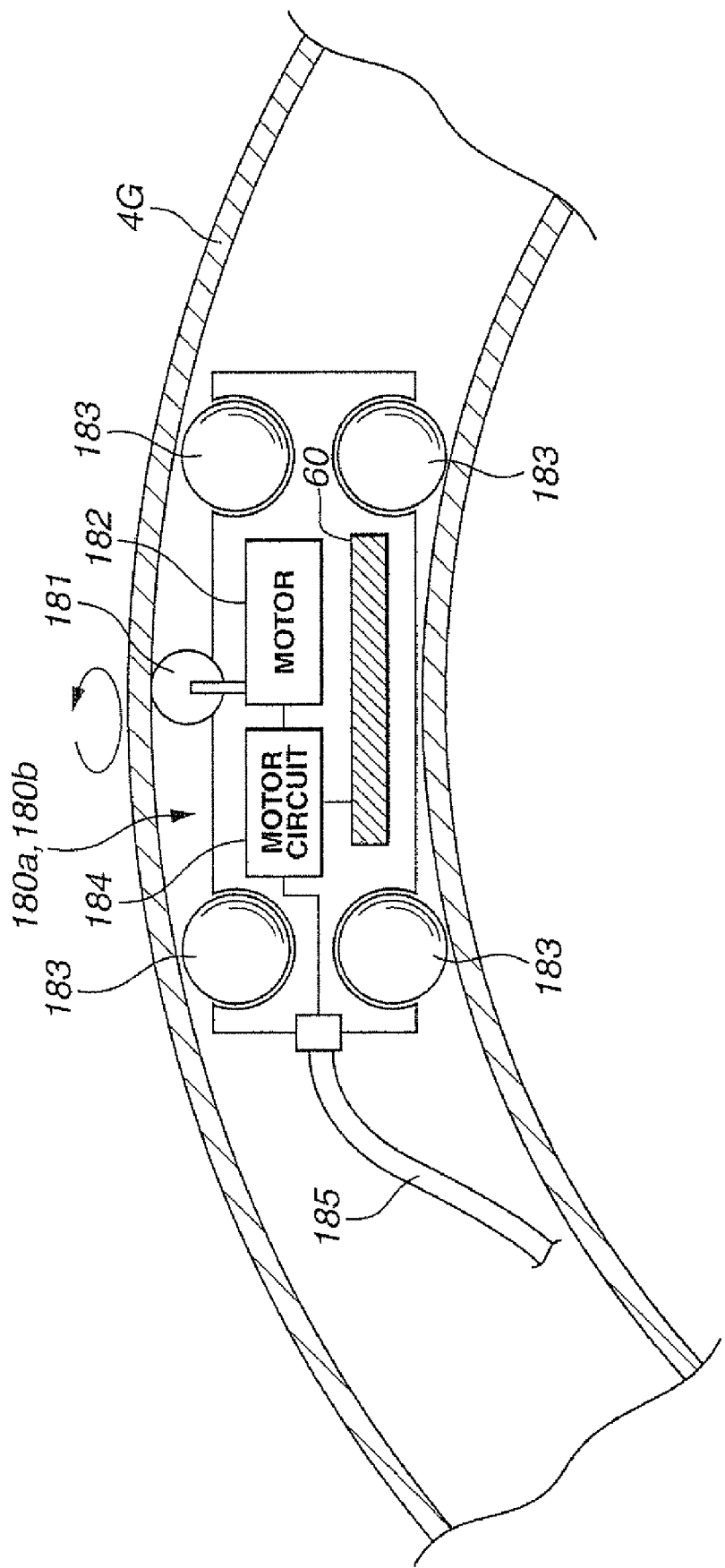
FIG. 33 is an enlarged view showing a main portion of the rotating magnetic field generating device and the position and posture detecting device shown in FIG. 32.
Figure 34:
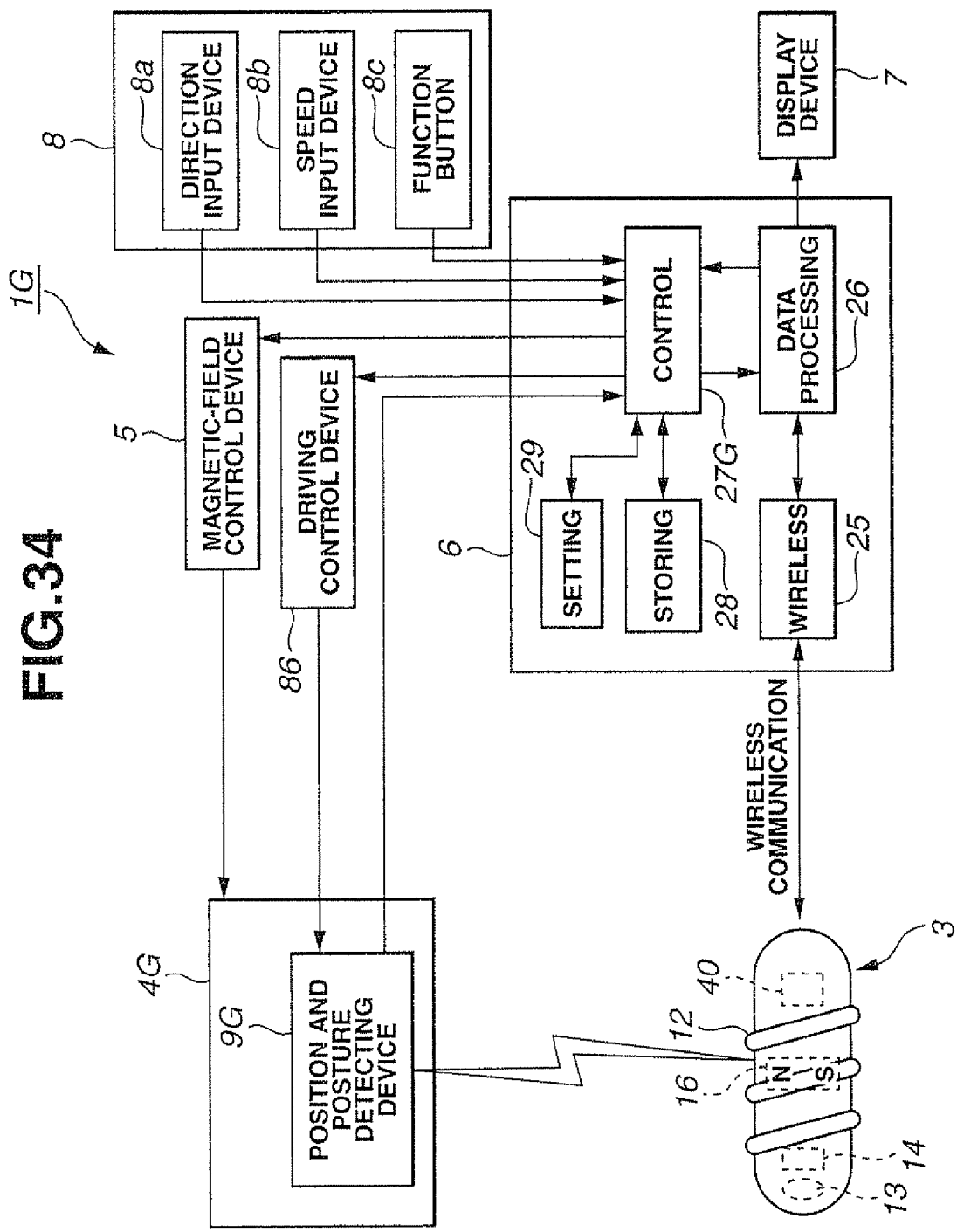
FIG. 34 is a diagram showing the entire structure of the detecting system of the position and posture of the capsule medical device according to the third embodiment.
Figure 35:
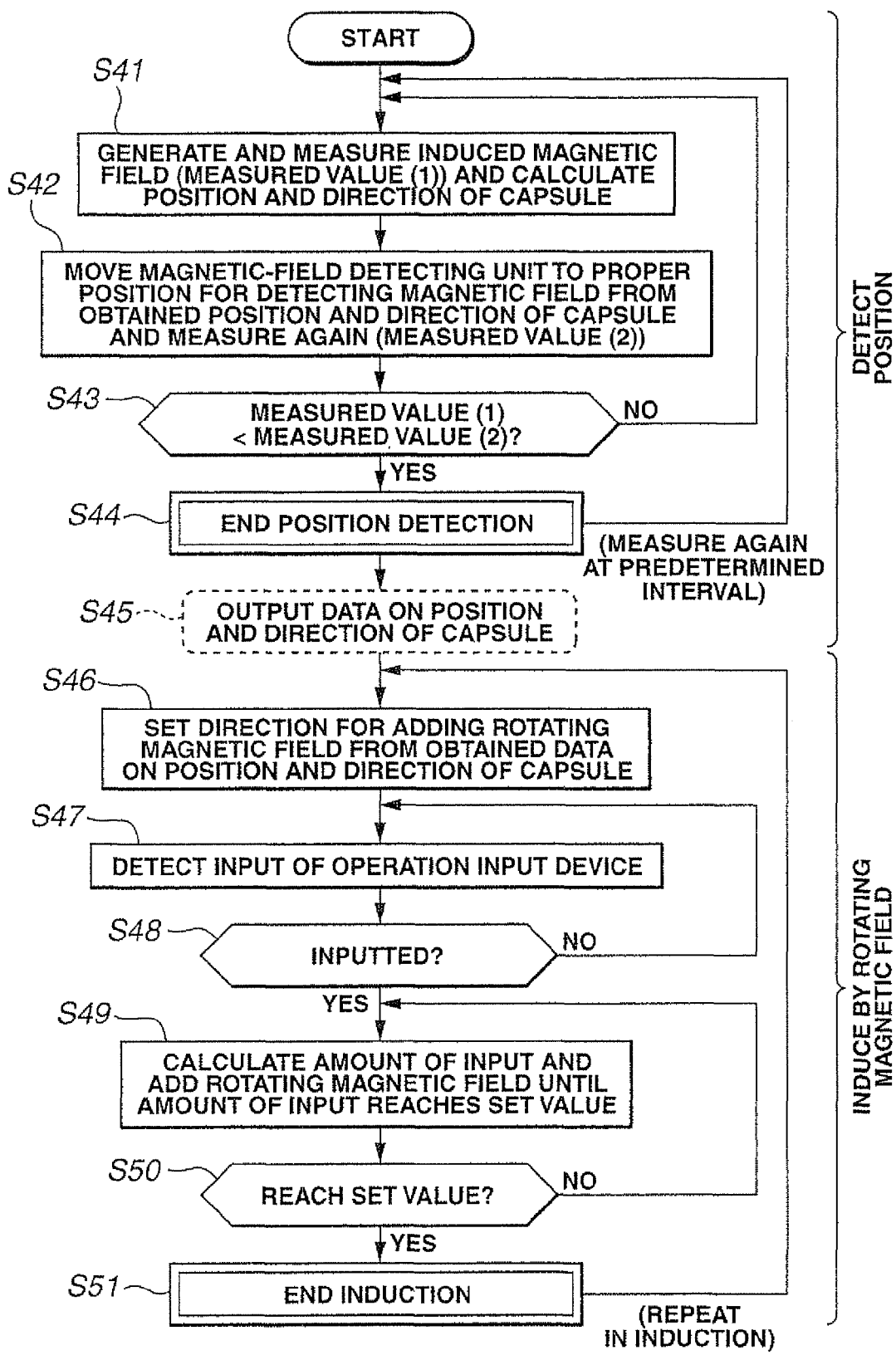
FIG. 35 is a flowchart showing the control operation of the detecting system of the position and posture of the capsule medical device according to the third embodiment.
Figure 36:
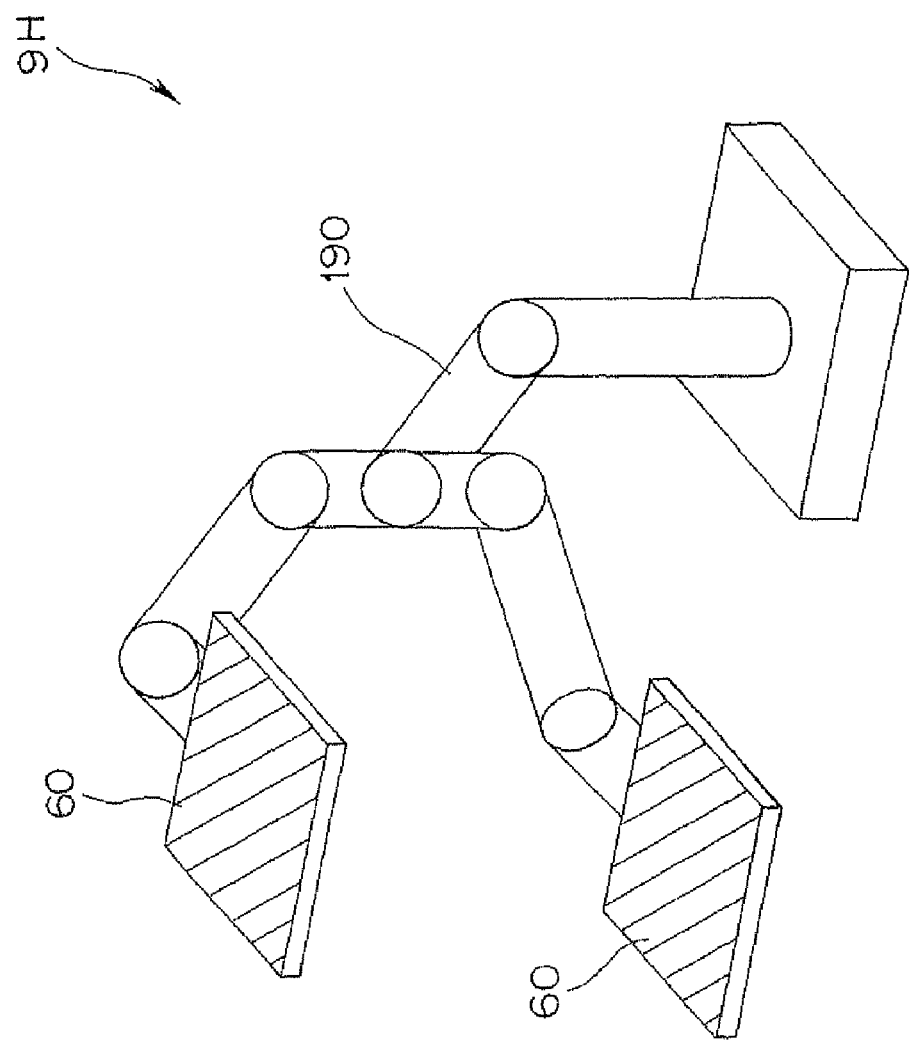
FIG. 36 is a perspective view schematically showing the position and posture detecting device shown in FIG. 32 according to a modification.
Figure 37:
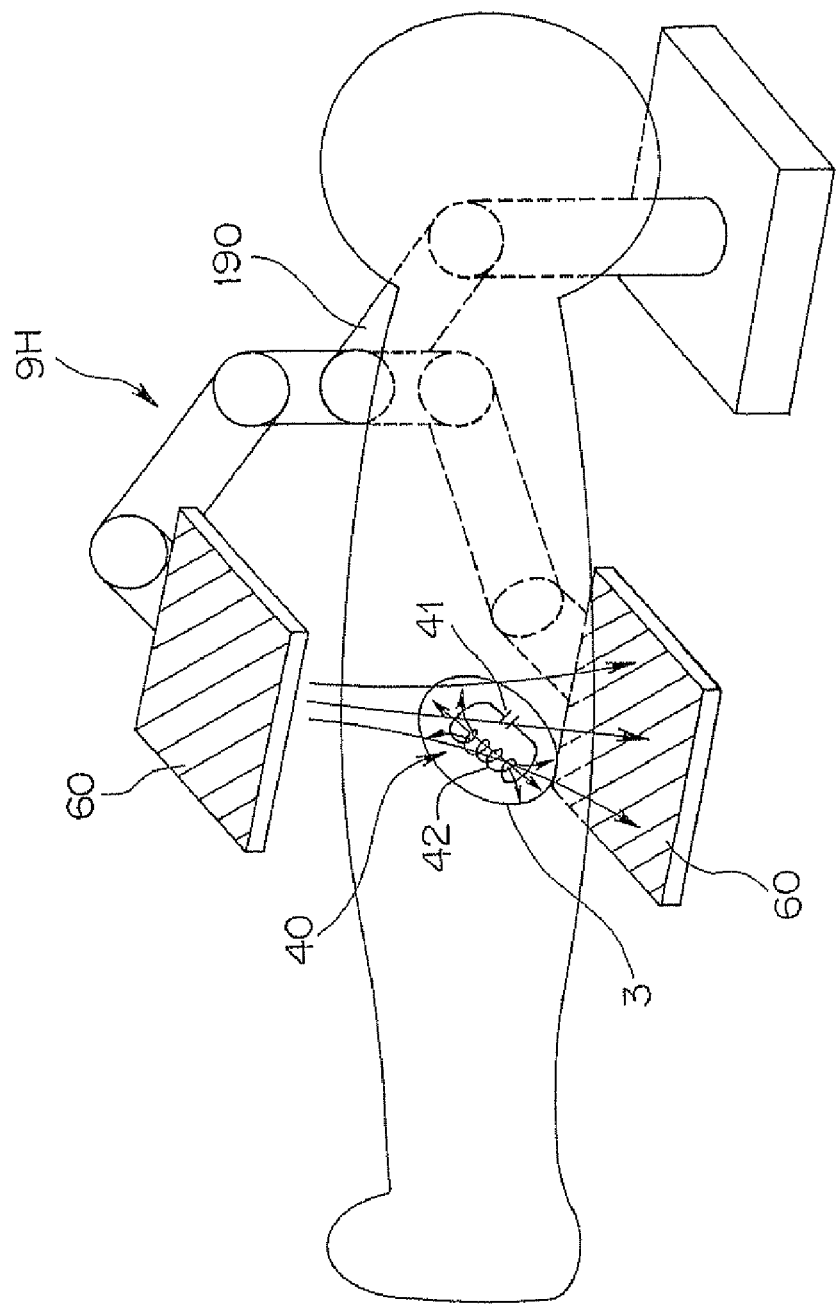
FIG. 37 is an explanatory diagram schematically showing the position and posture detecting device shown in FIG. 36.
Figure 38:
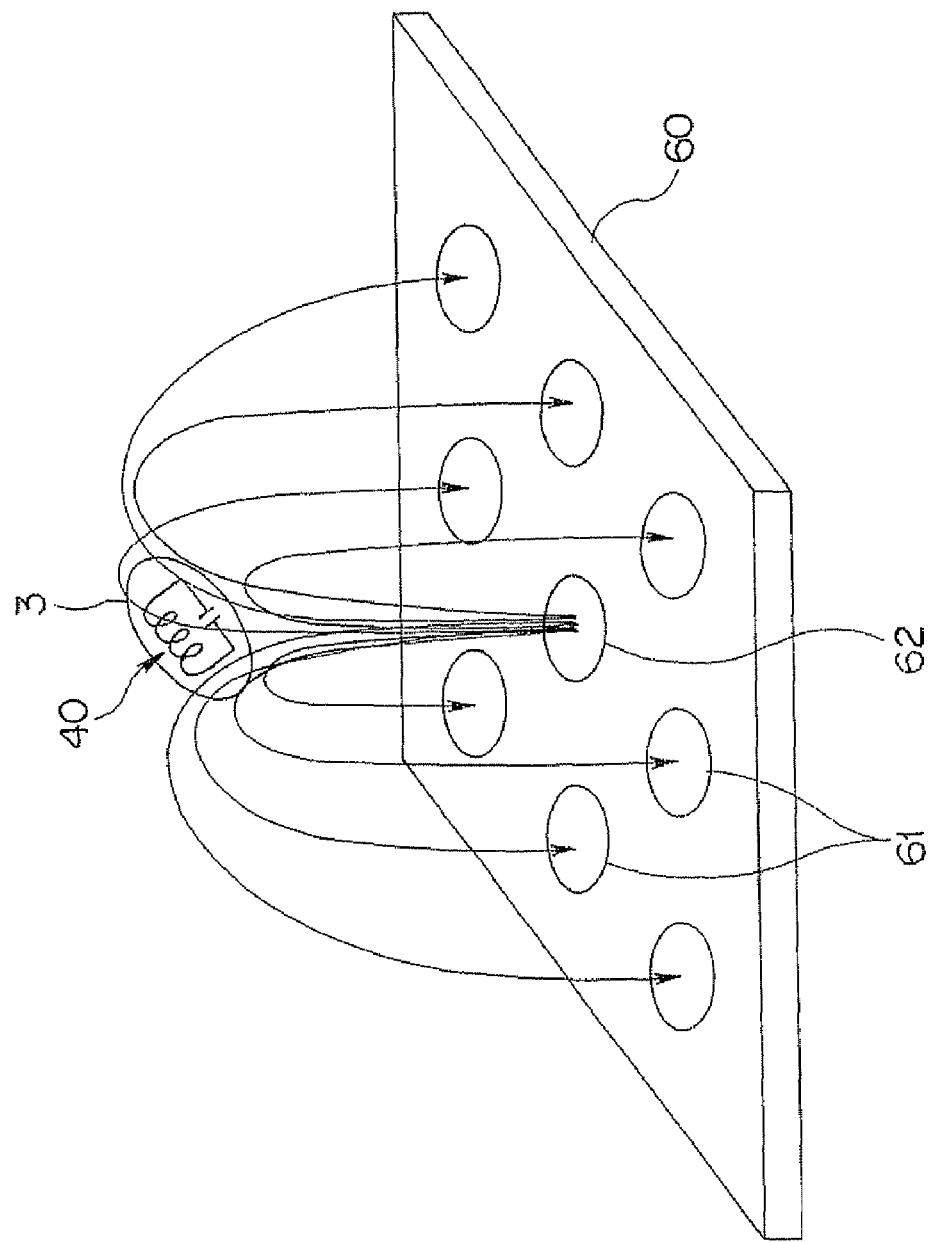
FIG. 38 is an explanatory diagram of the position and posture detection of the position and posture detecting device shown in FIG. 37 having a position and posture detecting substrate that is planar according to the modification.
Figure 39:
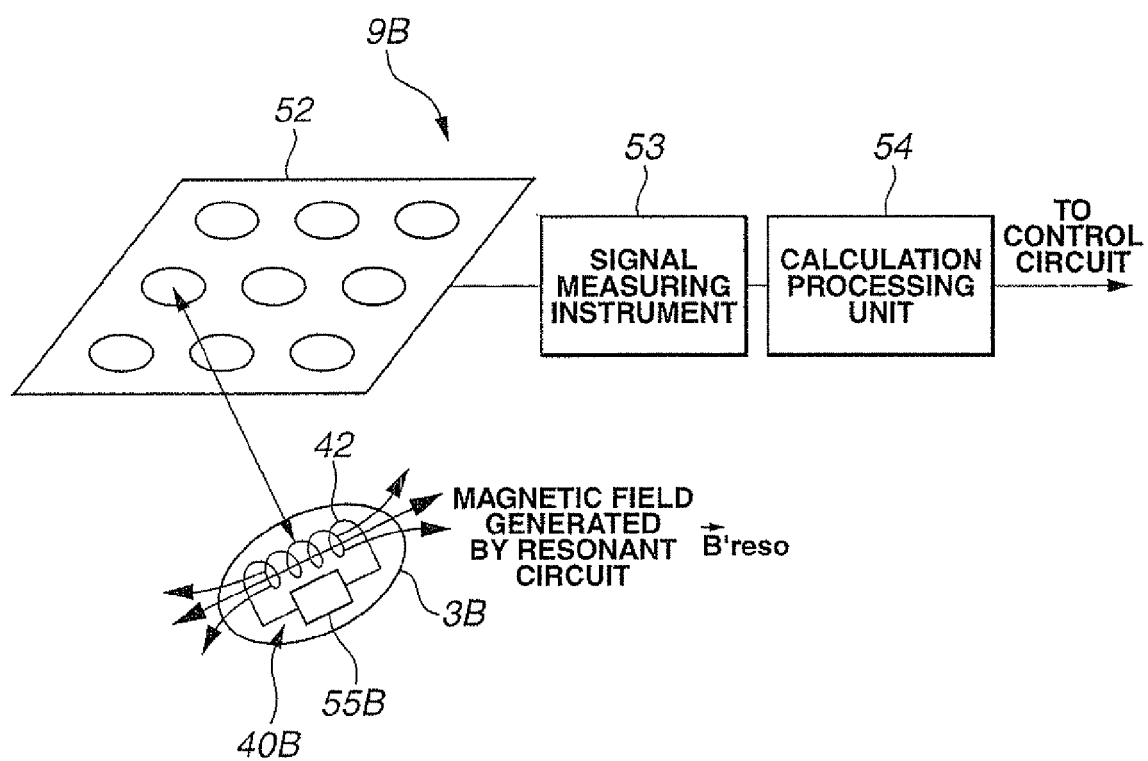
FIG. 39 is an explanatory diagram of the position and posture detection of the capsule main body having a resonant circuit having an oscillator in place of a capacitor in the position and posture detecting device.
Figure 40A:
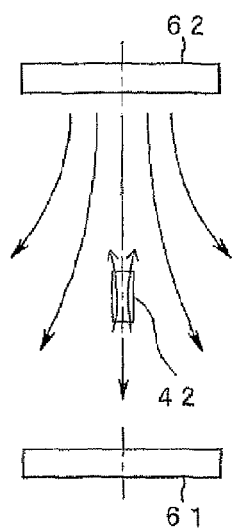
FIGS. 40A to 40C are explanatory diagrams schematically showing position relationships between an exciting coil and a detecting coil and a coil in a capsule.
Figure 40B:
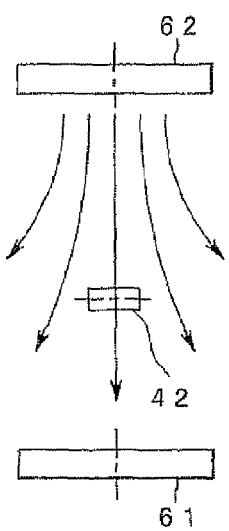
Figure 40C:
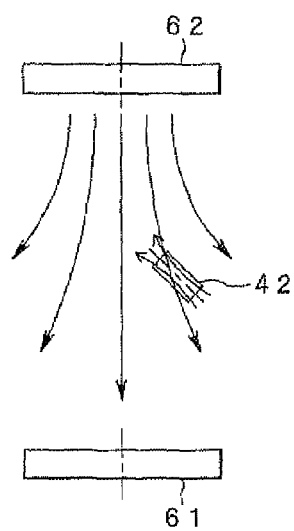

FIGS. 32 to 40C relate to a third embodiment of the present invention. FIG. 32 is an explanatory diagram of a rotating magnetic field generating device and a position and posture detecting device forming a detecting system of the position and the posture of a capsule medical device according to the third embodiment. FIG. 33 is an enlarged view showing a main portion of the rotating magnetic field generating device and the position and posture detecting device shown in FIG. 32. FIG. 34 is a diagram showing the entire structure of the detecting system of the position and posture of the capsule medical device according to the third embodiment. FIG. 35 is a flowchart showing the control operation of the detecting system of the position and posture of the capsule medical device according to the third embodiment. FIG. 36 is a perspective view schematically showing the position and posture detecting device shown in FIG. 32 according to the modification. FIG. 37 is an explanatory diagram schematically showing the position and posture detecting device shown in FIG. 36. FIG. 38 is an explanatory diagram of the position and posture detection of the position and posture detecting device shown in FIG. 37 having a position and posture detecting substrate that is planar according to the modification. FIG. 39 is an explanatory diagram of the position and posture detection of the capsule main body having a resonant circuit having an oscillator in place of a capacitor in the position and posture detecting device. FIGS. 40A to 40C are explanatory diagrams schematically showing position relationships between an exciting coil and a detecting coil and a coil in a capsule. FIG. 40A is an explanatory diagram schematically showing the position relationship when the axis connecting the exciting coil and the detecting coil is coaxial to the coil in the capsule. FIG. 40B is an explanatory diagram schematically showing the position relationship when the axis connecting the exciting coil and the detecting coil is perpendicular to the central axis of the coil in the capsule in the longitudinal direction. FIG. 40C is an explanatory diagram schematically showing the position relationship when the coil in the capsule is out of the axis connecting the exciting coil and the detecting coil.

The position and posture detecting substrate 60 is fixedly arranged according to the first and second embodiment. According to the third embodiment, the position and posture detecting substrate 60 can be moved to the best position during the examination. Other structures are the same as those of the first embodiment, so a description thereof is omitted, and the same reference numerals denote the same components.

As shown in FIGS. 32 to 34, a detecting system 1G of the position and posture of a capsule medical device according to the third embodiment comprises a rotating magnetic field generating device 4G serving as a frame casing having an opening for insertion of the living body, having position and posture detecting device 9G so that two movable units 180a and 180b having the position and posture detecting substrate 60 are moved to predetermined positions. The position and posture detecting substrate 60 has the plurality of detecting coils 61 and the exciting coil 62.

The rotating magnetic field generating device 4G can be divided into semi-spherical portions of a spherical member.

The movable units 180a and 180b are arranged to the semi-spherical portions of the rotating magnetic field generating device 4G, respectively. One of the movable units 180a and 180b generates the Alternating magnetic field for mutually inducing the resonant circuit 40 of the capsule main body 3 and the other movable unit detects the magnetic field generated by the resonant circuit 40 of the capsule main body 3.

Referring to FIG. 32, an exciting movable unit 180a is arranged at the semi-spherical portion on the top of the rotating magnetic field generating device 4G, and a detecting movable unit 180b is arranged at the semi-spherical portion on the bottom of the rotating magnetic field generating device 4G.

The movable units 180a and 180b are constructed so as to be movable to predetermined positions with a driving tire 181, of which direction can be turned to the right opposite direction, being connected to a motor 182. Specifically, the two position-and-posture-detecting substrates 60 sandwich the space of the capsule medical device, facing each other and are movably arranged while keeping the facing state. Four motion-passive tires 183 that are moved in accordance with the rotation of the driving tire 181 are rotatably arranged.

The motor 182 is driven and controlled by a motor driving circuit 184. The motor driving circuit 184 is connected to a driving control device 86 and the signal measuring instrument 53 described according to the first embodiment via a flexible substrate 185. The driving control device 86 controls the motor driving circuit 184 so that the movable units 180a and 180b are moved to predetermined positions.

The driving control device 86 is connected to a control circuit 27G of the processing device 6. The control circuit 27G controls the driving control device 86 so that the movable units 180a and 180b are moved to predetermined positions, in addition to the control operation described according to the first embodiment.

Specifically, when the distance from the coil 42 in the capsule to the exciting coil 62 is equal to the distance from the coil 42 in the capsule to the detecting coils 61, the number of patterns of the detecting magnetic fields is three as follows.

Referring to FIG. 40A, the detecting magnetic field is maximum when the axis connecting the exciting coil 62 and the detecting coils 61 is coaxial to the coil 42 in the capsule.

Referring to FIG. 40B, the magnetic fluxes from the exciting coil 62 do not enter the coil 42 in the capsule when the axis connecting the exciting coil 62 and the detecting coils 61 is perpendicular to the central axis of the coil 42 in the capsule in the longitudinal direction. Therefore, the induced magnetic field is not generated in the coil 42 in the capsule (resonant circuit 40) and the detecting coils 61 do not detect the magnetic field of the coil 42 in the capsule.

Referring to FIG. 40C, the detecting magnetic field is detected by the detecting coils 61, when the coil 42 in the capsule is deviated from the axis connecting the exciting coil 62 and the detecting coils 61 and the magnetic fluxes from the exciting coil 62 enter the coil 42 in the capsule to generate the induced magnetic field in the coil 42 in the capsule. However, in this case, the strength of the magnetic field detected by the detecting coils 61 varies depending on a relationship between the direction of the induced magnetic field generated in this case and the direction of the detecting coils 61 and the distance between the coil 42 in the capsule and the detecting coils 61.

The control circuit 27G controls the driving control device 86 at the proper position for preventing the reduction in magnetic field generated by the resonant circuit 40 of the capsule main body 3, detected by the position and posture detecting substrate 60, based on the past information on the direction and the position of the capsule main body 3 calculated by the calculation processing unit 54 from the measuring data from the signal measuring instrument 53.

The operation with the above-mentioned structure will be described according to the third embodiment.

In the examination of the body cavity with the capsule main body 3, the patient swallows the capsule main body 3. When the capsule main body 3 inserted in the body cavity passes through the esophagus, the illuminating element 15 illuminates the body cavity, the image picked-up by the image pickup element 14 is sent by radio to the extracorporeal processing device 6 via the wireless circuit 22.

The processing device 6 receives the image via the wireless circuit 25, stores the demodulated image data to an image storage device (such as a hard disk) arranged to the data processing circuit 26, performs the display processing, outputs the image data to the display device 7, and the images picked-up by the capsule main body 3 are sequentially displayed.

According to the third embodiment, the control circuit 27G generates the rotating magnetic field and controls the direction of the generated rotating magnetic field based on the information on the direction and position of the capsule main body 3 detected by the position and posture detecting device 9G in accordance with the flowchart shown in FIG. 35. Further, the control circuit 27G controls the operation for moving the movable units 180a and 180b to the proper positions.

First, the control circuit 27G detects the position of the capsule main body 3.

The control circuit 27G controls and drives the position and posture detecting device 9G to measure the position and direction of the capsule main body 3 (in step S41).

The position and posture detecting device 9G allows the oscillator 55 to oscillate (the exciting coil array 51 of) the position and posture detecting substrate 60 included in the movable unit 180a by a predetermined oscillating frequency of, e.g., 1 kHz to 1 MHz to generate the Alternating magnetic field.

The resonant circuit 40 of the capsule main body 3 generates the induced electromotive force by the mutual induction of the Alternating magnetic field, and further generates the magnetic field. The magnetic field from the resonant circuit 40 is detected by (the detecting coil array 52 of) the position and posture detecting substrate 60 included in the movable unit 10b. The measured value detected by the movable unit 180b is captured by the signal measuring instrument 53 and is inputted to the calculation processing unit 54.

The calculation processing unit 54 calculates the position and the direction of the resonant circuit 40 from the abovementioned formulae 1 and 2 based on the input measured value, and outputs, to the control circuit 27G, the measured value and the calculating result as data on the position and direction of the capsule main body 3 and the strength of magnetic field.

The control circuit 27G moves the movable units 180a and 180b to the proper positions for preventing the reduction in the magnetic field generated by the resonant circuit 40 from the data on the positions of the movable units 180a and 180b and the data on the direction and the position of the capsule main body 3 obtained based on the strength of magnetic field and the data on the direction and the position of the capsule main body 3 inputted by the position and posture detecting device 9G, and measures again the magnetic field (in step S42).

Further, the control circuit 27G compares the previous measured value with the re-measured value (in step S43). When the previous measured value is larger than the re-measured value, the control circuit 27G repeats the processing from steps S41 to S43 until the re-measured value is larger than the previous measured value.

The motor driving circuit 184 drives the motor 182 based on the driving signal from the driving control device 86 to rotate the driving tire 181 and the motion-passive tire 183 and thus the movable units 180a and 180b are moved to predetermined positions.

When the re-measured value is larger than the previous measured value, the control circuit 27G ends the position detection (in step S44), and controls the magnetic induction by using the next rotating magnetic field.

The degree of change of the direction varies, e.g., the capsule main body 3 excessively moves or hardly moves in accordance with the operation of the operation input device 8 depending on the status of the lumen, e.g., the existence of the body fluid or wall or the area of the organ, and such an error that the capsule main body 3 is not in the calculated direction thereof is caused.

Next, the control circuit 27G re-measures the magnetic field at a predetermined (time) interval, and controls the operation for repeating the position detection (steps S41 to S44) of the capsule main body 3.

Next, the control circuit 27G magnetically induces the capsule main body 3 by the rotating magnetic field.

The control circuit 27G outputs the data on the direction and position of the capsule main body 3 from the position and posture detecting device 9G (in step S45), and sets the direction (for magnetically inducing the capsule main body 3) of the rotating magnetic field added from the data on the direction and the position of the capsule main body 3 obtained by the calculation processing unit 54 (in step S46).

The control circuit 27G controls and drives the rotating magnetic field generating device 4 in accordance with the input from the operation input device 8 operated by the operator, e.g., the joystick of the direction input device 8a so as to control the capsule main body 3 at the desired position and direction. That is, the control circuit 27G detects an input of the operation input device 8 (joystick) (in step S47), and determines whether or not the operation is inputted by the operation input device 8 (in step S48). When the control circuit 27G determines that the operation is inputted by the operation input device 8, the control circuit 27G calculates the amount of input of the operation input device 8, and adds the rotating magnetic field generated by the rotating magnetic field generating device 4 until the amount of input of the operation input device 8 reaches a set value (in step S49). When the operation is not inputted by the operation input device 8, the control circuit 27G maintains the state of the set rotating magnetic field until the operation is inputted by the operation input device 8.

The control circuit 27G determines whether or not the added rotating magnetic field reaches the set value (in step S50), and continues to add the rotating magnetic field until the rotating magnetic field reaches the set value. When the rotating magnetic field reaches the set value, the control circuit 27G ends the magnetic induction (in step S51). Further, the control circuit 27G repeats the operation (in steps S46 to S51) for controlling the magnetic induction by the rotating magnetic field.

As a result, the detecting system 1G of the position and the posture of the capsule medical device moves the position and posture detecting substrate 60 to the proper position, in addition to the advantages similar to those according to the first embodiment, and continuously measures the direction and position of the capsule main body 3 with high precision.

In the flowchart shown in FIG. 35, the position and posture detecting substrate 60 can be moved. Except for the movement of the movable units, the flowchart shown in FIG. 35 can be applied to the case of fixedly arranging the position and posture detecting substrate 60.

The third embodiment has been described and further the following modifications are considered.

The detecting system of the position and the posture of the capsule medical device may use a movable arm 190 with multiple degree of freedom as the position and posture detecting device, in place of the movable units 180a and 180b, as shown in FIGS. 36 and 37.

Referring to FIGS. 36 and 37, a position and posture detecting device 9H comprises the movable arm 190 with multiple degree of freedom. The control device controls the operation of the movable arm with multiple degree of freedom so that the magnetic field detected by one specific position-and-posture-detecting-substrate 60 is maximum.

The movable arm 190 with multiple degree of freedom serving as a movable device is divided into two portions at the distal end thereof. The position and posture detecting substrates 60 are arranged to the two-divided distal end. One of the position and posture detecting substrates 60 is a detecting substrate, and the other is an exciting substrate. Alternatively, the position and posture detecting substrates 60 may periodically be switched, or one part of coils on the same position and posture detecting substrate may be used for the exciting ones, and other coils may be used for the detecting ones.

The movable arm 190 with multiple degree of freedom includes motors (not shown) at the joint portion thereof. The motors is controlled and driven by the driving control device 86 of the control circuit 27G, similarly to the movable units 180a and 180b described according to the third embodiment.

Other structures and operations are similar and therefore a description thereof is omitted.

Thus, the patient does not need to be hidden under the position and posture detecting device 9H and therefore the operation is extremely easy and the device size is reduced.

Referring to FIG. 38, the number of position and posture detecting substrates 60 attached to the movable arm 190 with multiple degree of freedom may be one. In this case, the exciting coil 62 is arranged to the center in the position and posture detecting substrate 60 and the detecting coils 61 are arranged around the exciting coil 62. As shown in FIG. 38, the line of magnetic field is outputted from the exciting coil 62 in the center of the position and posture detecting substrate, and is returned to the detecting coils 61 therearound.

On the position and posture detecting substrate 60, the exciting coil 62 generates the Alternating magnetic field for generating the induced magnetic field to the coil 42 in the capsule. The detecting coils 61 detect the induced magnetic field of the coil 42 in the capsule generated by the Alternating magnetic field. The detecting coils 61 are arranged in the same detecting direction and further are arranged on the same plane of the position and posture detecting substrate 60.

Therefore, the movable arm 190 with multiple degree of freedom has only one position and posture detecting substrate 60 having two functions of magnetic field generating means which generates the Alternating magnetic field for generating the induced magnetic field to the coil 42 in the capsule and magnetic field detecting means for detecting the strength of induced magnetic field generated by the coil 42 in the capsule. Therefore, the movable arm 190 with multiple degree of freedom is easily controlled and the size of the movable arm 190 with multiple degree of freedom is reduced, as compared with the case of using the two position and posture detecting substrates 60.

Referring to FIG. 39, the capsule main body 3 may voluntarily generate the induced magnetic field, in addition to generating the induced magnetic field by the Alternating magnetic field of the exciting coil array 51.

In this case, the capsule main body 3 comprises a resonant circuit 40B in which an oscillator 55B in place of the capacitor 41 is connected to the coil 42 in the capsule. The oscillator 55B is oscillated by an oscillating frequency of, e.g., 1 kHz to 1 MHz to generate the Alternating magnetic field for mutually inducing the resonant circuit 40B.

In the position and posture detecting device 9B, the detecting coil array 52 (detecting coil 61) detects the magnetic field voluntarily generated by the resonant circuit 40B of a capsule main body 3B. The position and posture detecting device 9B comprises the signal measuring instrument 53 which measured the signal detected by the detecting coil array 52 (detecting coil 61) and the calculation processing unit 54 which calculates the direction of the capsule main body 3B and the position thereof.

A measurement magnetic field $B'_{total}$ (vector) detected by the detecting coil array 52 (detecting coil 61) is obtained as follows by using a magnetic field $B'_{reso}$ (vector) generated by the resonant circuit 40B.

$$\vec{B}'_{total} = \vec{B}'_{reso} \qquad \text{(Formula 3)}$$

The magnetic field $B'_{reso}$ generated by the resonant circuit 40B is obtained in substantially the same way by the formula 2 described according to the first embodiment and a description thereof is omitted here.

Thus, the calculation processing unit 54 sets the measurement magnetic field $B'_{total}$ detected by the detecting coil array 52 (detecting coil 61) as the magnetic field $B'_{reso}$ generated by the resonant circuit 40B, and calculates the direction (θ, φ) and an equivalent magnetic moment M of the capsule main body 3B and the position (x, y, z) of the capsule main body 3B.

The capsule main body 3B voluntarily generates the magnetic field by the resonant circuit 40B and therefore the position and posture detecting device 9B does not need the exciting means which generates the Alternating magnetic field for generating the induced electromotive force in the resonant circuit 40B, and the size of the position and posture detecting device 9B is further reduced.

The embodiments obtained by partly combining the above embodiments belong to the present invention.

Advantageously, the detecting system of the position and the posture of the capsule medical device according to the embodiments of the present invention accurately detects the direction and the position of the main body of the capsule medical device without any influence on the rotating magnetic field for magnetically inducing the main body of the capsule medical device.

What is claimed is:

1. A capsule medical device system comprising a posture detecting system for detecting the posture of a main body of a capsule medical device, the posture detecting system comprising:

a coil in the capsule provided in the main body of the capsule medical device;

a first magnetic field generating device for generating an alternating magnetic field to cause the coil in the capsule to generate an induced electromotive force;

a magnetic field detecting device for detecting the strength of a magnetic field from the coil in the capsule;

a calculation processing unit for calculating the posture and the position of the main body of the capsule medical device in response to a detection value from the magnetic field detecting device;

a power supply circuit connected to the coil in the capsule, for supplying power to an internal circuit of the main body of the capsule medical device; and a switch section for switching connection states, which is provided between the power supply circuit and the coil in the capsule.

2. The capsule medical device system according to claim 1, further comprising:

a magnet provided to the main body of the capsule medical device to be inserted in a body cavity;

a first magnetic field generating device for generating a magnetic field in an arbitrary direction;

a thrust generating mechanism for causing the main body of the capsule medical device to generate a thrust by an action between the magnetic field generated by the first magnetic field generating device and the magnet; and a control device for controlling the magnetic field to be generated by the first magnetic field generating device based on posture information of the main body of the capsule medical device detected by the posture detecting system.

3. A capsule medical device system comprising a posture detecting system for detecting the posture of a main body of a capsule medical device, the posture detecting system comprising:

a coil in the capsule provided in the main body of the capsule medical device;

a first magnetic field generating device for generating an alternating magnetic field to cause the coil in the capsule to generate an induced electromotive force;

a magnetic field detecting device for detecting the strength of a magnetic field from the coil in the capsule;

a calculation processing unit for calculating the posture and the position of the main body of the capsule medical device in response to a detection value from the magnetic field detecting device;

a power supply circuit connected to the coil in the capsule, for supplying power to an internal circuit of the main body of the capsule medical device;

a capacitor connected to the coil in the capsule; and a switch section for switching connection state, which is provided between the coil in the capsule and the capacitor.

4. The capsule medical device system according to claim 3, further comprising:

a magnet provided to the main body of the capsule medical device to be inserted in a body cavity;

a first magnetic field generating device for generating a magnetic field in an arbitrary direction;

a thrust generating mechanism for causing the main body of the capsule medical device to generate a thrust by an action between the magnetic field generated by the first magnetic field generating device and the magnet; and a control device for controlling the magnetic field to be generated by the first magnetic field generating device based on posture information of the main body of the capsule medical device detected by the posture detecting system.

5. A capsule medical device system comprising a posture detecting system for detecting the posture of a main body of a capsule medical device, the posture detecting system comprising:

a coil in the capsule provided in the main body of the capsule medical device;

a first magnetic field generating device for generating an alternating magnetic field to cause the coil in the capsule to generate an induced electromotive force;

a magnetic field detecting device for detecting the strength of the magnetic field generated from the coil in the capsule; and a calculation processing unit calculating the posture and the position of the main body of the capsule medical device in response to a detection value from the magnetic field detecting device, wherein a primary side of a transformer is connected to a resonant circuit including a capacitor connected to the coil in the capsule, and a coil on a secondary side of the transformer is connected to a power supply circuit, and the power supply circuit supplies power to an internal circuit of the main body of the capsule medical device.

6. The capsule medical device system according to claim 5, further comprising:

a magnet provided to the main body of the capsule medical device to be insert a body cavity;

a first magnetic field generating device for generating a magnetic field in an arbitrary direction;

a thrust generating mechanism for causing the main body of the capsule medical device to generate a thrust by an action between the magnetic field generated by the first magnetic field generating device and the magnet; and a control device for controlling the magnetic field to be generated by the first magnetic field generating device based on posture information of the main body of the capsule medical device detected by the posture detecting system.

7. A control method for a capsule medical device system comprising a posture detecting system for detecting the posture of a main body of a capsule medical device, comprising the steps of a first magnetic field generating device generating an alternating magnetic field to cause a coil in the capsule provided to the main body of the capsule medical device to generate an induced electromotive force;

a power supply circuit connected to the coil in the capsule supplying power to an internal circuit of the main body of the capsule medical device;

a switch section switching connection states between the power supply circuit and the coil in the capsule;

a magnetic field detecting device detecting the strength of a magnetic field from the coil in the capsule; and a calculation processing unit calculating the posture and the position of the main body of the capsule medical device in response to a detection value from the magnetic field detecting device.

8. The control method for a capsule medical device system according to claim 7, further comprising the steps of:

a first magnetic field generating device generating a magnetic field in an arbitrary direction;

a thrust generating mechanism causing the main body of the capsule medical device to generate a thrust by an action between the magnetic field generated by the first magnetic field generating device and a magnet provided to the main body of the capsule medical device to be inserted in a body cavity; and a control device controlling the magnetic field to be generated by the first magnetic field generating device based on posture information of the main body of the capsule medical device detected by the posture detecting system.

9. A control method for a capsule medical device system comprising a posture detecting system for detecting the posture of a main body of a capsule medical device, comprising the steps of a first magnetic field generating device generating an alternating magnetic field to cause a coil in the capsule provided to the main body of the capsule medical device to generate an induced electromotive force;

a power supply circuit connected to the coil in the capsule supplying power to an internal circuit of the main body of the capsule medical device;

a switch section switching connection states between the coil in the capsule and a capacitor connected to the coil in the capsule;

a magnetic field detecting device detecting the strength of a magnetic field from the coil in the capsule; and a calculation processing unit calculating the posture and the position of the main body of the capsule medical device in response to a detection value from the magnetic field detecting device.

10. The control method for a capsule medical device system according to claim 9, further comprising the steps of:

a first magnetic field generating device generating a magnetic field in an arbitrary direction;

a thrust generating mechanism causing the main body of the capsule medical device to generate a thrust by an action between the magnetic field generated by the first magnetic field generating device and a magnet provided to the main body of the capsule medical device to be inserted in a body cavity; and a control device controlling the magnetic field to be generated by the first magnetic field generating device based on posture information of the main body of the capsule medical device detected by the posture detecting system.

11. A control method for a capsule medical device system comprising a posture detecting system for detecting the posture of a main body of a capsule medical device, comprising the steps of a first magnetic field generating device generating an alternating magnetic field to cause a coil in the capsule provided to the main body of the capsule medical device to generate an induced electromotive force;

a magnetic field detecting device detecting the strength of a magnetic field generated from the coil in the capsule;

a calculation processing unit for calculating the posture and the position of the main body of the capsule medical device in response to a detection value from the magnetic field detecting device; and a power supply circuit supplying power to an internal circuit of the main body of the capsule medical device, the power supply circuit being connected to a coil on a secondary side of a transformer and a primary side of the transformer being connected to a resonant circuit including a capacitor connected to the coil in the capsule.

12. The control method for a capsule medical device system according to claim 11, further comprising the steps of:

a first magnetic field generating device generating a magnetic field in an arbitrary direction;

a thrust generating mechanism causing the main body of the capsule medical device to generate a thrust by an action between the magnetic field generated by the first magnetic field generating device and a magnet provided to the main body of the capsule medical device to be inserted in a body cavity; and a control device controlling the magnetic field to be generated by the first magnetic field generating device based on posture information of the main body of the capsule medical device detected by the posture detecting system.

* * * * *